United States Patent [19]

Brooks et al.

[11] Patent Number: 5,512,581

[45] Date of Patent: Apr. 30, 1996

[54] IMINOXYCARBOXYLATES AND DERIVATIVES AS INHIBITORS OF LEUKOTRIENE BIOSYNTHESIS

[75] Inventors: Dee W. Brooks; Pramila Bhatia, both of Libertyville; Teodozyi Kolasa, Lake Villa, all of Ill.

[73] Assignee: Abbott Laboratories, Abbott park, Ill.

[21] Appl. No.: 432,491

[22] Filed: May 1, 1995

Related U.S. Application Data

[62] Division of Ser. No. 276,148, Jul. 18, 1994, abandoned.

[51] Int. Cl.[6] .................... A61K 31/47; C07D 215/227; C07D 215/36; C07D 215/12
[52] U.S. Cl. .................... 514/311; 514/312; 546/175; 546/174; 546/157; 546/172
[58] Field of Search .................. 514/311, 312; 546/157, 174, 175, 172

[56] References Cited

U.S. PATENT DOCUMENTS

| | | | |
|---|---|---|---|
| 4,970,215 | 11/1990 | Mohrs et al. | 514/311 |
| 5,234,932 | 8/1993 | Rachlin et al. | 514/311 |
| 5,358,955 | 10/1994 | Brooks et al. | 514/311 |

FOREIGN PATENT DOCUMENTS

| | | |
|---|---|---|
| 0349062 | 1/1990 | European Pat. Off. . |
| 529450 | 3/1993 | European Pat. Off. . |
| WO94/10148 | 5/1994 | WIPO . |

OTHER PUBLICATIONS

P. Prasis, et al., Bioorganic and Medicinal Chemistry Letters 1 (11):645–648 1991.
Kolasa, et al., Tetrahedron, vol. 44, No. 17, pp. 5431–5440, 1988.
Herscheid, et al., J. Org. Chem., vol. 46, No. 16, 1981.

Primary Examiner—Johann Richter
Assistant Examiner—Laura R. Cross
Attorney, Agent, or Firm—Jerry F. Janssen

[57] ABSTRACT

The present invention relates to a compound of formula

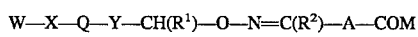

$$W-X-Q-Y-CH(R^1)-O-N=C(R^2)-A-COM$$

or a pharmaceutically acceptable salt thereof wherein W is optionally substituted aryl or heteroaryl; X is a valence bond, or methylene, divalent alkylene, alkenylene, alkynylene or alkyloxy; Q is a valence bond, or —O—, —S—, $>NR^4$ or $>NCOR^5$; Y is optionally substituted phenyl, biphenyl, naphthyl, tetrahydronaphthyl, indolyl, pyridyl, or benzo[b]thienyl, thienyl, thiazolyl, or thiazolylphenyl; $R^1$ is alkyl, cycloalkyl, alkoxyalkyl, aryl or arylalkyl, heteroaryl or heteroarylalkyl; $R^2$ is hydrogen, alkyl or hydroxyalkyl; A is a valence bond or is selected from alkylene, alkenylene, alkynylene, cycloalkylene, phenylene, pyridylene, thienylene and furylene; and M is a pharmaceutically acceptable, metabolically cleavable group, $—OR^6$, $—NR^6R^7$, —NH-tetrazoyl, —NH-2-, 3-, or 4-pyridyl, and —NH-2-, 4-, or 5-thiazolyl which inhibit leukotriene biosynthesis and are useful in the treatment of inflammatory disease states. Also disclosed are leukotriene biosynthesis inhibiting compositions and a method for inhibiting lipoxygenase activity and leukotriene biosynthesis.

5 Claims, No Drawings

IMINOXYCARBOXYLATES AND DERIVATIVES AS INHIBITORS OF LEUKOTRIENE BIOSYNTHESIS

This application is a division of U.S. patent application Ser. No. 08/276,148 filed Jul. 18, 1994 now abandoned.

TECHNICAL FIELD

This invention relates to compounds having activity to inhibit lipoxygenase enzymes, to pharmaceutical compositions comprising these compounds, and to a medical method of treatment. More particularly, this invention concerns oxime carboxylate compounds which inhibit leukotriene biosynthesis, to pharmaceutical compositions comprising these compounds and to a method of inhibiting leukotriene biosynthesis.

BACKGROUND OF THE INVENTION

The leukotrienes are extremely potent substances which produce a wide variety of biological effects, often in the nanomolar to picomolar concentration range. Leukotrienes are important pathological mediators in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

Compounds which prevent leukotriene biosynthesis are thus useful in the treatment of disease states such as those listed above in which the leukotrienes play an important pathophysiological role.

U.S. Pat. No. 4,970,215 to Mohrs et al. discloses and claims certain 4-(quinolin-2-yl-methoxy)phenyl-cycloalkylacetic acids for inhibiting leukotrienes synthesis.

European Patent Application 0 349 062 to Zamboni et al. discloses and claims certain 2-quinolylmethoxyphenyl substituted thioalkanoic acid derivatives as leukotriene biosynthesis inhibitors. Prasit et al. in Bioorganic and Medicinal Chemistry Letters 1, 645–648 (1991) describe {[4-(4-chlorophenyl)-1-[4-(2-quinolylmethoxy)phenyl]butyl]thio}acetic acid, L-674,636, as a new, potent and orally active leukotriene synthesis inhibitor.

SUMMARY OF THE INVENTION

In its principal embodiment, the present invention provides a compound of formula:

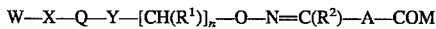

W—X—Q—Y—[CH(R$^1$)]$_n$—O—N=C(R$^2$)—A—COM or a pharmaceutically acceptable salt thereof where n is zero or 1 with the proviso that n is zero when Y is tetrahydronaphthyl.

W is selected from (a) phenyl, (b) phenyl substituted with halogen, nitrile, alkyl of one to six carbon atoms, alkoxy of one to six carbon atoms, thiazolyl, thiazolyl substituted with halogen, alkyl of one to six carbon atoms, or alkoxy of one to six carbon atoms, pyridyl, or pyridyl substituted with halogen, alkyl of one to six carbon atoms, or alkoxy of one to six carbon atoms, (c) naphthyl, (d) naphthyl substituted with halogen, alkyl of one to six carbon atoms, or alkoxy of one to six carbon atoms, (e) pyridyl, (f) pyridyl substituted with (f-1) halogen, (f-2) alkyl of one to six carbon atoms, (f-3) alkoxy of one to six carbon atoms, (f4) phenoxy, or (f-5) phenoxy substituted with halogen, alkyl of one to six carbon atoms, or alkoxy of one to six carbon atoms, (g) quinolyl, (h) quinolyl substituted with halogen, alkyl of one to six carbon atoms, or alkoxy of one to six carbon atoms, (i) benzothienyl, (j) benzothienyl substituted with halogen, alkyl of one to six carbon atoms, or alkoxy of one to six carbon atoms, (k) benzothiazolyl, (l) benzothiazolyl substituted with halogen, alkyl of one to six carbon atoms, or alkoxy of one to six carbon atoms, (l) benzoxazolyl, (m) benzoxazolyl substituted with halogen, alkyl of one to six carbon atoms, or alkoxy of one to six carbon atoms, (n) benzimidazolyl, (o) benzimidazolyl substituted with halogen, alkyl of one to six carbon atoms, or alkoxy of one to six carbon atoms, (p) quinoxalinyl, (q) quinoxalinyl substituted with halogen, alkyl of one to six carbon atoms, or alkoxy of one to six carbon atoms, (r) pyrimidyl, (s) pyrimidyl substituted with halogen, alkyl of one to six carbon atoms, or alkoxy of one to six carbon atoms, (t) thiazolyl, (u) thiazoyl substituted with (u-1) halogen, (u-2) alkyl of one to six carbon atoms, (u-3) alkoxy of one to six carbon atoms, (u-4) phenyl, (u-5) phenyl substituted with halogen, alkyl of one to six carbon atoms, or alkoxy of one to six carbon atoms, (u-6) pyridyl, or (u-7) pyridyl substituted with halogen, alkyl of one to six carbon atoms, or alkoxy of one to six carbon atoms, (v) pyridothiazolyl, and (w) pyridothiazolyl substituted with halogen, alkyl of one to six carbon atoms, or alkoxy of one to six carbon atoms.

X is selected from alkylene of one to six carbon atoms, alkenylene of two to six carbon atoms, alkynylene of two to six carbon atoms, alkoxy of one to six carbon atoms, thioalkyloxy of one to six carbon atoms, and alkylsulfonyl of one to six carbon atoms.

Q is a valence bond or is selected from —O—, —S—, >NR$^4$ where R$^4$ is hydrogen, or alkyl of one to six carbon atoms, and >NCOR$^5$ where R$^5$ is alkyl of one to six carbon atoms, amino, or alkylamino of one to six carbon atoms.

Y is selected from (a) phenyl, (b) phenyl substituted with halogen, alkyl of one to six carbon atoms, or alkoxy of one to six carbon atoms, (c) biphenyl, (d) biphenyl substituted with halogen, alkyl of one to six carbon atoms, or alkoxy of one to six carbon atoms, (e) naphthyl, (f) naphthyl substituted with halogen, alkyl of one to six carbon atoms, or alkoxy of one to six carbon atoms, (g) tetrahydronaphthyl, (h) tetrahydronaphthyl substituted with halogen, alkyl of one to six carbon atoms, or alkoxy of one to six carbon atoms, (i) indolyl, (j) indolyl substituted with halogen, alkyl of one to six carbon atoms, or alkoxy of one to six carbon atoms, (k) benzothienyl, (l) benzothienyl substituted with halogen, alkyl of one to six carbon atoms, or alkoxy of one to six carbon atoms, (m) pyridyl, (n) pyridyl substituted with halogen, alkyl of one to six carbon atoms, or alkoxy of one to six carbon atoms, (o) thienyl, (p) thienyl substituted with halogen, alkyl of one to six carbon atoms, or alkoxy of one to six carbon atoms, (q) thiazolyl, (r) thiazolyl substituted with halogen, alkyl of one to six carbon atoms, or alkoxy of one to six carbon atoms, (s) benzo[b]furyl, (t) benzo[b]furyl substituted with halogen, alkyl of one to six carbon atoms, or alkoxy of one to six carbon atoms, (u) benzo[b]thiazolyl, (v) benzo[b]thienyl substituted with halogen, alkyl of one to six carbon atoms, or alkoxy of one to six carbon atoms, (w) thiazolylphenyl, and (x) thiazolylphenyl substituted with halogen, alkyl of one to six carbon atoms, or alkoxy of one to six carbon atoms.

R$^1$ is selected from (a) alkyl of one to twelve carbon atoms, (b) cycloalkyl of three to ten carbon atoms, (c) cycloalkyl of three to ten carbon atoms containing one atom selected from —O—, —S—, >NR$^4$ where R$^4$ is hydrogen, or alkyl of one to six carbon atoms, and >NCOR$^5$ where R$^5$ is alkyl of one to six carbon atoms, amino, or alkylamino of one to six carbon atoms, (d) alkoxyalkyl in which the alkoxy and alkyl portions independently are of one to twelve carbon atoms, (e) phenyl, or phenyl substituted with halogen, alkyl of one to six carbon atoms, haloalkyl of one to six carbon atoms, or alkoxy of one to six carbon atoms, (f) phenylalkyl in which the alkyl portion is of one to six carbon atoms, or phenylalkyl in which the phenyl ring is substituted with halogen, alkyl of one to six carbon atoms, haloalkyl of one to six carbon atoms, or alkoxy of one to six carbon atoms, (g) pyridyl, or pyridyl substituted with halogen, alkyl of one to six carbon atoms, haloalkyl of one to six carbon atoms, or alkoxy of one to six carbon atoms, (h) thiazolyl, or thiazolyl substituted with halogen, alkyl of one to six carbon atoms, haloalkyl of one to six carbon atoms, or alkoxy of one to six carbon atoms, (i) thienyl, or thienyl substituted with halogen, alkyl of one to six carbon atoms, haloalkyl of one to six carbon atoms, or alkoxy of one to six carbon atoms, (j) furyl, or furyl substituted with halogen, alkyl of one to six carbon atoms, haloalkyl of one to six carbon atoms, or alkoxy of one to six carbon atoms, (k) oxazolyl, or oxazolyl substituted with halogen, alkyl of one to six carbon atoms, haloalkyl of one to six carbon atoms, or alkoxy of one to six carbon atoms, (l) pyridazolyl, or pyridazolyl substituted with halogen, alkyl of one to six carbon atoms, haloalkyl of one to six carbon atoms, or alkoxy of one to six carbon atoms, (m) pyridylalkyl where the alkyl portion is of one to six carbon atoms, or pyridylalkyl in which the pyridyl ring is substituted with halogen, alkyl of one to six carbon atoms, haloalkyl of one to six carbon atoms, alkoxy of one to six carbon atoms, (n) thiazolylalkyl wherein the alkyl portion is of one to six carbon atoms, or thiazolylalkyl in which the thiazolyl ring is substituted with halogen, alkyl of one to six carbon atoms, haloalkyl of one to six carbon atoms, or alkoxy of one to six carbon atoms, (o) thienylalkyl where the alkyl portion is of one to six carbon atoms, or thienylalkyl in which the thienyl ring is substituted with halogen, alkyl of one to six carbon atoms, haloalkyl of one to six carbon atoms, or alkoxy of one to six carbon atoms, (p) furylalkyl where the alkyl portion is of one to six carbon atoms, or furylalkyl in which the furyl ring is substituted with halogen, alkyl of one to six carbon atoms, haloalkyl of one to six carbon atoms, or alkoxy of one to six carbon atoms, (q) oxazolylalkyl wherein the alkyl portion is of one to six carbon atoms, or oxazolylalkyl in which the oxazolyl ring is substituted with halogen, alkyl of one to six carbon atoms, haloalkyl of one to six carbon atoms, or alkoxy of one to six carbon atoms, and (r) pyridazolylalkyl wherein the alkyl portion is of one to six carbon atoms, or pyridazolylalkyl in which the pyridazolyl ring is substituted with halogen, alkyl of one to six carbon atoms, haloalkyl of one to six carbon atoms, or alkoxy of one to six carbon atoms.

R$^2$ is selected from hydrogen, alkyl of one to six carbon atoms, and hydroxyalkyl of one to six carbon atoms.

A is a valence bond or is selected from (a) alkylene of one to six carbon atoms, (b) cycloalkylene of three to eight carbon atoms, (c) phenyl, or phenyl substituted with halogen, alkyl of one to six carbon atoms, haloalkyl of one to six carbon atoms, or alkoxy of one to six carbon atoms, (d) phenylalkyl in which the alkyl portion is of one to six carbon atoms, or phenylalkyl substituted with halogen, alkyl of one to six carbon atoms, haloalkyl of one to six carbon atoms, or alkoxy of one to six carbon atoms, (e) pyridyl, or pyridyl substituted with halogen, alkyl of one to six carbon atoms, haloalkyl of one to six carbon atoms, or alkoxy of one to six carbon atoms, (f) thiazolyl, or thiazolyl substituted with halogen, alkyl of one to six carbon atoms, haloalkyl of one to six carbon atoms, or alkoxy of one to six carbon atoms, (g) thienyl, or thienyl substituted with halogen, alkyl of one to six carbon atoms, haloalkyl of one to six carbon atoms, or alkoxy of one to six carbon atoms, (h) furyl, or furyl substituted with halogen, alkyl of one to six carbon atoms, haloalkyl of one to six carbon atoms, or alkoxy of one to six carbon atoms, (i) oxazolyl, or oxazolyl substituted with halogen, alkyl of one to six carbon atoms, haloalkyl of one to six carbon atoms, or alkoxy of one to six carbon atoms, (j) pyridylalkyl wherein the alkyl portion is of one to six carbon atoms, or pyridylalkyl in which the pyridyl ring is substituted with halogen, alkyl of one to six carbon atoms, haloalkyl of one to six carbon atoms, or alkoxy of one to six carbon atoms, (k) thiazolylalkyl wherein the alkyl portion is of one to six carbon atoms, or thiazolylalkyl in which the thiazolyl ring is substituted with halogen, alkyl of one to six carbon atoms, haloalkyl of one to six carbon atoms, or alkoxy of one to six carbon atoms, (l) thienylalkyl where the alkyl portion is of one to six carbon atoms, or thienylalkyl in which the thienyl ring is substituted with halogen, alkyl of one to six carbon atoms, haloalkyl of one to six carbon atoms, or alkoxy of one to six carbon atoms, (m) furylalkyl where the alkyl portion is of one to six carbon atoms, or furylalkyl in which the furyl ring is substituted with halogen, alkyl of one to six carbon atoms, haloalkyl of one to six carbon atoms, or alkoxy of one to six carbon atoms, (n) oxazolylalkyl wherein the alkyl portion is of one to six carbon atoms, or oxazolylalkyl where the oxazolyl ring is substituted with halogen, alkyl of one to six carbon atoms, haloalkyl of one to six carbon atoms, or alkoxy of one to six carbon atoms.

M is selected from (a) a pharmaceutically acceptable, metabolically cleavable group, (b) —OR$^6$ where R$^6$ is selected from hydrogen or alkyl of one to six carbon atoms, (c) —NR$^6$R$^7$ where R$^7$ is selected from hydrogen, alkyl of one to six carbon atoms, hydroxy, alkoxy or one to six carbon atoms, or R$^6$ and R$^7$ taken together define a five- to eight-membered ring which may contain one or two additional oxygen, sulfur and nitrogen atoms, (d) —NH-tetrazoyl, (e) —NH-2-, 3-, or 4-pyridyl, and (f) —NH-2-, 4-, or 5-thiazolyl.

The present invention also provides pharmaceutical compositions which comprise a therapeutically effective amount of compound of claim 1 in combination with a pharmaceutically acceptable carrier.

The invention further relates to a method of inhibiting leukotriene biosynthesis in a host mammal in need of such treatment comprising administering to a mammal in need of such treatment a therapeutically effective amount of a compound of claim 1.

DETAILED DESCRIPTION

As used throughout this specification and the appended claims, the following terms have the meanings specified.

The term alkyl refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms alkoxy and alkoxyl denote an alkyl group, as defined above, attached to the parent molecular moiety through an oxygen atom. Representative alkoxy groups include methoxy, ethoxy, propoxy, butoxy, and the like.

The terms alkenyl as used herein refer to monovalent straight or branched chain groups of 2 to 6 carbon atoms containing a carbon-carbon double bond, derived from an alkene by the removal of one hydrogen atom and include, but are not limited to groups such as ethenyl, 1-propenyl, 2-propenyl, 2-methyl-1-propenyl, 1-butenyl, 2-butenyl and the like.

The term alkylene denotes a divalent group derived from a straight or branched chain saturated hydrocarbon containing by the removal of two hydrogen atoms, for example —CH$_2$—, —CH$_2$CH$_2$—, —CH(CH$_3$)CH$_2$— and the like.

The term alkenylene denotes a divalent group derived from a straight or branched chain hydrocarbon containing at least one carbon-carbon double bond. Examples of alkenylene include —CH=CH—, —CH$_2$CH=CH—, —C(CH$_3$)=CH—, —CH$_2$CH=CHCH$_2$—, and the like.

The terms alkynylene refers to a divalent group derived by the removal of two hydrogen atoms from a straight or branched chain acyclic hydrocarbon group containing at least one carbon-carbon triple bond. Examples of alkynylene include —CH≡CH—, —CH≡C—CH$_2$—, —CH≡CH—CH(CH$_3$)— and the like.

The term aryl as used herein refers to a monovalent carbocyclic group containing one or more fused or non-fused phenyl rings and includes, for example, phenyl, 1- or 2-naphthyl, 1,2-dihydronaphthyl, 1,2,3,4-tetrahydronaphthyl, and the like.

The term cycloalkyl as used herein refer to a monovalent saturated cyclic hydrocarbon group. Representative cycloalkyl groups include cyclopropyl, cyclobutyl, cyclopentyl, cyclohexyl, cycloheptyl, bicyclo[2.2.1]heptane and the like.

Cycloalkylene denotes a divalent radical derived from a cycloalkane by the removal of two hydrogen atoms.

The term haloalkyl denotes an alkyl group, as defined above, having one, two, or three halogen atoms attached thereto and is exemplified by such groups as chloromethyl, bromoethyl, trifluoromethyl, and the like.

The term metabolically cleavable group denotes a group which is cleaved in vivo to yield the parent molecule of the formula I indicated above wherein M is hydrogen. Examples of metabolically cleavable groups include —COR, —COOR, —CONRR and —CH$_2$OR radicals where R is selected independently at each occurrence from alkyl, trialkylsilyl, carbocyclic aryl or carbocyclic aryl substituted with one or more of C$_1$–C$_4$ alkyl, halogen, hydroxy or C$_1$–C$_4$ alkoxy. Specific examples of representative metabolically cleavable groups include acetyl, methoxycarbonyl, benzoyl, methoxymethyl and trimethylsilyl groups.

The terms phenylene, pyridylene, thienylene, and furylene refer to divalent radicals derived by the removal of two hydrogen atoms from the ring systems of benzene, pyridine, thiophene, and furan, respectively.

By pharmaceutically acceptable salt it is meant those salts which are, within the scope of sound medical judgement, suitable for use in contact with the tissues of humans and lower animals without undue toxicity, irritation, allergic response and the like, and are commensurate with a reasonable benefit/risk milo. Pharmaceutically acceptable salts are well known in the art. For example, S. M Berge, et al. describe pharmaceutically acceptable salts in detail in *J. Pharmaceutical Sciences*, 1977, 66:1– 19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Asymmetric centers may exist in the compounds of the present invention. The present invention contemplates the various stereoisomers and mixtures thereof. Individual stereoisomers of compounds of the present invention are made by synthesis from starting materials containing the chiral centers or by preparation of mixtures of enantiomeric products follwed by separation as, for example, by conversion to a mixture of diastereomers followed by separation by recrystallization or chromatographic techniques, or by direct separation of the optical enantiomers on chiral chromatographic columns. Starting compounds of particular stereochemistry are either commercially available or are made by the methods detailed below and resolved by techniques well known in the organic chemical arts.

Compounds contemplated as falling within the scope of the present invention include, but are not limited to

[cyclohexyl-(4-(2-quinolylmethoxy)phenyl)methyl]iminoxyacetic acid,

[cyclohexyl-(4-(2-quinolylmethoxy)phenyl)methyl]-2-iminoxy propionic acid,

[cyclohexyl-(4-(2-quinolylmethoxy)phenyl)methyl]-4-iminoxy pentanoic acid,

[cyclohexyl-(4-(2-quinolylmethoxy)phenyl)methyl]-2-iminoxy-3-(4-hydroxyphenyl)propionic acid,

[cyclohexyl-(4-(2-quinolylmethoxy)phenyl)methyl]-2-iminoxy-3-phenylpropionic acid, O-[cyclohexyl-(4-(2-quinolylmethoxy)phenyl)methyl]-4-carboxybenzaldoxime,

[cyclohexyl-(4-(2-quinolylmethoxy)phenyl)methyl]-3-iminoxy-(2,2-dimethyl) propionic acid,

[cyclopentyl-(4-(2-quinolylmethoxy)phenyl)methyl]iminoxy acetic acid,

[cyclopentyl-(4-(2-quinolylmethoxy)phenyl)methyl]-2-iminoxy propionic acid,

[1,2,3,4-tetrahydro-6-(2-quinolylmethoxy)naphth-1-yl]iminoxy acetic acid,

[1,2,3,4-tetrahydro-6-(2-quinolylmethoxy)naphth-1-yl]-2-iminoxypropionic acid,

[4-(4-chlorophenyl)-1-(4-(2-quinolylmethoxy)phenyl)butyl]iminoxyacetic acid,

[2-cyclohexyl-1-(4-(2-quinolylmethoxy)phenyl)eth-1-yl]iminoxyacetic acid,

O-[2-cyclohexyl-1-(4-(2-quinolylmethoxy)phenyl)eth-1-yl]-4-carboxybenzaldoxime,

[2-cyclohexyl-1-(4-(2-quinolylmethoxy)phenyl)eth-1-yl]-2-iminoxypropionic acid,

[2-cyclohexyl-1-(4-(2-quinolylmethoxy)phenyl)eth-1-yl]-4-iminoxypentanoic acid,

[cycloheptyl-(4-(2-quinolylmethoxy)phenyl)methyl]iminoxy acetic acid,
[3-cyclohexyl-2-[4-(2-quinolylmethoxy)phenyl)prop-1-yl] iminoxy acetic acid,
[3-cyclohexyl-2-(4-(2-quinolyl methoxy)phenyl)prop-1-yl]-2-iminoxypropionic acid,
[3-cyclohexyl-2-(4-(2-quinolylmethoxy)phenyl)prop-1-yl}-3-iminoxy-(2,2-dimethyl)propionic acid,
[4-(4-fluorophenyl)-1-(4-(2-quinolylmethoxy)phenyl)but-1-yl]iminoxyacetic acid,
[4-(4-fluorophenyl)-1-(4-(2-quinolylmethoxy)phenyl)but-1-yl]-2-iminoxypropionic acid,
[2-cyclohexyl-2-(4-(2-quinolylmethoxy)phenyl)eth-1-yl}iminoxyacetic acid,
[2-cycloheptyl-2-(4-(2-quinolylmethoxy)phenyl)eth-1-yl] iminoxyacetic acid,
[2-cycloheptyl-2-(4-(2-quinolylmethoxy)phenyl)eth-1-yl]-3-iminoxy-2,2-dimethylpropionic acid,
[2-cyclopentyl-2-(4-(2-quinolylmethoxy)phenyl)eth-1-yl] iminoxyacetic acid,
[cyclohexyl-(4-(2-quinolylmethoxy)phenyl)methyl]-Z-2-iminoxypropionic acid methyl ester,
[cyclohexyl-(4-(2-quinolylmethoxy)phenyl)methyl]-E-2-iminoxypropionic acid methyl ester,
[cyclohexyl-(4-(2-quinolylmethoxy)phenyl)methyl]-Z-2-iminoxy propionic acid,
[cyclohexyl-(4-(2-quinolylmethoxy)phenyl)methyl]-E-2-iminoxy propionic acid,
(R)-[cyclohexyl-(4-(2-quinolylmethoxy)phenyl]methyl]-E-2-iminoxypropionic acid methyl ester,
(R)-[cyclohexyl-(4-(2-quinolylmethoxy)phenyl)methyl]-E-2-iminoxypropionic acid,
(S)-[cyclohexyl-(4-(2-quinolylmethoxy)phenyl)methyl]-E-2-iminoxypropionic acid methyl ester,
(S)-[cyclohexyl-(4-(2-quinolylmethoxy)phenyl)methyl]-E-2-iminoxypropionic acid,
[cyclohexyl-(4-(2-quinolylmethoxy)phenyl)methyl]-Z-iminoxy acetic acid methyl ester,
[cyclohexyl-(4-(2-quinolylmethoxy)phenyl)methyl]-E-iminoxy acetic acid methyl ester,
[cyclohexyl-(4-(2-quinolylmethoxy)phenyl)methyl]-E-iminoxy acetic acid,
[2-phenyl-1-(4-(2-quinolylmethoxy)phenyl)eth-1-yl]-Z-2-iminoxy propionic acid,
[2-phenyl-1-(4-(2-quinolylmethoxy)phenyl)eth-1-yl]-E-2-iminoxy propionic acid,
[2-thienyl-(4-(2-quinolylmethoxy)phenyl)methyl]-E-2-iminoxy propionic acid,
[cyclohexyl-(2-chloro4-(2-quinolylmethoxy)phenyl)methyl]-E-2-iminoxypropionic acid,
[cyclohexyl-(3-chloro4-(2-quinolylmethoxy)phenyl)methyl]-E-2-iminoxypropionic acid,
[cyclohexyl-(2-chloro4-(2-quinolylmethoxy)phenyl)methyl]-Z-2-iminoxypropionic acid,
[3-methyl-3-phenyl-1-[4-(2-quinolylmethoxy)phenyl)but-1-yl]-Z-2-iminoxypropionic acid,
[3-methyl-3-phenyl-1-(4-(2-quinolylmethóxy)phenyl)but-1-yl]-E-2-iminoxypropionic acid,
[3-methyl-3-phenyl-1-(4-(2-quinolylmethoxy)phenyl)but-1-yl]-E-2-iminoxyacetic acid,
[4-(2-quinolylmethoxy)phenylpent-1-yl]-E-2-iminoxypropionic acid,
[4-(2-quinolylmethoxy)phenyl)pent-1-yl]-E-iminoxyacetic acid,
[4-(2-quinolylmethoxy)phenyl)-but-3-en-1-yl]-E-iminoxy-2-propionic acid,
[cyclohexyl-(4-(2-quinolylmethoxy)phenyl)methyl]-E-2-iminoxy butanoic acid,
[cyclohexyl-(4-(2-quinolylmethoxy)phenyl)methyl]-E-3-iminoxybutanoic acid,
[cyclohexyl-1-(4-(2-quinolylmethoxy)phenyl)eth-2-yl]-2-iminoxy propionic acid,
[cycloheptyl-(4-(2-quinolylmethoxy)phenyl)eth-2-yl]-2-iminoxy propionic acid,
[2-chloro-(4-(2-quinolylmethoxy)phenyl)methyl]-2-iminoxy propionic acid,
[cycloheptyl-(4-(2-quinolylmethoxy)phenyl)methyl]-2-iminoxy propionic acid,
Sodium [cyclohexyl-(4-(2-quinolylmethoxy)phenyl)methyl]-2-iminoxypropionate,
(R)-[cyclopentyl-(4-(2-quinolylmethoxy)phenyl)methyl]-E-2-iminoxypropionic acid,
(S)-[cyclopentyl-(4-(2-quinolylmethoxy)phenyl)methyl]-E-2-iminoxypropionic acid,
[cyclohexyl-(4-(2-quinolylmethoxy)benzo[b]thien-2-yl)methyl]-2-iminoxypropionic acid,
[cyclohexyl-(6-(2-quinolylmethoxy)pyrid-3-yl)methyl]iminoxy acetic acid,
[cyclohexyl-(4-(2-quinolylmethoxy)phenyl)methyl]-2-iminoxy propionic acid 2-thiazolylamide,
[cyclohexyl-(4-(2-quinolinylmethoxy)phenyl)methyl]-2-iminoxy propionic acid 2-pyridylamide,
[cyclohexyl-(4-(2-quinolinylmethoxy)phenyl)methyl]-2-iminoxypropionic acid 5-tetrazylamide,
[cyclohexyl-(4-(6-(4-fluorophenoxy)pyrid-2-ylmethoxy)phenyl)methyl]iminoxy acetic acid,
[2-cyclohexyl-1-(4-(4-thiazolylmethoxy)phenyl)eth-1-yl] iminoxy acetic acid,
O-[2-cyclohexyl-1-(4-(4-thiazolylmethoxy)phenyl)eth-1-yl]-4-carboxybenzaldoxime,
[2-cyclohexyl-1-(4-(4-thiazolylmethoxy)phenyl)eth-1-yl]-2-iminoxypropionic acid,
[cyclohexyl-(4-(4-thiazolylmethoxy)phenyl)methyl]-2-iminoxy propionic acid,
[cyclohexyl-(4-(4-thiazolylmethoxy)phenyl)methyl]iminoxyacetic acid,
[cyclohexyl-(4-(2-benzothiazolylmethoxy)phenyl)methyl] iminoxy acetic acid,
[cyclohexyl-(4-(1-methyl-2-benzimidazolylmethoxy)phenyl) methyl]-2-iminoxypropionic acid,
[cyclohexyl-(4-(2-benzoxazolylmethoxy)phenyl)methyl] iminoxy acetic acid,
[cyclohexyl-(4-(4-pyridylmethoxy)phenyl)methyl]-2-iminoxypropionic acid,
[cyclohexyl-(4-(3-pyridylmethoxy)phenyl)methyl]-2-iminoxypropionic acid,
[cyclohexyl-(4-(2-pyridylmethoxy)phenyl)methyl]-2-iminoxypropionic acid,
[cyclohexyl-(4-(2-thiazolylmethoxy)phenyl)methyl]-2-iminoxypropionic acid,
[cyclohexyl-(4-(4-thiazolylmethoxy)phenyl)methyl]-2-iminoxypropionic acid,
[cyclohexyl-(4-(5-thiazolylmethoxy)phenyl)methyl]-2-iminoxypropionic acid,
[cyclohexyl-(4-(2-quinolylmethoxy)phenyl-4-phenyl)methyl]-2-iminoxypropionic acid,
[cyclohexyl-(6-(2-quinolylmethoxy)naphth-2-yl)methyl]-2-iminoxypropionic acid,
[cyclohexyl-(6-(2-quinolylmethoxy)-1,2,3,4-tetrahydronaphth-2-yl)methyl]-2-iminoxypropionic acid,
[cyclohexyl-(1-methyl-6-(2-quinolylmethoxy)indol-2-yl)methyl]-2-iminoxypropionic acid, [cycloheptyl-(6-(2-quinolylmethoxy)benzo[b]thien-2-yl)methyl]-2-iminoxypropionic acid,
[cyclohexyl-(4-(2-quinolylethyl)phenyl)methyl]-2-iminoxypropionic acid,

[cyclohexyl-(4-(2-quinolylethenyl)phenyl)methyl]-2-iminoxypropionic acid,
[cyclohexyl-(4-(2-quinolyloxymethyl)phenyl)methyl]-2-iminoxypropionic acid,
[cyclohexyl-(4-(2-quinolylthiomethyl)phenyl)methyl]-2-iminoxypropionic acid,
[cyclohexyl-(4-(2-quinolylsulfonylmethyl)phenyl)methyl]-2-iminoxypropionic acid,
[cyclohexyl-(4-(2-quinolylethynyl)phenyl)methyl]-2-iminoxypropionic acid,
[cyclohexyl-(4-(2-quinolylmethoxyethyl)phenyl)methyl]-2-iminoxypropionic acid,
[cyclohexyl-(2-(2-pyridylmethoxy)pyrid-5-yl)methyl]-2-iminoxypropionic acid,
[cyclohexyl-(5-(2-quinolylmethoxy)thien-2-yl)methyl]-2-iminoxypropionic acid,
[cyclohexyl-(2-(2-quinolylmethoxy)thien-5-yl)methyl]-2-iminoxypropionic acid,
[cyclohexyl-(6-(2-quinolylmethoxy)benzo[b]fur-2-yl)methyl]-2-iminoxypropionic acid,
[cyclopentyl-(4-(2-quinoxalylmethoxy)phenyl)methyl]-2-iminoxypropionic acid,
[cyclohexyl-(4-(thiazolo[4,5-b]pyrid-6-ylmethoxy)phenyl)methyl]-2-iminoxypropionic acid,
[cyclohexyl-(4-(thiazolo[5,4-b]pyrid-6-ylmethoxy)phenyl)methyl]-2-iminoxypropionic acid,
[cyclopentyl-(4-(2-pyrimidylmethoxy)phenyl)methyl]-2-iminoxypropionic acid,
[cyclohexyl-(4-(4-phenylthiazol-2-ylmethoxy)phenyl)methyl]-2-iminoxypropionic acid,
[cyclohexyl-(4-((4-pyrid-2-yl)thiazol-2-ylmethoxy)phenyl)methyl]-2-iminoxypropionic acid,
[phenyl-(4-(2-quinolylmethoxy)phenyl)methyl]-2-iminoxypropionic acid,
5-methylthien-2-yl-(4-(2-quinolylmethoxy)phenyl)methyl]-2-iminoxypropionic acid,
[pyrid-2-yl-(4-(2-quinolylmethoxy)phenyl)methyl]-2-iminoxypropionic acid,
[3-cyclopropylpropyl-(4-(2-quinolylmethoxy)phenyl)methyl]-2-iminoxypropionic acid,
[butyloxymethyl-(4-(2-quinolylmethoxy)phenyl)methyl]-2-iminoxypropionic acid,
[2-phenylethyl-(4-(2-quinolylmethoxy)phenyl)methyl]-2-iminoxypropionic acid,
[2-pyrid-4-ylethyl-(4-(2-quinolylmethoxy)phenyl)methyl]-2-iminoxypropionic acid,
[2-furyl-(4-(2-quinolylmethoxy)phenyl)methyl]-2-iminoxypropionic acid,
[2-thiazolyl-(4-(2-quinolylmethoxy)phenyl)methyl]-2-iminoxypropionic acid,
[4-perhydropyranyl-(4-(2-quinolylmethoxy)phenyl)methyl]-2-iminoxypropionic acid,
(R)-[cyclohexyl-(4-(2-benzothiazolylmethoxy)phenyl)methyl]iminoxy acetic acid,
(S)-[cyclohexyl-(4-(2-benzothiazolylmethoxy)phenyl)methyl]iminoxy acetic acid,
[cyclopentyl-(4-(2-benzothiazolylmethoxy)phenyl)methyl] iminoxy acetic acid.
(R)-[cyclopentyl-(4-(2-benzothiazolylmethoxy)phenyl)methyl]iminoxy acetic acid,(S)-[cyclopentyl-(4-(2-benzothiazolylmethoxy)phenyl)methyl]iminoxy acetic acid,
[2-cyclopentyl-1-(4-(4-thiazolylmethoxy)phenyl)eth-1-yl] iminoxy acetic acid,
O-[2-cyclopentyl-1-(4-(4-thiazolylmethoxy)phenyl)eth-1-yl]-4-carboxybenzaldoxime,
[2-cyclopentyl-1-(4-(4-thiazolylmethoxy)phenyl)eth-1-yl]-2-iminoxypropionic acid,
[cyclopentyl-(4-(4-thiazolylmethoxy)phenyl)methyl]-2-iminoxy propionic acid,
[cyclopentyl-(4-(4-thiazolylmethoxy)phenyl)methyl]iminoxyacetic acid,
(R)-[cyclohexyl-(4-(6-(4-fluorophenoxy)pyrid-2-ylmethoxy)phenyl)methyl] iminoxyacetic acid,
(S)-[cyclohexyl-(4-(6-(4-fluorophenoxy)pyrid-2-ylmethoxy)phenyl)methyl] iminoxyacetic acid,
[cyclopentyl-(4-(6-(4-fluorophenoxy)pyrid-2-ylmethoxy)phenyl)methyl] iminoxyacetic acid,
(R)-[cyclopentyl-(4-(6-(4-fluorophenoxy)pyrid-2-ylmethoxy)phenyl)methyl] iminoxyacetic acid,
(S)-[cyclopentyl-(4-(6-(4-fluorophenoxy)pyrid-2-ylmethoxy)phenyl)methyl] iminoxyacetic acid.
cyclohexyl-(4-(2-quinolylmethoxy)phenyl)methyl]iminoxyaceto-N-hydroxyamide,
cyclohexyl-(4-(2-quinolylmethoxy)phenyl)methyl]-2-iminoxy propionyl-N-methyl-N-hydroxyamide,
cyclohexyl-(4-(2-quinolylmethoxy)phenyl)methyl]-4-iminoxy pentanoyl-N-methyl-N-hydroxyamide,
cyclohexyl-(4-(2-quinolylmethoxy)phenyl)methyl]-2-iminoxy-3-(4-hydroxyphenyl)propionyl-N-methyl-N-hydroxyamide,
cyclohexyl-(4-(2-quinolylmethoxy)phenyl)methyl]-2-iminoxy-3-phenylpropionyl-N-methyl-N-hydroxyamide,
cyclohexyl-(4-(2-quinolylmethoxy)phenyl)methyl]-3-iminoxy-(2,2-dimethyl) propionyl-N-methyl-N-hydroxyamide,
cyclopentyl-(4-(2-quinolylmethoxy)phenyl)methyl]iminoxyaceto-N-hydroxyamide,
cyclopentyl-(4-(2-quinolylmethoxy)phenyl)methyl]-2-iminoxy propionyl-N-methyl-N-hydroxyamide,
[1,2,3,4-tetrahydro-6-(2-quinolylmethoxy)naphth-1-yl]iminoxy aceto-N-hydroxyamide,
[1,2,3,4-tetrahydro-6-(2-quinolylmethoxy)naphth-1-yl]-2-iminoxypropionyl-N-methyl-N-hydroxyamide,
[4-(4-chlorophenyl)-1-(4-(2-quinolylmethoxy)phenyl)butyl]iminoxyaceto-N-hydroxyamide,
[2-cyclohexyl-1-(4-(2-quinolylmethoxy)phenyl)eth-1-yl] iminoxyaceto-N-hydroxyamide,
[2-cyclohexyl-1-(4-(2-quinolylmethoxy)phenyl)eth-1-yl]-2-iminoxypropionyl-N-methyl-N-hydroxyamide,
[2-cyclohexyl-1-(4-(2-quinolylmethoxy)phenyl)eth-1-yl]-4-iminoxypentanoyl-N-methyl-N-hydroxyamide,
[cycloheptyl-(4-(2-quinolylmethoxy)phenyl)methyl]iminoxyaceto-N-hydroxyamide,
[3-cyclohexyl-2-[4-(2-quinolylmethoxy)phenyl)prop-1-yl] iminoxy aceto-N-hydroxyamide,
[3-cyclohexyl-2-(4-(2-quinolylmethoxy)phenyl)prop-1-yl]-2-iminoxypropionyl-N-methyl-N-hydroxyamide,
[3-cyclohexyl-2-(4-(2-quinolylmethoxy)phenyl)prop-1-yl}-3-iminoxy-(2,2-dimethyl)propionyl-N-methyl-N-hydroxyamide,
[4-(4-fluorophenyl)-1-(4-(2-quinolylmethoxy)phenyl)but-1-yl]iminoxyaceto-N-hydroxyamide,
[4-(4-fluorophenyl)-1-(4-(2-quinolylmethoxy)phenyl)but-1-yl]- 2-iminoxypropionyl-N-methyl-N-hydroxyamide,
[2-cyclohexyl-2-(4-(2-quinolylmethoxy)phenyl)eth-1-yl}iminoxyaceto-N-hydroxyamide,
[2-cycloheptyl-2-(4-(2-quinolylmethoxy)phenyl)eth-1-yl] iminoxyaceto-N-hydroxyamide,
[2-cycloheptyl-2-(4-(2-quinolylmethoxy)phenyl)eth-1-yl]-3-iminoxy- 2,2-dimethylpropionyl-N-methyl-N-hydroxyamide,
[2-cyclopentyl-2-(4-(2-quinolylmethoxy)phenyl)eth-1-yl] iminoxyaceto-N-hydroxyamide,
[cyclohexyl-(4-(2-quinolylmethoxy)phenyl)methyl]-Z-2-iminoxypropionyl-N-methyl-N-hydroxyamide,

[cyclohexyl-(4-(2-quinolylmethoxy)phenyl) methyl]-E-2-iminoxypropionyl-N-methyl-N-hydroxyamide,
(R)-[cyclohexyl-(4-(2-quinolylmethoxy)phenyl)methyl]-E-2-iminoxypropionyl-N-methyl-N-hydroxyamide,
(S)-[cyclohexyl-(4-(2-quinolylmethoxy)phenyl)methyl]-E-2-iminoxypropionyl-N-methyl-N-hydroxyamide,
[cyclohexyl-(4-(2-quinolylmethoxy)phenyl)methyl]-E-iminoxy aceto-N-hydroxyamide,
[2-phenyl-1-(4-(2-quinolylmethoxy)phenyl)eth-1-yl]-Z-2-iminoxypropionyl-N-methyl-N-hydroxyamide,
[2-phenyl-1-(4-(2-quinolylmethoxy)phenyl)eth-1-yl]-E-2-iminoxy propionyl-N-methyl-N-hydroxyamide,
[2-thienyl-(4-(2-quinolylmethoxy)phenyl)methyl]-E-2-iminoxy propionyl-N-methyl-N-hydroxyamide,
[cyclohexyl-(2-chloro-4-(2-quinolylmethoxy)phenyl)methyl]-E-2-iminoxypropionyl-N-methyl-N-hydroxyamide,
[cyclohexyl-(3-chloro-4-(2-quinolylmethoxy)phenyl)methyl]-E-2-iminoxypropionyl-N-methyl-N-hydroxyamide,
[cyclohexyl-(2-chloro-4-(2-quinolylmethoxy)phenyl)methyl]-Z-2-iminoxypropionyl-N-methyl-N-hydroxyamide,
[3-methyl-3-phenyl-1-[4-(2-quinolylmethoxy)phenyl)but-1-yl]-Z- 2-iminoxypropionyl-N-methyl-N-hydroxyamide,
[3-methyl-3-phenyl-1-(4-(2-quinolylmethoxy)phenyl)but-1-yl]-E- 2-iminoxypropionyl-N-methyl-N-hydroxyamide,
[cyclohexyl-(2-chloro-4-(2-quinolylmethoxy)phenyl)methyl]-Z-2-iminoxypropionyl-N-methyl-N-hydroxyamide,
[3-methyl-3-phenyl-1-[4-(2-quinolylmethoxy)phenyl)but-1-yl]-Z- 2-iminoxypropionyl-N-methyl-N-hydroxyamide,
[3-methyl-3-phenyl-1-(4-(2-quinolylmethoxy)phenyl)but-1-yl]-E- 2-iminoxypropionyl-N-methyl-N-hydroxyamide,
[4-(2-quinolylmethoxy)phenylpent-1-yl]-E-2-iminoxypropionyl-N-methyl-N-hydroxyamide,
[4-(2-quinolylmethoxy)phenyl)pent-1-yl]-E-iminoxyaceto-N-hydroxyamide,
[4-(2-quinolylmethoxy)phenyl)-but-3-en-1-yl]-E-iminoxy-2-propionyl-N-methyl-N-hydroxyamide,
[cyclohexyl-1-(4-(2-quinolylmethoxy)phenyl)eth-2-yl]-2-iminoxypropionyl-N-methyl-N-hydroxyamide,
[cycloheptyl-(4-(2-quinolylmethoxy)phenyl)eth-2-yl]-2-iminoxypropionyl-N-methyl-N-hydroxyamide,
[2-chloro-(4-(2-quinolylmethoxy)phenyl)methyl]-2-iminoxypropionyl-N-methyl-N-hydroxyamide,
[cycloheptyl-(4-(2-quinolylmethoxy)phenyl)methyl]-2-iminoxypropionyl-N-methyl-N-hydroxyamide,
(R)-[cyclopentyl-(4-(2-quinolylmethoxy)phenyl)methyl]-E-2-iminoxypropionyl-N-methyl-N-hydroxyamide,
(S)-[cyclopentyl-(4-(2-quinolylmethoxy)phenyl)methyl]-E-2-iminoxypropionyl-N-methyl-N-hydroxyamide,
[cyclohexyl-(4-(2-quinolylmethoxy)benzo[b]thien-2-yl)methyl]-2-iminoxypropionyl-N-methyl-N-hydroxyamide,
[cyclohexyl-(6-(2-quinolylmethoxy)pyrid-3-yl)methyl]iminoxy aceto-N-hydroxyamide,
[cyclohexyl-(4-(6-(4-fluorophenoxy)pyrid-2-ylmethoxy)phenyl)methyl] iminoxyaceto-N-hydroxyamide,
[2-cyclohexyl-1-(4-(4-thiazolylmethoxy)phenyl)eth-1-yl] iminoxyaceto-N-hydroxyamide,
[2-cyclohexyl-1-(4-(4-thiazolylmethoxy)phenyl)eth-1-yl]-2-iminoxypropionyl-N-methyl-N-hydroxyamide,
[cyclohexyl-(4-(4-thiazolylmethoxy)phenyl)methyl]-2-iminoxy propionyl-N-methyl-N-hydroxyamide,
[cyclohexyl-(4-(4-thiazolylmethoxy)phenyl)methyl]iminoxyaceto-N-hydroxyamide,
[cyclohexyl-(4-(2-benzothiazolylmethoxy)phenyl)methyl] iminoxyaceto-N-hydroxyamide,
[cyclohexyl-(4-(1-methyl-2-benzimidazolylmethoxy)phenyl)methyl]-2-iminoxypropionyl-N-methyl-N-hydroxyamide, and
[cyclohexyl-(4-(2-benzoxazolylmethoxy)phenyl)methyl] iminoxyaceto-N-hydroxyamide.

In one preferred embodiment, compounds of this invention have the formula shown above wherein W is pyridyl, or pyridyl substituted with halogen, alkyl of one to six carbon atoms, alkoxy of one to six carbon atoms, phenoxy, or phenoxy substituted with halogen, alkyl of one to six carbon atoms, or alkoxy of one to six carbon atoms, X is methylene, Q is —O—, and Y is phenyl.

In another preferred embodiment, compounds of this invention have the formula shown above wherein W is thiazolyl, or thiazolyl substituted with halogen, alkyl of one to six carbon atoms, alkoxy of one to six carbon atoms, phenyl, phenyl substituted with halogen, alkyl of one to six carbon atoms, or alkoxy of one to six carbon atoms, pyridyl, or pyridyl substituted with halogen, alkyl of one to six carbon atoms, or alkoxy of one to six carbon atoms.

In yet another preferred embodiment, compounds of this invention have the formula shown above wherein W is benzothiazolyl, or benzothiazolyl substituted with halogen, alkyl of one to six carbon atoms, or alkoxy of one to six carbon atoms, X is methylene, Q is —O—, and Y is phenyl.

In a more preferred embodiment, compounds of the present invention have the formula indicated above wherein W is quinolyl, or quinolyl substituted with halogen, alkyl of one to six carbon atoms, or alkoxy of one to six carbon atoms.

In a still more preferred embodiment, compounds of the present invention have the formula indicated above wherein W is quinolyl, or quinolyl substituted with halogen, alkyl of one to six carbon atoms, or alkoxy of one to six carbon atoms, X is methylene, Q is —O—, and Y is phenyl.

The most preferred compounds of the present invention are selected from the group consisting of
[cyclohexyl-(4-(2-quinolylmethoxy)phenyl)methyl]iminoxyacetic acid,
[cyclohexyl-(4-(2-quinolyl-methoxy)phenyl)methyl]-2-iminoxypropionic acid,
(R)-[Cyclohexyl-(4-(2-quinolyl-methoxy)phenyl)methyl]-2-iminoxypropionic acid,
(S)-[cyclohexyl-(4-(2-quinolyl-methoxy)phenyl)methyl]-2-iminoxypropionic acid,
[cyclopentyl-(4-(2-quinolylmethoxy)phenyl)methyl]iminoxyacetic acid,
[cyclopentyl-(4-(2-quinolylmethoxy)phenyl)methyl]-2-iminoxypropionic acid,
(R)-[cyclopentyl-(4-(2-quinolylmethoxy)phenyl)methyl]-2-iminoxypropionic acid,
(S)-[cyclopentyl-(4-(2-quinolylmethoxy)phenyl)methyl]-2-iminoxypropionic acid,
[2-cyclohexyl-1-(4-(2-quinolylmethoxy)phenyl)ethyl]iminoxyacetic acid, and
[cyclohexyl-(4-(2-benzothiazolylmethoxy)phenyl)methyl] iminoxy acetic acid,
or a pharmaceutically acceptable salt thereof.

Lipoxygenase Inhibition Determination

Inhibition of leukotriene biosynthesis was evaluated in an assay involving calcium ionophore-induced $LTB_4$ expressed in human polymorphornuclear leukocytes (PMNL). Human PMNL isolated from heparinized (20 USP units/mL) venous blood (25 mL) obtained from healthy volunteers was layered over an equal volume of Ficoll-Hypaque Mono-Poly Resolving Medium (ICN Flow, Costa Mesa, Calif.) and centrifugated at 400 x g for 40 min at 20° C. The PMNL was collected, erythrocytes lysed and washed 2x and suspended at $1.0 \times 10^7$ cells/mL in Earle's balanced salt solution with 17 mM Earle's HEPES. Aliquots of the cell suspension were preincubated with test compounds dissolved in DMSO (final concentration <2%) for 15 min. and stimulated with calcium ionophore (final concentration 8.3 μM) for 10 min. at 37° C. Incubations were stopped with the addition of two volumes of ice-cold methanol followed by centrifuging the cell suspensions at 4° C. for 10 min at 450 x g. The mount of $LTB_4$ in the methanol extract was analyzed by enzyme-linked immunoassay or by HPLC analysis.

The compounds of this invention inhibit leukotriene biosynthesis as shown by the data for representative examples in Table 1.

TABLE 1

In Vitro Inhibitory Potencies Against 5-Lipoxygenase from Stimulated $LTB_4$ Formation in Human Polymorphonuclear Leukocytes

| Example | $IC_{50}$ (μM) |
| --- | --- |
| 1 | 0.021 |
| 2 | 0.004 |
| 6 | 0.032 |
| 12 | 0.055 |
| 14 | 0.004 |
| 15 | 0.006 |
| 26 | 0.005 |
| 27 | 0.008 |
| 28 | 0.005 |
| 30 | 0.170 |
| 31 | 0.025 |
| 32 | 0.170 |
| 33 | 0.015 |
| 34 | 0.470 |
| 35 | 0.070 |
| 36 | 0.050 |
| 37 | 0.006 |
| 40 | 0.017 |
| 42 | <0.1 |
| 43 | <0.1 |
| 44 | <0.1 |
| 45 | <0.1 |
| 48 | <0.1 |
| 49 | <0.1 |
| 50 | <0.1 |
| 51 | <0.1 |
| 55 | 0.030 |
| 57 | <0.1 |
| 58 | <0.1 |
| 62 | 0.036 |

Inhibition of the biosynthesis of leuktrienes in vivo after oral administration of compound was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group.

TABLE 2

In Vivo Leukotriene Inhibition in Rat Peritoneal Anaphylaxis Model

| Example | % Inhibition (dose) or $ED_{50}$ |
| --- | --- |
| 1 | 82% at 30 μmol/kg |
| 2 | 1.2 mg/kg |
| 19 | 81% at 30 μmol/kg |
| 27 | 0.7 mg/kg |

Pleural inflammation was induced in male rats following the method of Rao et al (Rao, T. S., Currie, J. L., Shaffer, A. F., Isakson, P. C., (1993) Evaluation of 5-lipoxygenase Inhibitors, Zileuton, A-78773 and ICI D-2138 in an Ionophore (A- 23 187) Induced Pleural Inflammation Model in the Rat. Life Sciences, 53: 147). Rats were dosed with experimental compounds in 0.2% methocel one hour prior to the intrapleural injection of the calcium ionophore, A23 187. The rats where lightly anesthetized with Pentrane (Abbott Laboratories) and injected intrapleurally with 0.5 ml of 2% ethanol in injectable saline (Abbott Laboratories) containing 20 ug of A23187 (Cal BioChem-Novabiochem). Thirty minutes later the animals were euthanised and the pleural cavities lavaged with ice cold saline (Abbott Laboratories). The lavage fluid was then added to ice cold methanol (final methanol concentration 30%) to lyse cells and precipitate protein. Eicosanoids were determined by enzyme immunoassay by standard methods.

TABLE 3

In Vivo Leukotriene Inhibition in Rat Pleural Inflammation

| Example | % Inhibition (dose) or $ED_{50}$ |
| --- | --- |
| 2 | 89% at 30 μmol/kg |
| 45 | 1.2 mg/kg |
| 48 | 2.0 mg/kg |

Pharmaceutical Compositions

The present invention also provides pharmaceutical compositions which comprise compounds of the present invention formulated together with one or more non-toxic pharmaceutically acceptable careers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraanicular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may conch inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agaragar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono-or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The oxime carboxylate compounds of this invention can be prepared by several procedures and representative methods are outlined in Scheme 1. Scheme 1 describes a general procedure involving treatment of the requisite aldehyde 1 (where W, X, Q and Y are groups as previously defined) with a Grignard intermediate (where Hal is halogen and R1 is as previously described) to provide the hydroxy intermediate 2. This intermediate is treated with N-hydroxyphthalimide, triphenylphosphine and diethylazodicarboxylate (DEAD) to form a N-phthaloyl intermediate which is subsequently treated hydrazine hydrate to provide the desired O-alkylhydroxylamine intermediate 3. This intermediate is reacted with an oxoalkylcarboxylate (where R2 and A are groups as defined previously) to provide the desired compounds.

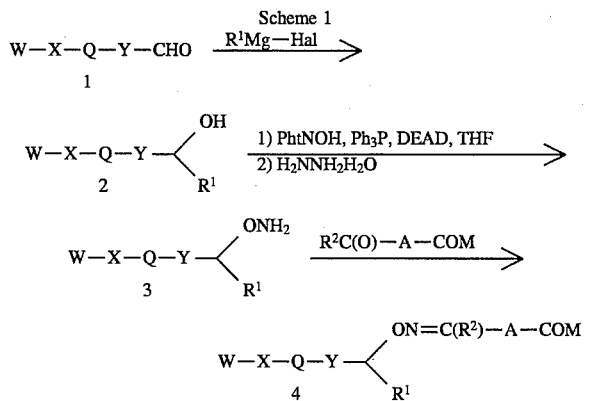

The foregoing may be better understood by reference to the following examples which are provided for illustration and not intended to limit the scope of the inventive concept. The following abbreviations are used: THF for tetrahydrofuran, n-BuLi for n-butyllithium, DCC for dicyclohexyl carbodiimide, DEAD for diethyl azodicarboxylate, DMF for N,N-dimethylformamide, DIAD for diisopropyl azodicarboxylate, CDCl$_3$ for deuterochloroform, DMSO-d$_6$ for deuterodimethylsulfoxide, DIBAL for diisobutylaluminum hydride, LAH for lithium aluminum hydride, LDA for lithium diisopropylamide and TDA-1 for tris[2-(2-methoxyethoxy)ethyl] amine.

EXAMPLE 1

Preparation of
[Cyclohexyl-(4-(2-quinolylmethoxy)phenyl)methyl]-iminoxyacetic acid

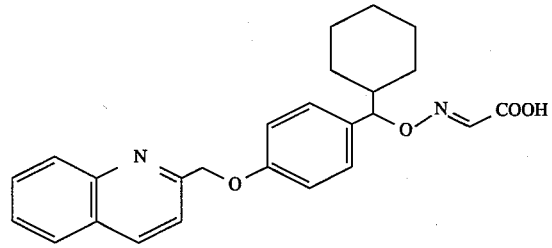

Step 1: 4-(2-quinolylmethoxy)benzaldehyde.

To a solution of 4-hydroxybenzaldehyde (3.66 g, 30 mmol) and potassium carbonate (8.24 g, 60 mmol) in DMF (75 mL) was added 2-chloromethylquinoline hydrochloride (6.42 g, 30 mmol), and the resulting solution was stirred at ambient temperature for 16 hours. The reaction mixture was then poured into water (100 mL) and extracted with ethyl acetate (100 mL). The extract was dried over MgSO$_4$ and concentrated in vacuo. The residue was chromatographed on silica gel eluting with 2:1 hexane-ethyl acetate to afford 4-(2-quinolylmethoxy)benzaldehyde (5.8 g, 74%) as a crystalline compound.

Step 2: {Cyclohexyl-[4-(2-quinolylmethoxy)phenyl]}methanol.

To a solution of 4-(2-quinolylmethoxy)benzaldehyde (2.63 g, 10 mmol), prepared as in step 1, in THF (50 mL) at −78° C. was added cyclohexylmagnesium chloride (10 mL of a 2M solution in THF, 20 mmol). The resulting mixture was stirred at ambient temperature for 12 hours and then quenched with aqueous saturated NH$_4$Cl (25 mL) and the THF was removed in vacuo. To the residue was added water (50 mL) and the product was extracted with ethyl acetate (100 mL). The extract was dried over MgSO$_4$ and concentrated in vacuo. The residue was purified by column chromatography eluting with 9:1 methylene chloride-ethyl acetate to afford 3.3 g (94%) of {Cyclohexyl-[4-(2-quinolylmethoxy)phenyl]}methanol.

Step 3: N-Phthaloyl-O-{cyclohexyl-[4-(2-quinolylmethoxy)-phenyl]}methylhydroxylamine.

To a mixture of the {Cyclohexyl-[4-(2-quinolylmethoxy)phenyl]}methanol, prepared in step 2, triphenylphosphine (3.93 g, 15 mmol) and N-hydroxyphthalimide (1.55 g, 9.5 mmol) in THF (100 mL) was added dropwise a solution of DEAD (2.4 mL; 15 mmol) in THF (15 mL). The mixture was then stirred at ambient temperature for 14 hours, concentrated in vacuo, and the residue obtained was chromatographed on silica gel eluting with 2:1 hexane-ethyl acetate to provide N-Phthaloyl-O-{ cyclohexyl-[4-(2-quinolylmethoxy)phenyl]}methylhydroxylamine as an oil (5.0 g).

Step 4: O-{Cyclohexyl-[4-(2-quinolylmethoxy)phenyl]}methylhydroxylamine.

A solution of the N-Phthaloyl-O-{cyclohexyl-[4-(2-quinolylmethoxy)phenyl] }methylhydroxylamine prepared in step 3 and hydrazine hydrate (1.5 mL, 30 mmol) in 1:1 ethanol-methylene chloride (80 mL) was refluxed for 30 minutes and then cooled to ambient temperature. 10% Sodium carbonate (50 mL) was added, and the mixture was extracted with ethyl acetate (120 mL). The extract was washed with water (2×50 mL) and brine, dried over MgSO$_4$, and concentrated in vacuo to provide 3.11 g of O-{Cyclohexyl-[4-(2-quinolylmethoxy)phenyl] }methylhydroxylamine.

Step 5: {Cyclohexyl-[4-(2-quinolylmethoxy)phenyl]methyl}-iminoxyacetic acid.

A mixture of the O-{Cyclohexyl-[4-(2-quinolylmethoxy)phenyl] }methylhydroxylamine from Step 4 (543 mg, 1.5 mmol), glyoxylic acid hydrate (140 mg, 1.5 mmol), acetic acid (0.09 mL, 1.5 mmol) and sodium acetate trihydrate (207 mg, 1.5 mmol) in methanol (25 mL)-dioxane (10 mL)-water (5 mL) was stirred at ambient temperature for 48 hours. The organics were removed in vacuo, and water (25 mL) and 1N sodium hydroxide (4 mL) were added. The insoluble material was extracted with ethyl ether (2×25 mL), and the aqueous solution was acidified to pH 3 with 10% citric acid. The precipitated solid was filtered and recrystallized from ethyl acetate-hexane to afford 400 mg (64%) of {Cyclohexyl-[4-(2-quinolylmethoxy)phenyl]methyl}-iminoxyacetic acid. m.p. 199°–200° C. $^1$H NMR (300 MHz, DMSO-d$_6$) δ 1.1 (m, 5H), 1.3 (m, 1H), 1.7 (m, 4H), 1.9 (m, 1H), 4.9 (d, J=7 Hz, 1H), 5.38 (s, 2H), 7.05 (d, J=9 Hz, 2H), 7.2 (d, J=9 Hz, 2H), 7.56 (s, 1H), 7.62 (t, J=8 Hz, 1H), 7.7 (d, J=8 Hz, 1H,), 7.8 (m, 1H), 8.0 (t, J=8 Hz, 2H), 8.43 (d, J=8 Hz, 1H). MS (DCI/NH$_3$) m/e 419 (M+H)$^+$. IR (KBr): 3450, 1700, 1605 cm$^{-1}$. Analysis calcd. for C$_{25}$H$_{26}$N$_2$O$_4$: C, 71.75; H, 6.26; N, 6.69; Found: C, 71.42; H, 6.25; N, 6.45.

EXAMPLE 2

Preparation of
[Cyclohexyl-(4-(2-quinolylmethoxy)phenyl)methyl]-2-iminoxy propionic acid Step 1: Cyclohexyl-[4-(2-quinolylmethoxy)phenyl]methyl}-iminoxy-2-propionic acid methyl ester.

A mixture of O-{cyclohexyl-[4-(2-quinolylmethoxy)phenyl]methyl}-hydroxylamine (543 mg, 1.5 mmol), prepared as in Example 1, step 4, methyl pyruvate (0.14 mL, 1.5 mmol) and acetic acid (0.09 mL, 1.5 mmol) in methanol (25 mL)-dioxane (10 mL) and water (5 mL) was stirred at ambient temperature for 24 hours. After the organic solvents were removed in vacuo, water (25 mL) was added to the residue. The resulting mixture was extracted with ethyl acetate, dried with MgSO$_4$ and concentrated in vacuo. The residue was chromatographed on silica gel eluting with 3:1 hexane-ethyl acetate to afford 300 mg of Cyclohexyl-[4-(2-quinolylmethoxy)phenyl] methyl}-iminoxy-2-propionic acid methyl ester as an oil.

Step 2: Cyclohexyl-[4-(2-quinolylmethoxy)phenyl]methyl }-iminoxy-2-propionic acid.

To a solution of the Cyclohexyl-[4-(2-quinolylmethoxy)phenyl]methyl}-iminoxy- 2-propionic acid methyl ester from step 1 in 2:1 methanol-dioxane (30 mL) was added 1N sodium hydroxide (2 mL), and the resulting mixture was refluxed at 50° C. for 30 minutes. The organics were then removed in vacuo, and water (25 mL) was added to the residue. The aqueous solution was washed with ethyl ether (25 mL) and then acidified with 50% citric acid. The solid obtained was filtered, dried in vacuo and and recrystallized from ethyl acetate-hexane to provide 210 mg of Cyclohexyl-[4-(2-quinolylmethoxy)phenyl]methyl}-iminoxy-2-propionic acid as a mixture of E and Z isomers. m.p. 185°–186° C. $^1$H NMR (300 MHz, DMSO-d$_6$) δ 1.1 (m, 5H), 1.33 (m, 1H), 1.7 (m, 4H), 1.9 (m, 1H), 2.0 (s, 3H), 4.92 (d, J= 7Hz, 1H), 5.36 (s, 2H), 7.03 (d, J=9 Hz, 2H), 7.2 (d, J=9Hz, 2H), 7.62 (m, 1H), 7.7 (d, J=9 Hz, 1H), 7.8 (m, 1H), 8.0 (t, J=9 Hz, 2H), 8.43 (d, J=9 Hz, 1H), 12.95 (br. s, 1H). MS (DCI/NH$_3$) m/e 433 (M+H)$^+$. IR (CDCl$_3$): 3420,1750, 1610 cm$^{-1}$. Analysis calcd. for C$_{26}$H$_{28}$N$_2$O$_4$: C, 72.20; H, 6.53; N, 6.48. Found: C, 71.99; H, 6.42; N, 6.21.

EXAMPLE 3

Preparation of
[Cyclohexyl-(4-(2-quinolylmethoxy)phenyl)methyl]-4-iminoxy pentanoic acid The title compound was prepared according to the procedure of Example 1, except substituting levulinic acid (4-oxo-pentanoic acid) for glyoxylic acid. $^1$H NMR (300 MHz, DMSO-d$_6$) δ 1.1 (m, 5H), 1.35 (m, 1H), 1.6 (m, 4H), 1.8 (m , 5H), 2.3 (s, 3H), 4.68 (d, J=7 Hz, 1H), 5.33 (s, 2H), 7.0 (d, J=9 Hz, 2H), 7.13 (d, J=9 Hz, 2H), 7.53 (m, 1H), 7.68 (d, J=9 Hz, 1H), 7.8 (m, 1H), 8.0 (t, J=9 Hz, 2H), 8.43 (d, J=9 Hz, 1H). MS (DCI/NH$_3$) m/e 461 (M+H)$^+$. IR (CDCl$_3$): 3480, 1710 with shoulder 1740,1605 cm$^{-1}$. Analysis calcd for C$_{28}$H$_{32}$N$_2$O$_4$.H$_2$O: C, 70.27; H, 7.16; N, 5.85. Found: C,70.81; H, 7.17; N, 6.18.

EXAMPLE 4

Preparation of
[Cyclohexyl-(4-(2-quinolylmethoxy)phenyl)methyl]-2-iminoxy-3-( 4-hydroxyphenyl)propionic acid The title compound was prepared according to the procedure of Example 1, except substituting 3-(4-hydroxyphenyl)-2-oxo-propionic acid for glyoxylic acid. $^1$H NMR (300 MHz, DMSO-d$_6$) δ 1.1 (m, 5H), 1.35 (m, 1H), 1.6 (m, 4H), 1.8 (m, 1H), 7.73 (two d, J=12 Hz, 2H), 4.62 and 4.85 (two d, 1:4, J=7 Hz, 1H), 5.35 (two s, 4:1, 2H), 6.56 (two d, 1:4, J=9 Hz, 2H), 7.0 (m, 6H), 7.65 (m, 2H), 7.8 (m, 1H), 8.0 (t, J=8 Hz, 2H), 8.43 (d, J=8 Hz, 1H), 9.15 (br. s, 1H). MS (DCI/NH$_3$) m/e 525 (M+H)$^+$. IR (KBr): 3440, 1710, 1610 cm$^{-1}$.

EXAMPLE 5

Preparation of
[Cyclohexyl-(4-(2-quinolylmethoxy)phenyl)methyl]-2-iminoxy-3-phenylpropionic acid The desired material was prepared according to the procedure of Example 1, except substituting 2-oxo-3-(phenyl)propionic acid for glyoxylic acid. m.p. 92°– 95° C. $^1$H NMR (300 MHz, DMSO-d$_6$) δ 1.0 (m, 5H), 1.3 (m, 1H), 1.6 (m, 5H), 3.85 (m, 2H), 4.62 and 4.84 (two d, 5:1, J=7 Hz, 1H), 5.35 (two s, 5:1, 2H), 7.0 (m, 5H), 7.25 (m, 3H), 7.65 (m, 2H), 7.8 (m, 1H), 8.0 (t, J=8 Hz, 2H), 8.43 (d, J=8 Hz, 1H). MS (DCI/NH$_3$) m/e 509 (M+H)$^+$, 1036 (2M+H+NH$_3$)$^+$. IR (CDCl$_3$): 3430,1750,1610 cm$^{-1}$. Analysis calcd. for C$_{32}$H$_{32}$N$_2$O$_4$: C, 72.98; H, 6.51; N, 5.32. Found C, 72.87; H, 5.84; N, 4.97.

EXAMPLE 6

Preparation of
O-[Cyclohexyl-(4-(2-quinolylmethoxy)phenyl)methyl]-4-carboxybenzaldoxime The desired material was prepared according to the procedure of Example 1, except substituting 4-carboxybenzaldehyde for glyoxylic acid. m.p. 174°–175° C. $^1$H NMR (300 MHz, DMSO-d$_6$) δ 1.1 (m, 5H), 1.35 (m, 1H), 1.7 (m, 4H), 1.95 (m, 1H), 4.9 (d, J=7 Hz, 1H), 5.35 (s, 2H), 7.04 (d, J=8 Hz, 2H), 7.22 (d, J=8 Hz), 2H), 7.65 (m, 4H), 7.8 (m, 1H), 7.9 (d, J=8 Hz, 2H), 8.0 (m, 2H), 8.36 (s, 1H), 8.41 (d, J=8 Hz, 1H), 13.05 (broad s, 1H). MS (DCI/NH$_3$) m/e 495 (M+H)$^+$. IR (KBr): 3440, 1695, 1600 cm$^{-1}$. Analysis calcd. for C$_{31}$H$_{30}$N$_2$O$_4$: C, 75.28; H, 6.11; N, 5.66. Found: C, 74.99; H, 6.09; N, 5.62.

EXAMPLE 7

Preparation of [Cyclohexyl-(4-(2-quinolylmethoxy)phenyl)methyl]-3-iminoxy-(2,2-dimethyl)propionic acid The desired material was prepared according to the procedure of Example 2, except substituting the monoaldehyde-monomethyl ester of (2,2-dimethyl)malonic acid for methyl pyruvate. $^1$H NMR (300 MHz, DMSO-d$_6$) δ 0.9 (m, 1H), 1.07 (m+ two s, 9H), 1.3 (m, 2H), 1.62 (m, 4H), 1.85 (m, 1H), 4.67 (d, J=7 Hz, 1H), 5.33 (s, 2H), 7.0 (d, J=9 Hz, 2H), 7.13 (d, J=9 Hz, 2H), 7.62 (m, 2H), 7.69 (d, J=8 Hz, 1H), 8.0 (t, J=8 Hz, 2H), 8.42 (d, J=8 Hz, 1H). MS (DCI/NH$_3$) m/e 461 (M+H)$^+$. IR (CDCl$_3$): 3400, 1670, 1600 cm$^{-1}$.

EXAMPLE 8

Preparation of [Cyclopentyl-(4-(2-quinolylmethoxy)phenyl)methyl]-iminoxy acetic acid The desired material was prepared according to the procedure of Example 1, except substituting cyclopentyl magnesium chloride for cyclohexylmagnesium chloride. m.p. 187°–188° C. (after crystallization from CH$_2$Cl$_2$-ethyl ether-hexane). $^1$H NMR (300 MHz, DMSO-d$_6$) δ 1.12 (m, 1H), 1.3 (m, 1H), 1.5 (m, 5H), 1.8 (m, 1H), 2.32 (m, 1H), 4.92 (d, J=7 Hz, 1H), 5.36 (s, 2H), 7.04 (d, J=9 Hz, 2H), 7.26 (d, J=9 Hz, 2H), 7.54 (s, 1H), 7.61 (m, 1H), 7.7 (d, J=8 Hz, 1H), 7.8 (m, 1H), 8.0 (t, J=8 Hz, 2H), 8.42 (d, J=8 Hz, 1H). MS (DCI/NH$_3$) m/e 405 (M+H)$^+$. IR (KBr): 3450,1700,1610 cm$^{-1}$. Analysis calcd. for C$_{24}$H$_{24}$N$_2$O$_4$: C, 71.27; H, 5.98; N, 6.93. Found: C, 70.99; H, 6.08; N, 6.87.

EXAMPLE 9

Preparation of [Cyclopentyl-(4-(2-quinolylmethoxy)phenyl)methyl]-2-iminoxy propionic acid The desired material was prepared according to the procedure of Example 2, except substituting cyclopentyl magnesium chloride for cyclohexyl magnesium chloride. $^1$H NMR (300 MHz, DMSO-d$_6$) δ 1.18 (m, 1H), 1.3 (m, 1H), 1.5 (m, 5H), 1.75 (m, 1H), 1.96 (s, 3H), 2.33 (m, 1H), 4.95 (d, J=7 Hz, 1H), 5.36 (s, 2H), 7.03 (d, J=9 Hz, 2H), 7.25 (d, J=9 Hz, 2H), 7.63 (m, 1H), 7.7 (d, J=8 Hz, 1H), 7.8 (m, 1H), 8.0 (t, J=8 Hz, 2H), 8.42 (d, J=8 Hz, 1H), 12.9 (broad s, 1H). MS (DCI/NH$_3$) m/e 419 (M+H)$^+$. IR (CDCl$_3$): 3400, 1760, 1705 cm$^{-1}$. Analysis calcd. for C$_{25}$H$_{26}$N$_2$O$_4$: C, 71.75; H, 6.26; N, 6.69. Found: C, 71.76; H, 6.04; N, 6.60.

EXAMPLE 10

Preparation of [1,2,3,4-Tetrahydro-6-(2-quinolylmethoxy)naphth-1-yl]iminoxy acetic acid Step 1: 6-hydroxytetralone.

A mixture of 6-methoxytetralone (8.8 g, 50 mmol) and 48% hydrobromic acid (25 mL) in acetic acid (25 mL) was refluxed at 125° C. for 3 hours. The mixture was then poured into ice/water and extracted with ethyl acetate (125 mL). The extract was washed with water and brine, dried over MgSO$_4$, and concentrated in vacuo. To the residue was added CH$_2$Cl$_2$ (25 mL), and the suspension was cooled at 0° C. for 2 hours. The solid was filtered and washed with cold CH$_2$Cl$_2$ to afford 5.8 g of 6-hydroxytetralone.

Step 2: 3,4-Dihydro-6-(2-quinolylmethoxy)-1(2H)-naphthalenone.

To a mixture of 6-hydroxytetralone, prepared as in step 1, (2.43 g, 15 mmol) and potassium carbonate (2.76 g, 20 mmol) in DMF (65 mL) was added chloromethylquinoline hydrochloride (3.42 g, 16 mmol), and the resulting mixture was stirred at ambient temperature for 24 hours. The reaction mixture was then poured into water (100 mL) and extracted with ethyl acetate (100 mL). The extract was dried with MgSO$_4$ and concentrated in vacuo. The residue was chromatographed on silica gel eluting with 5:1 methylene chloride-ethyl acetate to provide 2.3 g 3,4-Dihydro- 6-(2-quinolylmethoxy)-1(2H)-naphthalenone.

Step 3: 1,2,3,4-Tetrahydro-6-(2-quinolylmethoxy)-1-naphthalenol.

A mixture of 3,4-dihydro-6-(2-quinolylmethoxy)-1(2H)-naphthalenone (1.82 g, 6 mmol), prepared as in step 2, and sodium borohydride (230 mg, 6 mmol) in ethanol (15 mL) was refluxed for 30 minutes. The reaction was allowed to warm to ambient temperature and was then quenched with saturated NH$_4$Cl. Extraction with ethyl acetate and purification on a silica gel column eluting with 9:1 CH$_2$Cl$_2$-ethyl acetate afforded 1.79 g of 1,2,3,4-tetrahydro-6-(2-quinolylmethoxy)-1-naphthalenol.

Step 4: N-phthaloyl-O-(1,2,3,4-tetrahydro-6-(2-quinolylmethoxy)-1-naphthyl)hydroxylamine.

To a solution of 1,2,3,4-tetrahydro-6-(2-quinolylmethoxy)-1-naphthalenol (1.41 g, 4.6 mmol), prepared as in step 3, N-hydroxyphthalimide (750 mg, 4.6 mmol) and triphenylphosphine (1.83 g, 7 mmol) in THF (90 mL) at ambient temperature was added dropwise a solution of DEAD (1.12 mL, 7 mmol) in THF (10 mL). The resulting solution was stirred at ambient temperature for 10 hours and then concentrated in vacuo. The residue was chromatographed on silica gel eluting with 19:1 CH$_2$Cl$_2$-ethyl acetate to afford 1.85 g of N-phthaloyl-O-(1,2,3,4-tetrahydro-6-(2-quinolyl-methoxy)-1-naphthyl)hydroxylamine.

Step 5: O-[1,2,3,4-tetrahydro-6-(2-quinolylmethoxy)-1-naphthyl]hydroxylamine.

A mixture of the N-phthaloyl-O-(1,2,3,4-tetrahydro-6-(2-quinolyl-methoxy)- 1-naphthyl)hydroxylamine prepared in step 4 and hydrazine hydrate (0.5 mL, 10 mmol) in 2:1 ethanol-dioxane (45 mL) was refluxed for 30 minutes and then was allowed to cool to ambient temperature. 10% Sodium carbonate (10 mL) was added and the resulting mixture was extracted with ethyl acetate (100 mL). The extract was washed with water and brine, dried over MgSO$_4$ and concentrated in vacuo. The residue was chromatographed on silica gel eluting with ethyl acetate to afford 510 mg of O-[1,2,3,4-tetrahydro-6-(2-quinolylmethoxy)-1-naphthyl]hydroxylamine.

Step 6: [1,2,3,4-tetrahydro-6-(2-quinolylmethoxy)-1-naphthyl]iminoxyacetic acid.

A solution of the O-[1,2,3,4-tetrahydro-6-(2-quinolyl-methoxy)-1naphthyl] hydroxylamine prepared in Step 5 (260 mg, 0.8 mmol), glyoxylic acid hydrate (184 mg, 2 mmol), acetic acid (0.06 mL, 1 mmol) and sodium acetate (276 mg, 2 mmol) in methanol (30 mL)-dioxane (10 mL)-water (5 mL) was stirred at ambient temperature for 12 hours, and then concentrated in vacuo. To the residue was added 1N NaOH (3 mL) and water (10 mL), and the mixture was washed with ethyl ether (10 mL). The aqueous solution was acidified with 10% citric acid to pH 3 and the precipitated solid was filtered. Recrystallization from ethyl ether-hexane provided 300 mg of [1,2,3,4-tetrahydro-6-(2-quinolylmethoxy)-1-naphthyl] iminoxyacetic acid. m.p. 99°–101° C. $^1$H NMR (300 MHz, DMSO-$d_6$) δ 1.7 (m, 2H), 1.87 (m, 1H), 2.12 (m, 1H), 2.7 (m, 2H), 5.25 (t, J=2 Hz, 1H), 5.38 (s, 2H), 6.9 (m, 2H), 7.25 (d, J=9 Hz, 1H), 7.53 (s, 1H), 7.65 (m, 2H, 7.8 (m, 1H), 8.0 (t, J=8 Hz, 2H), 8.4 (d, J=8 Hz, 1H). MS (DCI/NH$_3$) m/e 377 (M+H)$^+$. IR (KBr): 3450, 1710, 1605 cm$^{-1}$. Analysis calcd. for $C_{22}H_{20}N_2O_4$: C, 70.20; H, 5.36; N, 7.44. Found: C, 69.47; H, 5.48; N, 7.44.

EXAMPLE 11

Preparation of
[1,2,3,4-Tetrahydro-6-(2-quinolylmethoxy)naphth-1-yl]-2-iminoxypropionic acid Step 1: [1,2,3,4-Tetrahydro-6-(2-quinolylmethoxy)naphth-1-yl]-2-iminoxypropionic acid methyl ester.

A mixture O-(1,2,3,4-tetrahydro-6-(2-quinolylmethoxy)naphth-1-yl) hydroxylamine (160 mg, 0.5 mmol), prepared as in Example 10, step 5, methyl pyruvate (104 mg, 1 mmol) and acetic acid (0.05 mL, 1 mmol) in methanol (25 mL)-dioxane (10 mL) was stirred at ambient temperature for 24 hours and then concentrated in vacuo. To the residue was added water (20 mL), and the product was extracted with ethyl acetate (75 mL). The extract was concentrated in vacuo and the residue was chromatographed on silica gel eluting with 3:1 hexane-ethyl acetate to afford 200 mg of 2-(1,2,3,4-tetrahydro-6-(2-quinolylmethoxy)-1-naphthyl)imnoxypropionic acid methyl ester.

Step 2: [1,2,3,4-Tetrahydro-6-(2-quinolylmethoxy)naphth-1-yl]-2-iminoxypropionic acid.

To a solution of the 2-(1,2,3,4-tetrahydro-6-(2-quinolylmethoxy)-1-naphthyl)imnoxypropionic acid methyl ester prepared in step 1 in methanol (25 mL) was added 1N NaOH (2 mL), and the resulting mixture was refluxed at 50° C. for 30 minutes. The methanol was removed in vacuo, and 25 mL of water was added to the residue. The resulting aqueous solution was washed with ethyl ether (25 mL) and acidified to pH 3 with 10% citric acid. The precipitated solid was filtered and recrystallized from ethyl ether-hexane to provide 120 mg of [1,2,3,4-Tetrahydro-6-( 2-quinolylmethoxy)naphth-1-yl]-2-iminoxypropionic acid. m.p. 83°–85° C. $^1$H NMR (300 MHz, DMSO-$d_6$) δ 1.7 (m, 2H), 1.87 (m+s, 4H), 2.1 (m, 1H), 2.7 (m, 2H), 5.24 (t, J=2 Hz, 1H), 5.37 (s, 2H), 6.9 (m, 2H), 7.3 (d, J=9 Hz, 1H), 7.63 (m, 2H), 7.8 (m, 1H), 8.0 (t, J=8 Hz, 2H), 8.42 (d, J=8 Hz, 1H). MS (DCI/NH$_3$) m/e 391 (M+H)$^+$. IR (CDCl$_3$): 3420, 1760, 1600 cm$^{-1}$. Analysis calcd. for $C_{23}H_{22}N_2O_4$: C, 70.75; H, 5.68; N, 7.17. Found: C, 70.20; H, 5.47; N, 7.00.

EXAMPLE 12

Preparation of
[4-(4-Chlorophenyl)-1-(4-(2-quinolylmethoxy)phenyl) butyl]iminoxyacetic acid Step 1: 4-(4-Chlorophenyl)-1-[4-(2-quinolylmethoxy)phenyl]butan-1-ol.

A suspension of magnesium turnings (264 mg, 11 mmol) in THF (15 mL) was activated with iodine crystals. A few drops of 1-bromo-4-(4-chlorophenyl)butane was added, and the the mixture was warmed until the exothermic Grignard reaction commenced. The remaining 1-bromo-4-(4-chlorophenyl)butane (233 g, 10 mmol) was added dropwise at a rate sufficient to maintain a gentle reflux. After addition was complete, the mixture was heated at reflux for 30 minutes and then cooled to −78° C. The resulting cold solution of was slowly cannulated into a cold solution of 4-(2-quinolylmethoxy)benzaldehyde (2.63 g, 10 mmol) in THF (25 mL), and the mixture was allowed to stand at ambient temperature for 12 hours. The reaction was quenched with saturated aqueous NH$_4$Cl (20 mL) and extracted with ethyl acetate (100 mL). The combined organic extracts were dried over MgSO$_4$ and concentrated in vacuo. The residue was chromatographed on silica gel eluting with 6:1 methylene chloride-ethyl acetate to afford 2.0 g of 4-(4-Chlorophenyl)-1-[4-( 2-quinolylmethoxy)phenyl] butan-1-ol.

Step 2: N-phthaloyl-O-(4-(4-chlorophenyl)-1-(4-(2-quinolyl-methoxy)phenyl)but-1-yl)hydroxylamine.

To a solution of 4-(4-Chlorophenyl)-1-[4-(2-quinolylmethoxy)phenyl]butan- 1-ol (630 mg, 1.5 mmol), prepared as in step 1, triphenylphosphine (393 mg, 1.5 mmol) and N-hydroxyphthalimide (245 mg, 1.5 mmol) in THF (120 mL) was added dropwise a solution of DIAD (0.3 mL, 1.5 mmol) in THF (10 mL). The resulting mixture was stirred at ambient temperature for 14 hours and then concentrated in vacuo. The residue was chromatographed on silica gel eluting with 3:1 hexane-ethyl acetate to provide 1.0 g of N-phthaloyl-O-(4-(4-chlorophenyl)-1-(4-(2-quinolyl-methoxy)phenyl)but- 1-yl)hydroxylamine.

Step 3: O-{4-(4-chlorophenyl)-1-[4-(2-quinolylmethoxy)-phenyl]but-1-yl} hydroxylamine A solution of the N-phthaloyl-O-(4-(4-chlorophenyl)-1-(4-(2-quinolyl-methoxy)phenyl)but- 1-yl)hydroxylamine prepared in step 2 in 2:1 ethanol-methylene chloride (60 mL) was treated with hydrazine hydrate (0.24 mL, 5.0 mmol) and refluxed for 30 minutes. Then 10% sodium carbonate (20 mL) was added and the resulting mixture was extracted with ethyl ether (100 mL). The ether extract was washed with water (2×50 mL) and brine, dried over MgSO$_4$ and concentrated in vacuo to provide 650 mg of O-{4-(4-chlorophenyl)-1-[4-(2-quinolylmethoxy)-phenyl] but-1-yl}hydroxylamine.

Step 4: {4-(4-chlorophenyl)-1-[4-(2-quinolylmethoxy)phenyl]-butyl}iminoxyacetic acid.

A solution of O-{4-(4-chlorophenyl)-1-[4-(2-quinolylmethoxy)-phenyl]but-1-yl} hydroxylamine in 1:5 water methanol (60 mL) was treated with glyoxylic acid hydrate (184 mg, 2 mmol) and acetic acid (0.12 mL; 2 mmol) for 18 hours at ambient temperature. The methanol was then removed in vacuo and the residue extracted with ethyl acetate. Purification on silica gel eluting with 8:1 methylene chloride-ethanol afforded 600 mg (80%) of {4-(4-chlorophenyl)-1-[4-(2-quinolylmethoxy)phenyl]butyl} iminoxyacetic acid as an amorphous solid. $^1$H NMR (300 MHz, DMSO-$d_6$) δ 1.5 (m, 1H), 1.65 (m, 2H), 1.9 (m, 1H), 2.6 (t, J=7 Hz, 2H), 5.1 (t, J=7 Hz, 1H), 5.4 (s, 2H), 7.05 (d, J=9 Hz, 2H), 7.2 (d, J=9 Hz, 2H), 7.3 (d, J=9 Hz, 2H), 7.6 (m, 3H), 7.8 (m, 1H), 8.0 (t, J=8 Hz, 2H), 8.4 (d, J=8 Hz, 1H). IR (CDCl$_3$): 3450, 1730, 1670, 1610 cm$^{-1}$. MS (DCI/NH$_3$) m/e 489 (M+H)$^+$.

EXAMPLE 13

Preparation of
[2-Cyclohexyl-1-(4-(2-quinolylmethoxy)phenyl)eth-1-yl] iminoxyacetic acid The desired material was prepared according to the procedure of Example 1, except substituting cyclohexylmethylmagnesium bromide for cyclohexylmagnesium chloride. m.p. 180°–181° C. $^1$H NMR (300 MHz, DMSO-$d_6$) δ 0.95 (m, 2H), 1.12 (m, 4H), 1.65 (m, 6H), 1.8 (m, 1H), 5.23 (t, J=7 Hz, 1H), 5.36 (s, 2H), 7.05 (d, J=9 Hz, 2H), 7.27 (d, J=9 Hz, 2H), 7.54 (s, 1H), 7.62 (m, 2H), 7.67 (d, J=8 Hz, 1H), 7.8 (m, 1H), 8.0 (t, J=8 Hz, 2H), 8.43 (d, J=8 Hz, 1H). MS (DCI/NH$_3$) m/e 433 (M+H)$^+$. Analysis calcd. for $C_{26}H_{28}N_2O_4$: C, 72.19; H, 6.52; N, 6.48. Found: C, 72.03; H, 6.50; N, 6.33.

EXAMPLE 14

Preparation of O-[2-Cyclohexyl-1-(4-(2-quinolylmethoxy)phenyl)-eth-1-yl]-4-carboxybenzaldoxime The title compound was prepared according to the procedure of Example 1, except substituting cyclohexylmethylmagnesium bromide for cyclohexylmagnesium chloride and substituting 4-carboxybenzaldehyde for glyoxylic acid. m.p. 167°–168° C. $^1$H NMR (300 MHz, DMSO-$d_6$) δ 0.95 (m, 2H), 1.15 (m, 4H), 1.6 (m, 4H), 1.73 (m, 2H), 1.87 (m, 1H), 5.23 (t, J=7 Hz, 1H), 5.46 (s, 2H), 7.05 (d, J=9 Hz, 2H), 7.32 (d, J=9 Hz, 2H), 7.63 (m, 4H), 7.79 (m, 1H), 7.93 (d, J=8 Hz, 2H), 8.0 (t, J=8 Hz, 2H), 8.31 (s, 1H), 8.41 (d, J=8 Hz, 1H). MS (DCI/NH$_3$) role 509 (M+H)$^+$. Analysis calcd. for $C_{32}H_{32}N_2O_4$: C, 74.56; H, 6.34; N, 5.51. Found: C, 74.89; H, 6.25; N, 5.35.

EXAMPLE 15

Preparation of [2-Cyclohexyl-1-(4-(2-quinolylmethoxy)phenyl)eth-1-yl]-2-iminoxypropionic acid The title compound was prepared according to the procedure of Example 2, except substituting cyclohexylmethylmagnesium bromide for cyclohexylmagnesium chloride. mp. 152–154° C. $^1$H NMR (300 MHz, DMSO-$d_6$) δ 0.94 (m, 2H), 1.12 (m, 4H), 1.65 (m, 7H), 1.9 (s, 3H), 5.14 (t, J=7 Hz, 1H), 5.35 (s, 2H), 7.03 d, J= 9 Hz, 2H), 7.22 (d, J=9 Hz, 2H), 7.65 (m, 2H), 7.79 (m, 1H), 8.02 (t, J=8 Hz, 2H), 8.42 (d, J=8 Hz, 1H). MS (DCI/NH$_3$) m/e 447 (M+H)$^+$. Analysis calcd for $C_{27}H_{30}N_2O_4$: C, 68.64; H, 6.99; N, 5.93. Found: C, 68.52; H, 6.39; N, 5.76.

EXAMPLE 16

Preparation of [2-cyclohexyl-1-(4-(2-quinolylmethoxy)phenyl)eth-1-yl]-4-iminoxypentanoic acid The title compound was prepared according to the procedure of Example 1, except substituting cyclohexylmethylmagnesium bromide for cyclohexylmagnesium chloride and substituting 4-oxopentanoic acid for glyoxylic acid. m.p. 94°–96° C. $^1$H NMR (300 MHz, DMSO-$d_6$) δ 0.92 (m, 2H), 1.15 (m, 4H), 1.47 (m, 1H), 1.65 (m, 9H), 2.38 (m, 4H), 4.98 (m, 1H), 5.35 (s, 2H), 7.02 (d, J=9 Hz, 2H), 7.2 (m, 2H), 7.62 (m, 1H), 7.68 (d, J=8 Hz, 1H), 7.8 (m, 1H), 8.02 (t, J=8 Hz, 2H), 8.43 (d, J=8 Hz, 1H). MS (DCI/NH$_3$) m/e 475 (M+H)$^+$. Analysis calcd. for $C_{29}H_{34}N_2O_4$: C, 73.38; H, 7.22; N, 5.83; Found: C, 73.00; H, 7.21; N, 5.83.

EXAMPLE 17

Preparation of [cycloheptyl-(4-(2-quinolylmethoxy)phenyl)methyl]-iminoxy acetic acid The title compound was prepared according to the procedure of Example 1, except substituting cycloheptylmagnesium bromide for cyclohexylmagnesium chloride. mp. 184–186° C. $^1$H NMR(300MHz, DMSO-$d_6$) δ 1.1 (m, 1H), 1.53 (m, 9H), 1.82 (m, 2H), 1.97 (m, 1H), 4.96 (d, J=7 Hz, 1H), 5.36 (s, 2H), 7.05 (d, J=9 Hz, 2H), 7.22 (d, J=9 Hz, 2H), 7.56 (s, 1H), 7.64 (m, 2H), 7.8 (t, J=8 Hz, 1H), 8.01 (t, J=8 Hz, 2H), 8.43 (d, J=8 Hz, 1H). MS (DCI/NH$_3$) m/e 433 (M+H)$^+$. Analysis calcd. for $C_{26}H_{28}N_2O_4$: C, 72.19; H, 6.52; N, 6.47. Found: C, 72.55; H, 6.55; N, 6.42.

EXAMPLE 18

Preparation of [2-cyclohexyl-1-(4-(4-thiazolylmethoxy)phenyl)-eth-1-yl]iminoxy acetic acid Step 1: 4-(4-thiazolylmethoxy)benzaldehyde.

To a solution of 4-hydroxybenzaldehyde (12.1 g, 100 mmol) and potassium carbonate (41.5 g, 0.30 mole) in DMF (100 mL) was added 4-thiazolylmethyl chloride hydrochloride (17.0 g, 100 mmol), and the resulting mixture was stirred at ambient temperature for 48 hours. The mixture was then poured into brine and filtered to collect the precipitated solid. The solid was washed with water (500 mL) and 10% ethyl ether in hexane and dried in vacuo to provide 17.6 g of 4-(4-thiazolylmethoxy)benzaldehyde.

Step 2: 2-cyclohexyl-1-(4-(4-thiazolylmethoxy)phenyl)ethan-1-ol.

A suspension of magnesium turnings (840 mg, 35 g-atom) in THF (25 mL) was activated with iodine crystals. A few drops of cyclohexylmethyl bromide were added, and the mixture was warmed until the exothermic Grignard reaction commenced. The remaining bromide (4.9 mL; 35 mmol) was added dropwise at a rate sufficient to maintain a gentle reflux. The mixture was refluxed for an additional 30 minutes, cooled to –78° C., and then slowly cannulated to a cold Solution of 4-( 4-thiazolylmethoxy)benzaldehyde (7.6 g, 35 mmol), prepared as in step 1, in THF (75 mL), and the resulting solution was allow to stand at ambient temperature for 12 hours. Saturated aqueous NH$_4$Cl (50 mL) was added and the mixture was extracted with ethyl acetate (100 mL). The organic layer was washed with water and brine, dried over MgSO$_4$ and concentrated in vacuo. The residue was purified on a silica gel column eluting with 7:3 hexane-ethyl acetate to provide 900 mg of cyclohexylmethyl-( 4-(4-thiazolylmethoxy)phenyl) ketone and 5.4 g of 2-cyclohexyl-1-(4-( 4-thiazolylmethoxy)phenyl)ethan-1-ol.

Step 3: N-phthaloyl-O-(2-cyclohexyl-1-(4-(4-thiazolylmethoxy)phenyl)eth-1-yl))hydroxylamine.

To a solution of 2-cyclohexyl-1-(4-(4-thiazolylmethoxy)phenyl)ethan-1-ol (4.75 g, 15 mmol), prepared as in step 2, N-hydroxyphthalimide (2.85 g, 17.5 mmol) and triphenylphosphine (5.0 g, 19 mmol) in THF (150 mL) was added dropwise DEAD (3.75 mL, 19 mmol). The solution was allowed to stir at ambient temperature for 14 hours and then concentrated in vacuo. The residue was chromatographed on silica gel eluting with 19:1 methylene chloride-ethyl acetate to provide 3.6 g of N-phthaloyl-O-(2-cyclohexyl-1-(4-(4-thiazolylmethoxy)phenyl)eth- 1-yl))hydroxylamine as an oil.

Step 4: O-{1-(2-cyclohexyl-1-[4(-thiazolylmethoxy)phenyl]ethyl)}hydroxylamine

A mixture of N-phthaloyl-O-(2-cyclohexyl-1-(4-(4-thiazolylmethoxy)phenyl)eth- 1-yl))hydroxylamine (1.4 g, 2.5 mmol), prepared as in step 3, and hydrazine hydrate (0.3 mL; 6 mmol) in ethanol (50 mL) was refluxed for 30 minutes and then cooled to ambient temperature. The precipitated solid was removed by filtration, and the filtrate was concentrated in vacuo. The residue was dissolved in methylene chloride and washed with 10% sodium carbonate, water and brine, over $MgSO_4$ and concentrated in vacuo to provide (0.85 g) of O-{1-(2-cyclohexyl- 1-[4-(-thiazolylmethoxy)phenyl]ethyl)}hydroxylamine.

Step 5: [2-cyclohexyl-1-(4-(4-thiazolylmethoxy)phenyl)eth-1-yl]iminoxy acetic acid.

A solution of O-{2-cyclohexyl-1-[4-(4-thiazolylmethoxy)phenyl]ethyl)} hydroxylamine (664 mg, 2 mmol), prepared as in step 4, glyoxylic acid hydrate (368 mg, 4.00 mmol) and acetic acid (0.12 mL; 2.0 mmol) in methanol (15 mL)-THF (60 mL)-$H_2O$ (15 mL) was stirred at ambient temperature for 14 hours and then concentrated in vacuo. The precipitated solid was filtered, washed with water and 10% ethyl ether in hexane, and dried in vacuo to provide 580 mg of [2-cyclohexyl-1-( 4-(4-thiazolylmethoxy)phenyl)eth-1-yl]iminoxy acetic acid as a white solid. m.p. 151°–153° C. $^1$H NMR (300 MHz; DMSO-$d_6$) δ 0.95 (m, 2H), 1.15 (m, 4H), 1.63 (m, 6H), 1.8 (m, 1H), 5.23 (m, 3H), 7.04 (d, J=9 Hz, 2H), 7.26 (d, J=9 Hz 2H), 7.55 (s, 1H), 7.68 (d, J=2 Hz, 1H), 9.13 (d, J=2 Hz, 1H). MS (DCI/$NH_3$) m/e 389 (M+H)$^+$, 406 (M+H+$NH_3$)$^+$. Analysis calcd. for $C_{20}H_{24}N_2O_4S$: C, 61.83; H, 6.22; N, 7.21. Found: C, 62.26; H, 6.32; N, 7.16.

EXAMPLE 19

Preparation of
O-[2-cyclohexyl-1-(4-(4-thiazolylmethoxy)phenyl)-eth-1-yl]-4-carboxybenzaldoxime The title compound was prepared according to the procedure of Example 18, except substituting 4-carboxybenzaldehyde for glyoxylic acid. m.p. 68° C. $^1$H NMR (300 MHz, DMSO-$d_6$) δ 0.95 (m, 2H), 1.22 (m, 4H), 1.73 (m, 7H), 5.32 (m, 3H), 7.03 (d, J=9 Hz, 2H), 7.32 (d, J=9 Hz, 2H), 7.63 (d, J=8 Hz, 2H), 7.78 (s, 1H), 7.93 (d, J=8 Hz, 2H), 8.34 (s, 1H), 9.14 (m, 1H). MS (DCI/$NH_3$) m/e 465 (M+H)$^+$, 482 (M+H+$NH_3$)$^+$. Analysis calcd. for $C_{26}H_{28}N_2O_4S$: C, 67.21; H, 6.07; N, 6.03. Found: C, 66.65; H, 6.08; N, 5.96.

EXAMPLE 20

Preparation of [2-cyclohexyl-1-(4-(4-thiazolyl methoxy)phenyl)eth-1-yl]-2-iminoxypropionic acid The title compound was prepared according to the procedure of Example 2, except substituting 2-cyclohexyl-1-(4-(4-thiazolylmethoxy)phenyl)ethan-1-ol, prepared as described in Example 18, step 2, for cyclohexyl-(4-(2-quinolylmethoxy)phenyl)methanol. m.p. 132°–134° C. $^1$H NMR (300 MHz, DMSO-$d_6$) δ 0.95 (m, 2H), 1.17 (m, 4H), 1.72 (m, 7H), 1.95 (s, 3H), 5.21 (m, 3H), 7.01 (d, J=9 Hz, 2H), 7.25 (d, J=9 Hz, 2H), 7.78 (d, J=2 Hz, 1H), 9.13 (d, J=2 Hz, 1H). MS (DCI/$NH_3$) m/e 403 (M+H)$^+$, 420 (M+H+$NH_3$)$^+$. Analysis calcd. for $C_{21}H_{26}N_2O_4S$: C, 62.65; H, 6.51; N, 6.96. Found: C, 62.62; H, 6.43; N, 6.89.

EXAMPLE 21

Preparation of
[3-Cyclohexyl-2-[4-(2-quinolylmethoxy)phenyl)-prop-1-yl]iminoxy acetic acid Step 1: 3-cyclohexyl-2-(4-(2-quinolylmethoxy)phenyl)propan-1-ol.

To a solution of 3-cyclohexyl-2-(4-(2-quinolylmethoxy)phenyl)propionic acid, prepared according to the procedure of K. Mohrs et al. U.S. Pat. No. 4,970,215, (1.37 g, 3.5 mmol) in THF (40 mL) at −10° C. was added triethylamine (0.5 mL, 3.6 mmol) and then dropwise a solution of ethyl chloroformate (0.36 mL, 3.6 mmol) in THF (10 mL). The reaction was stirred for 15 minutes at −10° to −5° C. and then was allowed to warm to 0° C. To the mixture was added sodium borohydride (380 mg, 10 mmol) followed by the dropwise addition of methanol (30 mL) for 30 minutes at 0° C. The resulting mixture was stirred for an additional 20 minutes and then was neutralized with 10% citric acid and extracted with ethyl acetate (100 mL). The ethyl acetate extract was washed with water and brine, dried over $MgSO_4$ and concentrated in vacuo. The residue was chromatographed on silica gel eluting with 2:1 hexane-ethyl acetate to provide 1.14 g of 3-cyclohexyl-2-( 4-(2-quinolylmethoxy)phenyl)propan-1-ol as an oil.

Step 2: N-phthalolyl-O-{1-(3-cyclohexyl-2-[4-(2-quinolylmethoxy)phenyl]-propyl} hydroxylamine.

To a solution of the 3-cyclohexyl-2-(4-(2-quinolylmethoxy)phenyl)propan-1-ol prepared in step 1, (1.10 g, 3.00 mmol), triphenylphosphine (1.31 g, 5.00 mmol) and N-hydroxyphthalimide (490 mg, 3.00 mmol) in THF (95 mL) was added dropwise a solution of DEAD (0.83 mL; 5 mmol) in THF (5 mL). The resulting mixture was stirred st ambient temperature for 12 hours and then was concentrated in vacuo. The residue was chromatographed on silica gel eluting with 35:1 methylene chloride-ethyl acetate to afford 1.5 g of N-phthaloyl-O-{1-(3-cyclohexyl-2-[4-(2-quinolylmethoxy] phenyl)}propyl)hydroxylamine.

Step 3: O-{1-(3-cyclohexyl-2-[4-(2-quinolylmethoxy)phenyl])propyl} hydroxylamine.

A mixture of N-phthaloyl-O-{1-(3-cyclohexyl-2-[4-(2-quinolylmethoxy]phenyl)} propyl)hydroxylamine (1.4 g, 2.7 mmol), prepared as in step 2, and hydrazine hydrate (0.30 mL, 6.0 mmol) in 1:1 ethanol-methylene chloride(60 mL) was refluxed for 30 minutes and then cooled to ambient temperature. 10% Sodium carbonate (30 mL) was added and the mixture was extracted with ethyl acetate (100 mL). The organic extract was washed with water (2×50 mL) and brine, dried over $MgSO_4$ and concentrated in vacuo. The residue was purified on a silica gel column eluting with 3:1 methylene chloride-ethyl acetate to afford 1.0 g of O-{1-(3-cyclohexyl- 2-[4-(2-quinolylmethoxy)phenyl])propyl}hydroxylamine.

Step 4: 1-{3-Cyclohexyl-2-[4-(2-quinolylmethoxy)phenyl]-propyl}iminoxyacetic acid.

A solution of O-{1-(3-cyclohexyl-2-[4-(2-quinolylmethoxy)phenyl])-propyl} hydroxylamine (390 mg, 1 mmol), prepared as in step 3, glyoxylic acid hydrate (100 mg, 1.00 mmol) and sodium acetate trihydrate (136 mg, 1.00 mmol) in methanol (25 mL)-THF (10 mL)-water (5 mL) was stirred at ambient temperature for 16 hours. The organics were removed in vacuo, and to the residue was added water (10 mL) and 1N NaOH (2 mL). The resulting mixture was washed with ethyl ether (15 mL) and acidified with 10% citric acid. The precipitated solid was filtered and recrystallized from ethyl acetate-hexane to provide 320 mg of 1-{3-Cyclohexyl-2-[4-(2-quinolylmethoxy)phenyl]propyl}iminoxyacetic acid. $^1$H NMR (300 MHz, DMSO-d$_6$) δ 0.8 (m, 2H), 1.05 (m, 4H), 1.53 (m, 6H), 1.74 (m, 1H), 3.05 (quintet, J=7 Hz, 1H), 4.2 (dd, J=7, 2 Hz, 2H), 5.35 (s, 2H), 7.0 (d, J= 9 Hz, 2H), 7.18 (d, J=9 Hz, 2H), 7.47 (s, 1H), 7.63 (t, J=8 Hz, 1H), 7.7 (d, J=8 Hz, 1H), 7.8 (m, 1H), 8.02 (t, J=8 Hz, 2H), 8.42 (d, J=8 Hz, 1H). MS (DCI/NH$_3$) m/e 447 (M+H)$^+$. Analysis calcd. for C$_{27}$H$_{30}$N$_2$O$_4$: C, 72.62; H, 6.77; N, 6.27. Found: C, 72.46; H, 6.72; N, 6.13.

EXAMPLE 22

Preparation of [3-cyclohexyl-2-(4-(2-quinolylmethoxy)phenyl)prop-1-yl]-2-iminoxypropionic acid Step 1: 3-cyclohexyl-2-(4-(2-quinolylmethoxy)phenyl)prop-1-yl]-2-iminoxypropionic acid methyl ester A mixture of O-{1-(3-cyclohexyl-2-[4-(2-quinolylmethoxy)phenyl] )propyl}-hydroxylamine (320 mg, 0.80 mmol), prepared as in Example 21, step 3, methyl pyruvate (0.092 mL, 1.00 mmol) and acetic acid (0.06 mL) in 2:1 methanol -THF (30 mL) was stirred at ambient temperature for 20 hours and then was concentrated in vacuo. The residue was chromatographed on silica gel eluting with 3:1 hexane-ethyl acetate to provide 260 mg of 3-cyclohexyl-2-(4-( 2-quinolylmethoxy)phenyl)prop- 1-yl]-2-iminoxypropionic acid methyl ester.

Step 2: 3-cyclohexyl-2-(4-(2-quinolylmethoxy)phenyl)prop-1-yl]-2-iminoxypropionic acid The 3-cyclohexyl -2-(4-(2-quinolylmethoxy)phenyl)prop-1-yl]-2-iminoxypropionic acid methyl ester prepared in step 1 was hydrolyzed with 1N sodium hydroxide (2 mL) at 50° C. for 90 minutes. The methanol was removed in vacuo, and the aqueous solution was diluted with 20 mL of water. The resulting solution was acidified with 10% citric acid, washed with ethyl acetate, dried over magnesium sulfate and concentrated in vacuo to afford the title compound as an amorphous solid. $^1$H NMR (300 MHz, DMSO-d$_6$) δ 0.8 (m, 2H), 1.05 (m, 4H), 1.53 (m, 6H), 1.72 (m, 1H), 1.82 (s, 3H), 3.05 (quintet, J=7 Hz, 1H), 4.2 (m, 2H), 5.33 (s, 2H), 7.0 (d, J=9 Hz, 2H), 7.17 (d, J=9 Hz, 2H), 7.63 (t, J=8 Hz, 1H), 7.7 (d, J=8 Hz, 1H), 7.8 (m, 1H), 8.02 (t, J=8 Hz, 2H), 8.42 (d, J=8 Hz, 1H). MS (DCI/NH$_3$) m/e 461 (M+H)$^+$. IR (CDCl$_3$): 3440, 1760, 1600 cm$^{-1}$. Analysis calcd. for C$_{28}$H$_{32}$N$_2$O$_4$: C, 73.02; H, 7.00; N, 6.08. Found: C, 72.26; H, 6.89; N, 5.87.

EXAMPLE 23

Preparation of [3-Cyclohexyl-2-(4-(2-quinolylmethoxy)phenyl)-prop-1-yl}-3-iminoxy-( 2,2-dimethyl)propionic acid The title compound was prepared according to the procedure of Example 22, except substituting 3-carbomethoxy-2,2-dimethylpropionaldehyde for methyl pyruvate. E-isomer: $^1$H NMR (300 MHz, DMSO-d$_6$) δ 0.82 (m, 2H), 1.05 (m, 4H), 1.12 (s, 6H), 1.52 (m, 6H), 1.7 (m, 1H), 2.97 (m, 1H), 3.92 (d, J=7 Hz, 2H), 5.33 (s, 2H), 6.98 (d, J=9 Hz, 2H), 7.14 (d, J=9 Hz, 2H), 7.48 (s, 1H), 7.62 (m, 1H), 7.68 (d, J=8 Hz, 1H), 7.8 (m, 1H), 8.02 (t, J=8 Hz, 2H), 8.42 (d, J=8 Hz, 1H). MS (DCI/NH$_3$) m/e 489 (M+H)$^+$. Z-isomer: $^1$H NMR (300 MHz, DMSO-d$_6$) δ 0.83 (m, 2H), 1.03 (m, 4H), 1.22 (s, 6H), 1.55 (m, 6H), 1.7 (m, 1H), 3.0 (m, 1H), 3.97 (d, J=7 Hz, 2H), 5.33 (s, 2H), 6.98 (d, J=9 Hz, 2H), 7.14 (d, J=9 Hz, 2H), 7.43 (s, 1H), 7.65 (m, 2H), 7.8 (m, 1H), 8.02 (t, J=8 Hz, 2H), 8.42 (d, J=8 Hz, 1H). MS (DCI/NH$_3$) m/e 489 (M+H)$^+$.

EXAMPLE 24

Preparation of [4-(4-fluorophenyl)-1-(4-(2-quinolylmethoxy)-phenyl)but-1-yl] iminoxyacetic acid.

The title compound was prepared according to the procedure of Example 12, except substituting 1-bromo-4-(4-fluorophenyl)butane for 1-bromo-4-(4-chlorophenyl)butane. m.p. 152°–154° C. $^1$H NMR (300 MHz, DMSO-d$_6$) δ 1.55 (m, 2H), 1.73 (m, 1H), 1.92 (m, 1H), 2.58 (t, J=7 Hz, 2H), 5.18 (t, J=7 Hz 1H), 5.36 (s, 2H), 7.06 (m, 4H), 7.18 (m, 2H), 7.25 (d, J=9 Hz, 2H), 7.57 (s, 1H), 7.63 (m, 2H), 7.78 (m, 1H), 8.0 (t, J=8 Hz, 2H), 8.43 (d, J=8 Hz, 1H). MS (DCI/NH$_3$) m/e 473 (M+H)$^+$. Analysis calcd. for C$_{28}$H$_{25}$FN$_2$O$_4$: C, 71.11; H, 5.33; N, 6.03. Found: C, 71.24; H, 5.36; N, 5.86.

EXAMPLE 25

Preparation of [4-(4-fluorophenyl)-1-(4-(2-quinolylmethoxy)-phenyl)but-1-yl]-2-iminoxypropionic acid.

The title compound was prepared according to the procedure of Example 12, except substituting 1-bromo-4-(4-fluorophenyl)butane for 1-bromo-4-(4-chlorophenyl)butane and substituting pyruvic acid for glyoxylic acid. m.p. 160°–162° C. $^1$H NMR (300 MHz, DMSO-d$_6$) δ 1.55 (m, 2H), 1.73 (m, 2H), 1.97 (s, 3H), 2.57 (t, J=7 Hz, 2H), 5.18 (t, J=7 Hz, 1H), 5.35 (s, 2H), 7.05 (t, J=9 Hz, 4H), 7.18 (m, 2H), 7.23 (d, J=9 Hz, 2H), 7.63 (m, 1H), 7.68 (d, J=8 Hz, 1H), 7.79 (m, 1H), 8.02 (t, J=8 Hz, 2H), 8.42 (d, J=8 Hz, 1H). MS (DCI/NH$_3$) m/e 487 (M+H)$^+$. Analysis calcd. for C$_{29}$H$_{27}$FN$_2$O$_4$: C, 71.58; H, 5.59; N, 5.76. Found: C, 72.05; H, 5.57; N, 5.77.

EXAMPLE 26

Preparation of [2-cyclohexyl-2-(4-(2-quinolylmethoxy)phenyl)-eth-1-yl}-iminoxyacetic acid.

The title compound was prepared according to the procedure of Example 21, except substituting 2-cyclohexyl-2-(4-(2-quinolylmethoxy)phenyl)acetic acid for 3-cyclohexyl-2-(4-(2-quinolylmethoxy)phenyl)propionic acid. m.p. 68°–70° C. (recrystallized from ethyl acetate-hexane). $^1$H NMR (DMSO-d$_6$, 300 MHz) δ 1.0 (m, 5H), 1.42 (m, 1H), 1.6 (m, 4H), 1.83 (m, 1H), 2.75 (m, 1H), 4.44 (m, 2H), 5.34 (s, 2H), 7.0 (d, J=9 Hz, 2H), 7.12 (d, J=9 Hz, 2H), 7.43 (s, 1H), 7.63 (m, 1H), 7.7 (d, J=8 Hz, 1H), 7.8 (m, 1H), 8.0 (t, J=8 Hz, 2H), 8.42 (d, J=8 Hz, 1H). MS (DCI/NH$_3$) m/e 433 (M+H)$^+$. IR (in CDCl$_3$): 1760, 1695, 1600 cm$^{-1}$. Analysis calcd. for C$_{26}$H$_{28}$N$_2$O$_4$: C, 72.20; H, 6.53; N, 6.48. Found: C, 71.65; H, 6.63; N, 6.38.

EXAMPLE 27

Preparation of [2-Cycloheptyl-2-(4-(2-quinolylmethoxy)phenyl)-eth-1-yl] iminoxyacetic acid.

The title compound was prepared according to the procedure of Example 21, except substituting 2-cycloheptyl-2-(4-(2-quinolylmethoxy)phenyl)acetic acid for 3-cyclohexyl- 2-(4-(2-quinolylmethoxy)phenyl)propionic acid. m.p. 73°–74° C. (recrystallized from ethyl acetate-hexane). $^1$H NMR (DMSO-d$_6$, 300 MHz) δ 1.05 (m, 1H), 1.43 (m, 10H), 1.78 (m, 2H), 2.85 (q, J=7 Hz, 1H), 4.44 (m, 2H), 5.33 (s, 2H), 7.0 (d, J=9 Hz, 2H), 7.14 (d, J=9 Hz, 2H), 7.43 (s, 1H), 7.52 (m, 1H), 7.68 (d, J=8 Hz, 1H), 7.8 (m, 1H), 8.03 (t, J=8 Hz, 2H), 8.42 (d, J=8 Hz, 1H). MS (DCI/NH$_3$) m/e 447 (M+H)$^+$. IR (CDCl$_3$): 1760, 1695, 1600 cm$^{-1}$. Analysis calcd. for C$_{27}$H$_{30}$N$_2$O$_4$: C, 72.62; H, 6.77; N, 6.27. Found: C, 72.19; H, 6.75; N, 6.13.

EXAMPLE 28

Preparation of [2-cycloheptyl-2-(4-(2-quinolylmethoxy)phenyl)-eth-1-yl]-3-iminoxy- 2,2-dimethylpropionic acid.

The title compound was prepared according to the procedure of Example 21, except substituting 2-cycloheptyl-2-[4-(2-quinolylmethoxy)phenyl]acetic acid for 3-cyclohexyl-2-[4-(2-quinolylmethoxy)phenyl]propionic acid and substituting 3-carbomethoxy- 2,2-dimethylpropionaldehyde for glyoxylic acid. m.p. 106°–107° C. (recrystallized from ethyl acetate-hexane). $^1$H NMR (DMSO-d$_6$, 300 MHz) δ 1.03 (m, 1H), 1.22 (s+m, 8H), 1.38 (m, 3H), 1.5 m, 5H), 1.77 (m, 2H), 2.78 (m, 1H), 4.2 (m, 2H), 5.33 (s, 2H), 6.97 (d, J=9 Hz, 2H), 7.12 (d, J=9 Hz, 2H), 7.38 (s, 1H), 7.64 (m, 1H), 7.7 (d, J=8 Hz, 1H), 7.8 (m, 1H), 8.02 (t, J=8 Hz, 2H), 8.43 (d, J=8 Hz, 1H). MS (DCI/NH$_3$) m/e 489 (M+H)$^+$. Analysis calcd. for C$_{30}$H$_{36}$N$_2$O$_4$: C, 73.74; H, 7.43; N, 5.73. Found: C, 73.67; H, 7.46; N, 5.61.

EXAMPLE 29

Preparation of [2-cyclopentyl-2-(4-(2-quinolylmethoxy)phenyl)-eth-1-yl] iminoxyacetic acid.

The title compound was prepared according to the procedure of Example 21, except substituting 2-cyclopentyl-2-[4-(2-quinolylmethoxy)phenyl]acetic acid for 3-cyclohexyl-2-[4-(2-quinolyl-methoxy)phenyl]propionic acid. m.p. 88°–90° C. (recrystallized from ethyl acetate-hexane). $^1$H NMR (DMSO-d$_6$, 300 MHz) δ 0.96 (m, 1H), 1.35 (m, 6H), 1.85 (m, 1H), 2.03 (m, 1H), 2.72 (m, 1H), 4.4 (m, 2H), 5.35 (s, 2H), 7.0 (d, J=9 Hz, 2H), 7.15 (d, J=9 Hz, 2H), 7.43 (s, 1H), 7.63 (m, 1H), 7.7 (d, J=8 Hz, 1H), 7.8 (m, 1H), 8.03 (t, J=8 Hz, 2H), 8.43 (d, J=8 Hz, 1H), 13.25 (broad s, 1H). MS (DCI/NH$_3$) m/e 419 (M+H)$^+$. Analysis calcd. for C$_{25}$H$_{26}$N$_2$O$_4$. 0.5 H$_2$O: C, 70.24; H, 6.37; N, 6.55. Found: C, 70.47; H, 6.24; N, 6.39.

EXAMPLE 30

Preparation of [Cyclohexyl-(4-(2-quinolylmethoxy)phenyl)methyl]-Z-2-iminoxypropionic acid methyl ester.

The mixture of Z and E isomers obtained according to the procedure of Example 2 was separated by chromatography on silica gel (hexane-ethyl ether 3:1). [Cyclohexyl-(4-(2-quinolylmethoxy)phenyl)methyl]-Z-2-iminoxypropionic acid methyl ester (140 mg). $^1$H NMR (300 MHz, DMSO-d$_6$) δ: 0.93 (m, 3H), 1.08 (m, 2H), 1.32 (m, 1H), 1.60 (m, 4H), 1.68 (m, 1H), 1.91 (s, 3H), 3.80 (s, 3H), 4.73 (d, 1H, J=7 Hz), 5.36 (s, 2H), 7.03 (d, 2H, J=9 Hz), 7.14 (d, 2H, J=9 Hz), 7.62 (m, 1H), 7.69 (d, 1H, J=8 Hz), 7.78 (m, 1H), 8.02 (m, 2H), 8.43 (d, 1H, J= 8 Hz). MS (DCI/NH$_3$) m/e 447 (M+H)$^+$. Analysis calcd. for C$_{27}$H$_{30}$N$_2$O$_4$: C, 72.62; H, 6.77; N, 6.27. Found: C, 72.49; H, 6.61; N, 5.99.

EXAMPLE 31

Preparation of [Cyclohexyl-(4-(2-quinolylmethoxy)phenyl)methyl]-E-2-iminoxypropionic acid methyl ester.

The desired compound (960 mg), was obtained in the chromatography described in Example 30. E isomer: m.p. 105°–106° C. $^1$H NMR (300 MHz, DMSO-d$_6$) δ 1.05 (m, 5H), 1.33 (m, 1H), 1.67 (m, 4H), 1.85 (m, 1H), 2.03 (s, 3H), 3.68 (s, 3H), 4.95 (d, 1H, J=7 Hz), 7.04 (9d, 2H, J=9 Hz), 7.19 (d, 2H, J=9 Hz), 7.63 (m, 1H), 7.67 (d, 1H, J=8 Hz), 7.80 (m, 1H), 8.00 (m, 2H), 8.42 (d, 1H, J= 8 Hz). MS (DCI/NH$_3$) m/e 447 (M+H)$^+$. Analysis calcd. for C$_{27}$H$_{30}$N$_2$O$_4$: C, 72.62; H, 6.77; N, 6.27. Found: C, 72.45; H, 7.11; N, 6.09.

EXAMPLE 32

Preparation of [cyclohexyl-(4-(2-quinolylmethoxy)phenyl)methyl]-Z-2-iminoxy propionic acid.

To a solution of [Cyclohexyl-(4-(2-quinolylmethoxy)phenyl)methyl]-Z-2-iminoxypropionic acid methyl ester (74 mg, 0.17 mmol), prepared as in Example 30, in dioxane-methanol (2:1) (12 ml) was added 1N sodium hydroxide (1 ml) and the resulting mixture was stirred at room temperature for 24 hours. The organics were then removed in vacuo, and the residue was diluted with water (10 ml) and acidified to pH 3. The precipitated product was filtered, dried in vacuo and recrystallized from ethyl acetate-hexane to provide [Cyclohexyl-(4-(2-quinolylmethoxy)phenyl)methyl]-Z-2-iminoxypropionic acid. m.p. 142°–144° C. $^1$H NMR (300 MHz, DMSO-d$_6$) δ 1.07 (m, 5H), 1.30 (m, 1H), 1.62 (m, 5H), 1.87 (s, 3H), 4.70 (d, 1H, J= 7 Hz), 5.35 (s, 2H), 7.02 (d, 2H, J=9 Hz), 7.14 (d, 2H, J=9 Hz), 7.62 (m, 1H), 7.68 (d, 1H, J=9 Hz), 7.80 (m, 1H), 8.01 (m, 2H), 8.41 (d, 1H, J=9 Hz), 13.56 (broad s, 1H). MS (DCI/NH$_3$) m/e 433 (M+H)$^+$. Analysis calcd. for C$_{26}$H$_{28}$N$_2$O$_4$: C, 72.20; H, 6.53; N, 6.48. Found: C, 71.71; H, 6.75; N, 6.16.

EXAMPLE 33

Preparation of [cyclohexyl-(4-(2-quinolylmethoxy)phenyl)methyl]-E-2-iminoxy propionic acid.

The desired compound was prepared according to the method of Example 32, except substituting [Cyclohexyl-(4-(2-quinolylmethoxy)phenyl)methyl]-E-2-iminoxypropionic acid methyl ester (770 mg, 1.7 mmol), prepared as in Example 31, for [Cyclohexyl-(4-(2-quinolylmethoxy)phenyl)methyl]-Z-2-iminoxypropionic acid methyl ester. m.p. 183°–184° C. $^1$H NMR (300 MHz, DMSO-d$_6$) δ 1.12 (m, 5H), 1.35 (m, 1H), 1.67 (m, 4H), 1.86 (m, 1H), 1.98 (s, 3H), 4.92 (d, 1H, J=7 Hz), 5.35 (s, 2H), 7.03 (d, 2H, J=9 Hz), 7.17 (d, 2H, J=9 Hz), 7.62 (m, 1H), 7.68 (d, 1H, J=9 Hz), 7.78 (m, 1H), 8.00 (m, 2H), 8.42 (d, 1H, J=9 Hz). MS (DCI/NH$_3$) m/e: 433 (M+H)$^+$. Analysis calcd. for C$_{26}$H$_{28}$N$_2$O$_4$: C, 72.20; H, 6.53; N, 6.48. Found: C, 71.90; H, 6.75; N, 6.28.

EXAMPLE 34

Preparation of
(R)-[Cyclohexyl-(4-(2-quinolylmethoxy)phenyl]-
methyl]-E-2-iminoxypropionic acid methyl ester.

Step 1: N-benzyloxy-(2R,3R)dibenzoyltartimide.

To a solution of dibenzoyl anhydride of tartaric acid (14.0 g, 40 mmol) in THF (100 ml) was added O-benzylhydroxylamine (5.4 g, 44 mmol) and the mixture was stirred at room temperature for 12 hours. The THF was then removed in vacuo, and the residue was reddissolved in chloroform (100 ml). To the resulting solution at 0° C. was added dropwise thionyl chloride (3.65 ml, 50 mmol) and the mixture was allowed to warm to room temperature for 4 hours. The solution was then concentrated in vacuo and the residue was chromatographed (silica gel, methylene chloride-ethyl acetate 19:1) to afford 18.9 g of N-benzyloxy-(2R,3R)dibenzoyltartimide.

Step 2: N-hydroxy-(2R,3R)dibenzoyltartrimide.

The N-benzyloxy-(2R,3R)dibenzoyltartimide prepared in step 1 was hydrogenated with hydrogen in ethyl acetate (250 ml) over 10% palladium on charcoal (1.9 g) under atmospheric pressure to provide, after filtration of the catalyst and evaporation of the solvent, 14 g of N-hydroxy-(2R, 3R)dibenzoyltartrimide, αD= +161.2 (c=0.5, THF).

Step 3: N-(R)-[cyclohexyl-(4-(2-quinolylmethoxy)phenyl)methoxy] (2R,3R)dibenzoyltartrimide.

To a solution of N-hydroxy-(2R,3R)dibenzoytartrimide (1.42 g, 4 mmol), prepared as in step 2, cyclohexyl-(4-(2-quinolylmethoxy)phenyl)methanol (1.4 g, 4 mmol), prepared according to the procedure of Example 1, step 2, and triphenylphosphine (1.57 g, 6 mmol) in THF (50 ml) was added dropwise a solution of DEAD (0.96 ml, 6 mmol) in THF (5 ml), and the resulting mixture was stirred at room temperature for 4 hours. The mixture was then concentrated in vacuo and the residue was chromatographed twice. First using toluene-ethyl acetate, 19:1 to separate product from the triphenylphosphine oxide and diethyl hydrazine dicarboxylate and then hexane-methylene chloride-ethyl acetate (54:40:6) to separate diastereoisomers. The N-(R)-[cyclohexyl-(4-(2-quinolylmethoxy)phenyl)methoxy]-(2R,3R)dibenzoyltartrimide (470 mg) was eluted first and the N-(S)-[cyclohexyl-(4-( 2-quinolylmethoxy)phenyl)methoxy]-(2R,3R)-dibenzoyltartrimide (310 mg) was eluted second.

Step 4: O-(R)-[cyclohexyl-(4-(2-quinolylmethoxy)phenyl)methyl]hydroxylamine.

A mixture of N-(R)-[cyclohexyl-(4-(2-quinolylmethoxy)phenyl)methoxy]-( 2R,3R)-dibenzoyltartrimide (470 mg, 0.687 mmol), prepared as in step 3, and hydrazine hydrate (0.35 ml) in 1:1 ethanol-dioxane (30 ml) was refluxed for 30 min and then was allowed to cool to room temperature. To the mixture was added 10% sodium carbonate and the product was extracted with ethyl acetate (100 ml). The extract was washed with water, and brine, dried over MgSO$_4$, and concentrated in vacuo. The residue was purified on silica gel column (hexane-ethyl acetate 2:1) to provide 200 mg of O-(R)-[cyclohexyl-(4-(2-quinolylmethoxy)phenyl)methyl]hydroxylamine.

Step 5: (R)-[Cyclohexyl-(4-(2-quinolylmethoxy)phenyl] methyl]-E-2-iminoxypropionic acid methyl ester.

To a solution of the O-(R)-[cyclohexyl-(4-(2-quinolylmethoxy)phenyl)methyl] hydroxylamine prepared in step 4 in dioxane (15 ml) and methanol (10 ml) were added acetic acid (0.03 ml), water (1 ml) and methyl pyruvate (0.06 nil, 0.6 mmol) and the reaction mixture was stirred at room temperature for 12 hours. The organics were removed in vacuo and the residue was extracted with ethy acetate, dried over MgSO$_4$, and concentrated in vacuo. The residue was chromatographed (silica gel, hexane-ethyl ether 3:1) to provide 100 mg of (R)-[Cyclohexyl-(4-(2-quinolylmethoxy)phenyl]methyl]-E-2-iminoxypropionic acid methyl ester, αD=−35.0 (c=0.1, CHCl$_3$). m.p. 99°–101° C. $^1$H NMR (300 MHz, DMSO-d$_6$) δ 1.60 (m, 5H), 1.35 (m, 1H), 1.64 (m, 4H), 1.77 (m, 1H), 2.03 (s, 3H), 3.67 (s, 3H), 4.95 (d, 1H, J=7 Hz), 5.36 (s, 2H), 7.03 (d, 2H, J=9 Hz), 7.18 (d, 2H, J=9 Hz), 7.65 (m, 2H), 7.79 (m, 1H), 8.01 (t, 2H, J=9 Hz), 8.41 (d, 1H, J=9 Hz). MS (DCI/NH$_3$) m/e 447 (M+H)$^+$.

EXAMPLE 35

Preparation of
(R)-[Cyclohexyl-(4-(2-quinolylmethoxy)phenyl)-
methyl]-E-2-iminoxypropionic acid.

To a solution of (R)-[Cyclohexyl-(4-(2-quinolylmethoxy)phenyl]methyl]-E-2-iminoxypropionic acid methyl ester (80 mg, 0.18 mmol), prepared as in Example 34, in dioxane (6 ml) and methanol (3 ml) was added 1N NaOH (0.2 ml) and the resulting mixture was stirred at room temperature for 10 hours. The mixture was then concentrated in vacuo, the residue was diluted with water (5 ml) and acidified to pH 3. The solid was filtered, dried in vacuo and crystallized from ethyl acetate-hexane to afford 50 mg of (R)-[Cyclohexyl-(4-(2-quinolylmethoxy)phenyl)methyl]-E-2-iminoxypropionic acid. m.p. 179°–180° C. αD=−18.0 (c=0.1, CHCl$_3$). $^1$H NMR (300 MHz, DMSO-d$_6$) δ 1.11 (m, 5H), 1.37 (m, 1H), 1.65 (m, 4H), 1.87 (m, 1H), 2.00 (s, 3H), 4.42 (d, 1H, J=7 Hz), 5.36 (s, 2H), 7.03 (d, 2H, J=9 Hz), 7.19 (d, 2H, J=9 Hz), 7.65 (m, 2H), 7,78 (m, 1H), 8.01 (t, 2H, J=9 Hz), 8.41 (d, 1H, J= 9 Hz), 12.89 (broad s, 1H). MS (DCI/NH$_3$) m/e 433 (M+H)$^+$. Analysis calcd. for C$_{26}$H$_{28}$N$_2$O$_4$: C, 72.20; H, 6.53; N, 6.48. Found: C, 71.98; H, 6.44; N, 6.30.

EXAMPLE 36

Preparation of
(S)-[Cyclohexyl-(4-(2-quinolylmethoxy)phenyl)-
methyl]-E-2-iminoxypropionic acid methyl ester.

Step 1: N-(S)-[cyclohexyl-(-4-(2-quinolylmethoxy)phenyl)methoxy]-(2S,3S)-dibenzoyltartrimide.

To a solution of O-(RS)-[cyclohexyl-(4-(2-quinolylmethoxy)phenyl)methyl] hydroxylamine (253 mg, 1.50 mmol), prepared according to the procedure of Example 1, step 3, in THF (30 ml) was added (2S,3S)-dibenzoyltartaric acid anhydride (510 mg, 1.50 mmol), followed after 30 min by N-hydroxysuccinimide (230 mg, 2 mmol) and dicyclohexylcarbodiimide (412 mg, 2.00 mmol). The resulting mixture was stirred at room temperature for 14 hours. The mixture was then concentrated in vacuo and the residue was chromatographed (silica gel, hexane-methylene chloride-ethyl acetate (54:40:6) to afford 140 mg of N-(S)-[cyclohexyl-(-4-( 2-quinolylmethoxy)phenyl)methoxy]-(2S,3S)-dibenzoyltartrimide (elutes first) and 70 mg of N-(R)-[cyclohexyl-(4-(2-quinolylmethoxy)phenyl)methoxy]-(2S,3S)-dibenzoyltartrimide (elutes second).

Step 2: (S)-[Cyclohexyl-(4-(2-quinolylmethoxy)phenyl)methyl]-E-2-iminoxypropionic acid methyl ester.

The desired material was prepared as described in the procedure of Example 34, except substituting N-(S)-[cyclohexyl-(4-(2-quinolylmethoxy)phenyl)methoxy]-(2R,3R) dibenzoyltartrimide, prepared as in step 1, for N-(R)-[cyclohexyl-(4-(2-quinolylmethoxy)phenyl) methoxy]-(2R, 3R)-dibenzoyltartrimide. αD=+33.3 (c= 0.15, CHCl$_3$). m.p. 96°–98° C. $^1$H NMR (300 MHz, DMSO-d$_6$) δ 1.11 (m, 5H), 1.35 (m, 1H), 1.64 (m, 4H), 1.87 (m, 1H), 2.03 (s, 3H), 3.68 (s, 3H), 4.94 d, 1H, J=7 Hz), 5.35 (s, 2H), 7.03 (d, 2H, J=9 Hz), 7.18 (d, 2H, J=9 Hz), 7.62 (m, 1H), 7.68 (d, 1H, J=9 Hz), 7.79 (m, 1H), 8.01 (t, 2H, J=9 Hz), 8.42 (d, 1H, J=9 Hz). MS (DCI/NH$_3$) m/e 447 (M+H)$^+$.

EXAMPLE 37

Preparation of (S)-[Cyclohexyl-(4-(2-quinolylmethoxy)phenyl)-methyl]-E-2-iminoxypropionic acid.

The desired material was prepared according to the method of Example 35, except substituting (S)-[Cyclohexyl-(4-(2-quinolylmethoxy)phenyl)methyl]-E-2-iminoxypropionic acid methyl ester, prepared as in Example 36, for (R)-[Cyclohexyl-( 4-(2-quinolylmethoxy)phenyl]methyl]-E-2-iminoxypropionic acid methyl ester αD= 16.7 (c=0.15, CHCl$_3$); mp. 179°–180° C.; $^1$H NMR (300 MHz, DMSO-d$_6$) δ 1.12 (m, 5H), 1.36 (m, 1H), 1.67 (m, 4H), 1.85 (m, 1H), 2.00 (s, 3H), 4.92 (d, 1H, J= 7 Hz), 5.35 (s, 2H), 7.03 (d, 2H, J=9 Hz), 7.18 (d, 2H, J=9 Hz), 7.65 (m, 2H), 7.80 (m, 1H), 8.00 (t, 2H, J=9 Hz), 8.42 (d, 1H, J=9 Hz), 12.88 (broad s, 1H), MS (DCI/NH$_3$) m/e: 433 (M+1); Analysis calcd. for C$_{26}$H$_{28}$N$_2$O$_4$: C, 72.20; H, 6.53; N, 6.48; Found: C, 72.01; H, 6.49; N, 6.27.

EXAMPLE 38

Preparation of [Cyclohexyl-(4-(2-quinolylmethoxy)phenyl)methyl]-Z-iminoxyacetic acid methyl ester.

A mixture of O-[cyclohexyl-(4-(2-quinolylmethoxy)phenyl)methyl] hydroxylamine (347 mg, 1 mmol), prepared according to the procedure of Example 1, step 4, glyoxylic acid hydrate (92 mg, 1.0 mmol) and acetic acid (0.06 ml, 1.0 mmol) in dioxane (15 ml), water (1 ml) and methanol (10 ml) was stirred at ambient temperature for 8 hours. The organics were removed in vacuo and the product was extracted with ethyl acetate. The extract was dried over MgSO$_4$, and concentrated in vacuo. The residue was dissolved in DMF (25 ml) and was treated with sodium bicarbonate (84 mg, 1.0 mmol) and iodomethane (3 ml), and the resulting mixture was stirred at ambient temperature for 72 hours. The reaction mixture was then poured into water (50 ml), and extracted with ethyl acetate. The organic extract was washed with water and brine, dried over anhydrous MgSO$_4$ and concentrated in vacuo. The residue was chromatographed (silica gel, hexane-ethyl ether 25:10) to afford 18 mg of [Cyclohexyl-(4-(2-quinolylmethoxy)phenyl)methyl]-Z-iminoxy acetic acid methyl ester. $^1$H NMR (300 MHz, DMSO-d$_6$) δ 1.10 (m, 5H), 1.33 (m, 1H), 1.56 (m, 4H), 1.85 (m, 1H), 3.75 (s, 3H), 4.84 (d, 1H, J=7 Hz), 5.36 (s, 2H), 7.03 (d, 2H, J=9 Hz), 7.15 (d, 2H, J=9 Hz), 7.26 (s, 1H), 7.62 (m, 1H), 7.78 (d, 1H, J=9 Hz), 7.79 (m, 1H), 8.01 (t, 2H, J=9 Hz), 8.42 (d, 1H, J=9 Hz). MS (DCI/NH$_3$) m/e 433 (M+H)$^+$.

EXAMPLE 39

Preparation of [Cyclohexyl-(4-(2-quinolylmethoxy)phenyl)methyl]-E-iminoxyacetic acid methyl ester.

[Cyclohexyl-(4-(2-quinolylmethoxy)phenyl)methyl]-E-iminoxy acetic acid methyl ester (225 mg), was isolated from the chromatography described in Example 38. $^1$H NMR (300 MHz, DMSO-d$_6$) δ 1.10 (m, 5H), 1.28 (m, 1H), 1.65 (m, 4H), 1.90 (m, 1H), 3.69 (s, 3H), 4.42 (d, 1H, J=7 Hz), 5.36 (s, 2H), 7.05 (d, 2H, J= 9 Hz), 7.20 (d, 2H, J=9 Hz), 7.62 (m, 1H), 7.78 (m, 2H), 7.80 (m, 1H), 8.01 (m 2H), 8.42 (d, 1H, J=9 Hz). MS (DCI/NH$_3$) m/e 433 (M+H)$^+$.

EXAMPLE 40

Preparation of [Cyclohexyl-(4-(2-quinolylmethoxy)phenyl)methyl]-E-iminoxyacetic acid.

The desired material was prepared according to the method of Example 35, except substituting [Cyclohexyl-(4-(2-quinolylmethoxy)phenyl)methyl]-E-iminoxy acetic acid methyl ester, prepared as in Example 39, for (R)- [Cyclohexyl-(4-(2-quinolylmethoxy)phenyl] methyl]-E-2-iminoxypropionic acid methyl ester. m.p. 197°– 198° C. $^1$H NMR (300 MHz, DMSO-d$_6$) δ 1.10 (m, 5H), 1.68 (m, 1H), 1.65 (m, 4H), 1.90 (m, 1H), 4.89 (d, 1H, J=7 Hz), 5.35 (s, 2H), 7.04 (d, 2H, J=9 Hz), 7.18 (d, 2H, J=9 Hz), 7.56 (s, 1H), 7.62 (m, 1H), 7.78 (d, 1H, J=9 Hz), 7.80 (m, 1H), 8.00 (t, 2H, J=9 Hz), 8.41 (d. 1H, J=9 Hz), 13.16 (broad s, 1H). MS (DCI/NH$_3$) m/e: 419 (M+H)$^+$. Analysis calcd. for C$_{25}$H$_{26}$N$_2$O$_4$: C, 71.75; H, 6.26; N, 6.69. Found: C, 71.69; H, 6.50; N, 6.63.

EXAMPLE 41

Preparation of [2-phenyl-1-(4-(2-quinolylmethoxy)phenyl)eth-1-yl]-Z-2-iminoxy propionic acid.

The desired material was prepared according to the method of Example 2, except substituting benzylmagnesium chloride for cyclohexylmagnesium chloride and separating the mixture of isomers by chromatography as described in Example 38. m.p. 107°–108° C. $^1$H NMR (300 MHz, DMSO-d$_6$) δ 1.88 (s, 3H), 2.94 (dd, 1H, J= 15 and 7 Hz), 3.10 (dd, 1H, J=15 and 7 Hz), 5.19 (t, 1H, J=7 Hz), 5.34 (s, 2H), 7.00 (d, 2H, J=9 Hz), 7.15 (m, 7H), 7.62 (m, 1H), 7.68 (d, 1H, J=9 Hz), 8.00 (t, 2H, J=9 Hz), 8.42 (d, 1H, J=9 Hz). MS (DCI/NH$_3$) m/e 441 (M+H)$^+$. Analysis calcd. for C$_{27}$H$_{24}$N$_2$O$_4$.H$_2$O: C, 70.73; H, 5.72; N, 6.11. Found: C, 70.05; H, 5.49; N, 6.36.

EXAMPLE 42

Preparation of [2-phenyl-1-(4-(2-quinolylmethoxy)phenyl)eth-1-yl]-E-2-iminoxy propionic acid.

The desired compound was obtained from the reaction and chromatography described in Example 41. mp. 186–187° C. $^1$H NMR (300 MHz, DMSO-d$_6$) δ 1.94 (s, 3H), 3.07 (dd, 1H, J=15 and 7 Hz), 3.22 (dd, 1H, J=15 and 7 Hz), 5.35 (s+m, 3H), 7.02 (d, 2H, J=9 Hz), 7.21 (m, 7H), 7.62 (m, 1H), 7.68 (d, 1H, J=9 Hz), 7.98 (m, 1H), 8.00 (t, 2H, J=9 Hz), 8.42 (d, 1H, J=9 Hz). MS (DCI/NH$_3$) m/e441 (M+H)$^+$. Analysis calcd. for C$_{27}$H$_{24}$N$_2$O$_4$x0.5 H$_2$O: C, 72.15; H, 5.61; N, 6.23. Found: C, 72.58; H, 5.87; N, 6.01.

EXAMPLE 43

Preparation of
[2-thienyl-(4-(2-quinolylmethoxy)phenyl)methyl]-
E-2-iminoxy propionic acid.

The desired material was prepared according to the procedure of Example 2, except substituting 2-thienyllithium for cyclohexylmagnesium chloride. m.p. 72°–74 ° C. $^1$H NMR (300 MHz, DMSO-d$_6$) δ 2.03 (s, 3H), 5.38 (s, 2H), 6.57 (s, 1H), 6.98 (m, 2H), 7.10 (m, 2H), 7.36 (m, 2H), 7.51 (m, 1H), 7,63 (m, 1H), 7.69 (d, 1H, J=9 Hz), 7.80 (m, 1H), 8.00 (t, 2H, J=9 Hz), 8.42 (d, 1H, J=9 Hz). MS (DCI/NH$_3$) m/e 433 (M+H)$^+$. Analysis calcd. for C$_{24}$H$_{20}$N$_2$O$_4$S: C, 66.65; H, 4.66; N, 6.48. Found: C, 65.%; H, 4.44; N, 6.11.

EXAMPLE 44

Preparation of
[Cyclohexyl-(2-chloro4-(2-quinolylmethoxy)phenyl)-
methyl]-E-2-iminoxypropionic acid.

The desired material was prepared according to the procedure of Example 2, except substituting 2-chloro-4-(2-quinolylmethoxy)benzaldehyde for 4-(2-quinolylmethoxy)benzaldehyde. m.p. 153°–155° C. $^1$H NMR (300 MHz, DMSO-d$_6$) δ 1.14 (m, 5H), 1.41 (m, 1H), 1.65 (m, 3H), 1.80 (m, 2H), 2.00 (s, 3H), 5.30 (d, 1H, J=7 Hz), 5.39 (s, 2H), 7.07 (dd, 1H, J=9 and 3 Hz), 7.18 (d, 1H, J=3 Hz), 7.23 (d, 1H, J=9 Hz), 7.65 (m, 2H), 7.80 (m, 1H), 8.02 (t, 2H, J=9 Hz), 8.43 (d, 1H, J=9 Hz). MS (DCI/NH$_3$) m/e 467 (M+H)$^+$. Analysis calcd. for C$_{26}$H$_{27}$ClN$_2$O$_4$: C, 66.88; H, 5.83; N, 6.00. Found: C, 66.89; H, 5.89; N, 5.82.

EXAMPLE 45

Preparation of
[Cyclohexyl-(3-chloro-4-(2-quinolylmethoxy)phenyl)-
methyl]-E-2-iminoxypropionic acid.

The desired material was prepared according to the procedure of Example 2, except substituting 3-chloro-4-(2-quinolylmethoxy)benzaldehyde for 4-(2-quinolylmethoxy)benzaldehyde. m.p. 90°–92° C.; $^1$H NMR (300 MHz, DMSO-d$_6$) δ 1.10 (m, 5H), 1.36 (m, 1H), 1.70 (m, 5H), 2.00 (s, 3H), 4.94 (d, 1H, J=7 Hz), 5.46 (s, 2H), 7.18 (dd, 1H, J=7 and 2 Hz), 7.23 (d, 1H, J=7 Hz), 7.35 (d, 1H, J= 2 Hz), 7.62 (m, 1H), 7.72 (d, 1H, J=9 Hz), 7.80 (m, 1H), 8.02 (t, 2H, J=9 Hz), 8.45 (d, 1H, J=9 Hz). MS (DCI/NH$_3$) m/e 467 (M+H)$^+$. Analysis calcd. for C$_{26}$H$_{27}$ClN$_2$O$_4$: C, 66.88; H, 5.83; N, 6.00. Found: C, 67.03; H, 5.87; N, 5.82.

EXAMPLE 46

Preparation of
[Cyclohexyl-(2-chloro4-(2-quinolylmethoxy)phenyl)-
methyl]-Z-2-iminoxypropionic acid.

The desired material was prepared according to the procedure of Example 2, except substituting 3-chloro-4-(2-quinolylmethoxy)benzaldehyde for 4-(2-quinolylmethoxy)benzaldehyde. m.p. 182°–183° C. $^1$H NMR (300 MHz, DMSO-d$_6$) δ 1.04 (m, 5H), 1.33 (m, 1H), 1.60 (m, 4H), 1.82 (m, 1H), 1.88 (s, 3H), 4.74 (d, 1H, J=7 Hz), 5.46 (s, 2H), 7.13 (dd, 1H, J=7 and 2 Hz), 7.23 (d, 1H, J=7 Hz), 7.30 (d, 1H, J=2 Hz), 7.63 (m, 1H), 7.72 (d, 1H, J=9 Hz), 7.80 (m, 1H), 8.01 (t, 2H, J=9 Hz), 8.45 (d, 1H, J=9 Hz). MS (DCI/NH$_3$) m/e 467 (M+H)$^+$.

EXAMPLE 47

Preparation of
[3-methyl-3-phenyl-1-[4-(2-quinolylmethoxy)phenyl)-
but-1-yl]-Z- 2-iminoxypropionic acid.

The desired material was prepared according to the procedure of Example 2, except substituting 2-methyl-2-phenyl-1-propylmagnesium chloride for cyclohexylmagnesium chloride. m.p. 112°–113° C. $^1$H NMR (300 MHz, DMSO-d$_6$) δ 1.21 (s, 3H), 1.36 (s, 3H), 1.83 (9s, 3H), 2.00 (m, 2H), 4.65 (dd, 1H, J=7 and 3 Hz), 5.33 (s, (2H), 6.98 (m, 4H), 7.19 (m, 1H), 7.31 (m, 4H), 7.65 (m, 2H), 7.80 (m, 1H), 8.00 (t, 2H, J=9 Hz), 8.41 (d, 1H, J=9 Hz). MS (DCI/NH$_3$) m/e 483 (M+H)$^+$. Analysis calcd. for C$_{30}$H$_{30}$N$_2$O$_4$x1.5 H$_2$O: C, 70.71; H, 6.53; N, 5.50. Found: 70.72; H, 5.97; N, 5.39.

EXAMPLE 48

Preparation of
[3-methyl-3-phenyl-1-(4-(2-quinolylmethoxy)phenyl)-
but-1-yl]-E- 2-iminoxypropionic acid.

The desired material was prepared according to the procedure of Example 2, except substituting 2-methyl-2-phenyl-1-propylmagnesium chloride for cyclohexylmagnesium chloride. m.p. 137°–138° C. $^1$H NMR (300 MHz, DMSO-d$_6$) δ 1.30 (s, 3H), 1.34 (s, 3H), 1.73 (s, 3H), 2.00 (dd, 1H, J=15 and 3 Hz), 2.35 (dd, 1H, J=15 and 9 Hz), 4.96 (dd, 1H, J=9 and 3 Hz), 5.33 (s, 2H), 6.98 (d, 2H, J=9 Hz), 7.06 (d, 2H, J=9 Hz), 7.15 (m, 1H), 7.30 (m, 2H), 7.37 (m, 2H), 7.64 (m, 2H), 7.79 (m, 1H), 8.00 (t, 2H, J=9 Hz), 8.41 (d, 1H, J=9 Hz), 12.80 (broad s, 1H). MS (DCI/NH$_3$) m/e 483 (M+H)$^+$. Analysis calcd for C$_{30}$H$_{30}$N$_2$O$_4$: C, 74.67; H, 6.27; N. 5.80. Found: C, 74.07; H, 6.38; N, 5.64.

EXAMPLE 49

Preparation of
[3-methyl-3-phenyl-1-(4-(2-quinolylmethoxy)-
phenyl)but-1-yl]-E-2-iminoxyacetic acid.

The desired material was prepared according to the procedure of Example 1, except substituting 2-methyl-2-phenyl-1-propylmagnesium chloride for cyclohexylmagnesium chloride. m.p. 73°–75° C. $^1$H NMR (300 Mhz, DMSO-d$_6$) δ 1.25 (s, 3H), 1.34 (s, 3H), 2.05 (dd, 1H, J=15 and 3 Hz), 2.30 (rid, 1H, J=15 and 9 Hz), 4.87 (dd, 1H, J=9 and 3 Hz), 5.33 (s, 2H), 6.98 (d, 2H, J=9 Hz), 7.07 (d, 2H, J=9 Hz), 7.16 (m, 1H), 7.31 (m, 5H), 7.64 (m, 2H), 7.80 (m, 1H), 8.00 (t, 2H, J=9 Hz), 8.40 (d, 1H, J=9 Hz), 13.13 (broad s, 1H). MS (DCI/NH$_3$) m/e 469 (M+H)$^+$. Analysis calcd. for C$_{29}$H$_{28}$N$_2$O$_4$: C, 74.34; H, 6.02; N, 5.98. Found: C, 74.09; H, 6.32; N, 5.84.

EXAMPLE 50

Preparation of
[4-(2-quinolylmethoxy)phenylpent-1-yl]-E-2-
iminoxypropionic acid.

The desired material was prepared according to the procedure of Example 2, except substituting n-butylmagnesium chloride for cyclohexylmagnesium chloride. m.p. 118°–119° C. $^1$H NMR (300 MHz, DMSO-d$_6$) δ 0.85 (t, 3H, J=7 Hz), 1.25 (m, 4H), 1.73 (m, 1H), 1.90 (m, 1H), 1.96 (s, 3H), 5.13 (t, 1H, J=7 Hz), 5.36 (s, 2H), 7.04 (d, 2H, J=9 Hz), 7.25 (d, 2H, J=9 Hz), 7.62 (m, 1H), 7.68 (d, 1H, J= 9 Hz), 7.79 (m, 1H), 8.00 (t, 2H, J=9 Hz), 8.42 (d, 1H, J=9 Hz). MS (DCI/NH$_3$) m/e 407 (M+H)$^+$. Analysis calcd. for C$_{24}$H$_{26}$N$_2$O$_4$: C, 70.92; H, 6.45; N, 6.89; Found. C, 70.52; H, 6.73; N, 6.78.

EXAMPLE 51

Preparation of
[4-(2-quinolylmethoxy)phenyl)pent-1-yl]-E-iminoxyacetic acid.

The desired material was prepared according to the procedure of Example 1, except substituting n-butylmagnesium chloride for cyclohexylmagnesium chloride. m.p. 124°–126° C. $^1$H NMR (300 MHz, DMSO-d$_6$) δ 0.83 (t, 3H, J=7 Hz), 1.25 (m, 4H), 1.73 (m, 1H), 1.92 (m, 1H), 5.12 (t, 1H, J=7 Hz), 5.36 (s, 2H), 7.06 (d, 2H, J=9 Hz), 7.27 (d, 2H, J=9 Hz), 7.55 (s, 1H), 7.62 (m, 1H), 7.68 (d, 1H, J= 9 Hz), 7.78 (m, 1H), 8.01 (m, 2H), 8.42 (d, 1H, J=9 Hz). MS (DCI/NH$_3$) m/e 393 (M+H)$^+$.

EXAMPLE 52

Preparation of
[4-(2-quinolylmethoxy)phenyl)-but-3-en-1-yl]-E-iminoxy-2-propionic acid.

The desired material was prepared according to the procedure of Example 2, except substituting allylmagnesium chloride for cyclohexylmagnesium chloride. m.p. 123°–124° C. $^1$H NMR (300 MHz, DMSO-d$_6$) δ 1.97 (s, 3H), 2.57 (m, 1H), 2.60 (quintet, 1H, J=7 Hz), 5.03 (m, 2H), 5.22 (t, 1H, J=7 Hz), 5.36 (s, 2H), 5.70 (m, 1H), 7.05 (d, 2H, J=9 Hz), 7.27 (d, 2H, J=9 Hz), 7.62 (m, 1H), 7.68 (d, 1H, J=9 Hz), 7.80 (m, 1H), 8.00 (t, 2H, J=9 Hz), 8.42 (d, 1H, J=9 Hz). MS (DCI/NH$_3$) m/e 391 (M+H)$^+$. Analysis calcd. for C$_{23}$H$_{22}$N$_2$O$_4$: C, 70.75; H, 5.68; N, 7.17; Found. H, 70.36; H, 5.92; N, 7.01.

EXAMPLE 53

Preparation of
[Cyclohexyl-(4-(2-quinolylmethoxy)phenyl)methyl-E-2-iminoxy butanoic acid.

The desired material was prepared according to the procedure of Example 1, except substituting 2-ketobutyric acid for glyoxylic acid. m.p. 105° C. $^1$H NMR (300 MHz, DMSO-d$_6$) δ: 0.95 (m, 9H), 1.70 (m, 5H), 2.22 and 2.53 (two m, 1:2, 2H), 4.72 and 4.90 (two d, 1:2, 1H, J=9 Hz), 5.35 (s, 2H), 7.05 (m, 2H), 7.15 (m, 2H), 7.65 (m, 2H), 7.80 (m, 1H), 8.02 (t, 2H, J=9 Hz), 8.43 (d, 1H, J=9 Hz). MS (DCI/NH$_3$) m/e 447 (M+H)$^+$. Analysis calcd. for C$_{27}$H$_{30}$N$_2$O$_4$.H$_2$O: C, 69.81; H, 6.88; N, 6.03. Found: C, 70.00; H, 6.56; N, 5.50.

EXAMPLE 54

Preparation of
[Cyclohexyl-(4-(2-quinolylmethoxy)phenyl)methyl]-E-3-iminoxybutanoic acid.

The desired material was prepared according to the procedure of Example 2, except substituting 3-ketobutyric acid ethyl ester for pyruvic acid methyl ester. m.p. 85° C. $^1$H NMR (300 MHz, DMSO-d$_6$) δ 1.10 (m, 6H), 1.73 (m, 8H), 2.54 (m, 2H), 4.65 (d, 1H, J=9 Hz), 5.35 (s, 2H), 7.01 (m, 2H), 7.13 (m, 2H), 7.63 (m, 1H), 7.67 (d, 1H, J=9 Hz), 7.80 (m, 1H), 8.02 (t, 2H, J=9 Hz), 8.43 (d, 1H, J= 9 Hz). MS (DCI/NH$_3$) m/e 447 (M+H)$^+$. Analysis calcd. for C$_{27}$H$_{30}$N$_2$O$_4$.0.5H$_2$O: C, 71.26; H, 6.86; N, 6.15. Found: C, 71.51; H, 7.15; N, 5.87.

EXAMPLE 55

Preparation of
[Cyclohexyl-1-(4-(2-quinolylmethoxy)phenyl)-eth-2-yl]-2-iminoxy propionic acid.

Step 1: O-{1-(2-cyclohexyl-2-[4-(2-quinolylmethoxy)phenyl])ethyl}hydroxylamine.

The desired compound was prepared according to the method of Example 21, except substituting 2-cyclohexyl-2-(4-(2-quinolylmethoxy)phenyl)acetic acid for 3-cyclohexyl-2-(4-(2-quinolylmethoxy)phenyl)propionic acid.

Step 2: Cyclohexyl-1-(4-(2-quinolylmethoxy)phenyl)eth-2-yl]-2-iminoxy propionic acid.

The desired material was prepared according to the procedure of Example 22, except substituting O-{1-(2-cyclohexyl-2-[4-(2-quinolylmethoxy)phenyl] )ethyl}hydroxylamine for O-{1-(3-cyclohexyl-2-[4-(2-quinolylmethoxy)phenyl] )propyl}hydroxylamine. mp. 117°–118° C. $^1$H NMR (300 MHz, DMSO-d$_6$) δ 0.76 (m, 1H), 1.03 (m, 4H), 1.41 (m, 1H), 1.62 (m, 4H), 1.75 (s, 3H), 1.83 (m, 1H), 2.74 (q, 1H, J=6 Hz), 4.35 (dd, 1H, J=10 and 6 Hz) 4.48 (dd, 1H, J=10 and 6 Hz), 5.33 (s, 2H), 6.98 (d, 2H, J=9 Hz), 7.12 (d, 2H, J=9 Hz), 7.62 (m, 1H), 7.68 (d, 1H, J=9 Hz), 7.80 (m, 1H), 8.00 (t, 2H, J=9 Hz), 8.41 (d, 1H, J=9 Hz). MS (DCI/NH$_3$) m/e 447 (M+H)$^+$. Analysis calcd for C$_{27}$H$_{30}$N$_2$O$_4$: C, 70.80; H, 6.70; N, 6.27. Found: C,71.19; H, 6.86; N, 6.14.

EXAMPLE 56

Preparation of
[Cycloheptyl-(4-(2-quinolylmethoxy)phenyl)-eth-2-yl]-2-iminoxy propionic acid.

The desired material was prepared according to the procedure of Example 55, except substituting 2-cycloheptyl-2-(4-(2-quinolylmethoxy)phenyl)acetic acid for 2-cyclohexyl-2-(4-(2-quinolylmethoxy)phenyl)acetic acid. m.p. 68°–70° C. $^1$H NMR (300 MHz, DMSO-d$_6$) δ 1.06 (m, 1H), 1.25 (m, 2H), 1.50 (m, 8H), 1.74 (s, 3H), 1.79 (m, 2H), 2.84 (q, 1H, J=6 Hz), 4.36 (dd, 1H, J=10 and 6 Hz), 4.47 (dd, 1H, J=10 and 6 Hz), 5.33 (s, 2H), 6.98 (d, 2H, J=9 Hz), 7.13 (d, 2H, J=9 Hz), 7.62 (m, 1H), 7.68 (d, 1H, J=9 Hz), 7.78 (m, 1H), 8.00 (t, 2H, J=9 Hz), 8.42 (md, 1H, J=9 Hz). MS (DCI/NH$_3$) m/e 461 (M+H)$^+$.

EXAMPLE 57

Preparation of
[2-chloro-(4-(2-quinolylmethoxy)phenyl)methyl]-2-iminoxy propionic acid.

Step 1: O-(2-chloro-4-(2-quinolylmethoxy)phenylmethyloxime of pyruvic acid methyl ester.

To a solution of 2-chloro-4-(2-quinolylmethoxy)phenylmethanol (299 mg, 1.00 mmol)and triphenylphosphine (262 mg, 1.00 mmol) in THF (25 ml) was added dropwise at 0° C. under nitrogen a solution of DEAD (0. 16 ml, 1.00 mmol) and after 10 min. a solution of oxime of methyl pyruvate (117 mg, 1.00 mmol) in THF (5 ml). The mixture was stirred at room temperature for 2 hours and then concentrated in vacuo. The residue was chromatographed (silica gel, hexane-ethyl acetate 3:1) to provide 190 mg of O-(2-chloro-4-

(2-quinolylmethoxy)phenylmethyloxime of pyruvic acid methyl ester.

Step 2: [2-chloro-(4-(2-quinolylmethoxy)phenyl)methyl]-2-iminoxy propionic acid.

A mixture of the O-(2-chloro-4-(2-quinolylmethoxy)phenylmethyloxime of pyruvic acid methyl ester prepared in step 1, and 1N sodium hydroxide (1 ml) was stirred at room temperature for 2 hours and then concentrated in vacuo. To the residue was added water (20 ml) and the resulting solution was acidified with 10% citric acid to pH 3. The precipitated solid was filtered, dried in vacuo and crystallized from ethyl acetate-hexane to provide 150 mg of [2-chloro-(4-(2-quinolylmethoxy)phenyl)methyl] -2-iminoxy propionic acid. m.p. 169°–170° C. $^1$H NMR (300 MHz, DMSO-$d_6$) δ 1.94 (s, 3H), 5.22 (s, 2H), 5.42 (s, 2H), 7.07 (dd, 1H, J=9 and 3 Hz), 7.25 (d, 1H, J=3 Hz), 7.42 (d, 1H, J=9 Hz), 7.63 (m, 1H), 7.68 (d, 1H, J=9 Hz), 7.80 (m, 1H), 8.00 (m, 2H), 8.42 (d, 1H, J=9 Hz). MS (DCI/NH$_3$) m/e 385 (M+H)$^+$. Analysis calcd. for $C_{20}H_{17}ClN_2O_4$: C, 62.42; H, 4.45; N, 7.28. Found: C, 61.%; H, 4.10; N, 7.09.

EXAMPLE 58

Preparation of [Cycloheptyl-(4-(2-quinolylmethoxy)phenyl)methyl]-2-iminoxy propionic acid.

The desired material was prepared according to the procedure of Example 2, except substituting cycloheptylmagnesium chloride for cyclohexylmagnesium chloride. m.p. 88°–90° C. $^1$H NMR (300 MHz, DMSO-$d_6$) δ 1.47 (m, 13H), 1.98 (s, 3H), 5.00 (d, 1H, J=9 Hz), 5.33 (s, 2H), 7.03 (d, 2H, J=9 Hz), 7.21 (d, 2H, J=9 Hz), 7.62 (m, 1H), 7.68 (d, 1H, J=9 Hz), 7.78 (m, 1H), 8.01 (t, 2H, J=9 Hz), 8.41 (d, 1H, J=9 Hz). MS (DCI/NH$_3$) m/e 447 (M+H)$^+$. Analysis calcd. for $C_{27}H_{30}N_2O_4 \cdot 0.5 H_2O$: C, 71.18; H, 6.86; N, 6.15. Found: C, 71.35; H, 6.71; N, 6.07.

EXAMPLE 59

Preparation of [Cyclohexyl-(4-(4-thiazolylmethoxy)phenyl)methyl]-2-iminoxy propionic acid.

The desired material was prepared according to the procedure of Example 2, except substituting 4-chloromethylthiazole for 2-chloromethylquinoline. m.p. 157 ° C. $^1$H NMR (300 MHz, DMSO-$d_6$) δ 1.12 (m, 6H), 1.72 (m, 5H), 2.0 (s, 2H), 4.93 (d, 1H, J=9 Hz), 5.20 (s, 2H), 7.01 (d, 2H, J=9 Hz), 7.18 (d, 2H, J=9 Hz), 7.78 (d, 1H, J=1.5 Hz), 9.13 (d, 1H, J=1.5 Hz). MS (DCI/NH$_3$) m/e 389 (M+H)$^+$. Analysis calcd. for $C_{20}H_{24}N_2O_4S$: C, 61.83; H, 6.23; N, 7.21. Found: C, 61.33; H, 6.26; N, 7.09.

EXAMPLE 60

Preparation of [Cyclohexyl-(4-(4-thiazolylmethoxy)phenyl)methyl]-iminoxyacetic acid.

The desired material was prepared according to the procedure of Example 1, except substituting 2-chloromethylthiazole for 2-chloromethylquinoline. m.p. 159°– 160° C. $^1$H NMR (300 MHz, DMSO-$d_6$) δ 1.11 (m, 6H), 1.71 (m, 5H), 4.92 (d, 1H, J=9 Hz), 5.21 (s, 2H), 7.03 (d, 2H, J=9 Hz), 7.19 (d, 2H, J=9 Hz), 7.60 (s, 1H), 7.78 (d, 1H, J=1.5 Hz), 9.13 (d, 1H, J=1.5 Hz), 13.70 (broad s, 1H). MS (DCI/NH$_3$) m/e 375 (M+H)$^+$. Analysis calcd. for $C_{19}H_{22}N_2O_4S$: C, 60.94; H, 5.92; N, 7.48. Found: C, 61.17; H, 6.05; N, 7.40.

EXAMPLE 61

Preparation of Sodium [Cyclohexyl-(4-(2-quinolylmethoxy)phenyl)methyl]-2-iminoxypropionate.

To a solution of cyclohexyl-(4-(2-quinolylmethoxy)phenyl)methyl)-2-iminoxy propionic acid (300 mg; 0.69 mmol), prepared as in Example 2, in a mixture of THF and ethanol (15 ml, 1:1) at room temperature was added 1.0N NaOH (0.69 ml; 0.69 mmol), and the resulting mixture was stirred at room temperature for 1 hour. The solvents were removed in vacuo, and the residue was diluted with water, at which point the desired material precipitated. The solid was filtered and washed several times with copious quantities of water. Some foaming ocurred on filtration. The remaining solid was dried in vacuo for 5 hours to give 100 mg of Sodium [Cyclohexyl-(4-(2-quinolylmethoxy)phenyl)methyl]-2-iminoxypropionate as a white powder. m.p. 138°–150° C. $^1$H NMR (300 MHz, DMSO-$d_6$) δ 1.02 (m, 5H), 1.36 (m, 1H), 1.61 (m, 4H), 1.84 (m, 1H), 1.89 (s, 3H), 4.74 (d, 1H, J=9Hz), 5.34 (s, 2H), 7.0 (d, 2H, J=9Hz), 7.13 (d, 2H, J=9Hz), 7.62 (m, 1H), 7.68 (d, 1H, J= 9Hz), 7.79 (m, 1H), 8.0 (t, 2H, J=9Hz), 8.40 (d, 1H, J=9Hz). MS (FAB(+)) m/e471 (M+K), (FAB(-)) m/e431 (M–1).

EXAMPLE 62

Preparation of (R)-[Cyclopentyl-(4-2-quinolylmethoxy)phenyl)-methyl]-E-2-iminoxypropionic acid.

Step 1: 2-cyclopentyl-2-(4-(2-quinolylmethoxy)phenyl)acetic acid methyl ester.

To a mixture of 4-(2-quinolylmethoxy)phenylacetic acid methyl ester (6.36 g; 20.7 mmol) in DMF (10 ml) at 0° C. was added in portions sodium hydride (60% dispersion in mineral oil) (840 mg; 21 mmol). The mixture was stirred at room temperature for 1 hour. It was then recooled to 0° C. and cyclopentyl bromide (2.38 ml, 22.0 mmol) was added dropwise. The resulting mixture was stirred at room temperature for 18 hours, and was then poured into water (50 ml). The product was extracted with ethyl acetate and purified by silica gel chromatography (hexane-ethyl acetate 3:1) to provide 5.5 g of 2-cyclopentyl-2-(4-(2-quinolylmethoxy)phenyl)acetic acid methyl ester.

Step 2: 2-cyclopentyl-2-(4-(2-quinolylmethoxy)phenyl)acetic acid.

To a solution of the 2-cyclopentyl-2-(4-(2-quinolylmethoxy)phenyl)acetic acid methyl ester prepared in step 1 in methanol (100 ml) was added dropwise 1N sodium hydroxide (25 ml) and the resulting mixture was refluxed at 50° C. for 16 hours. The reaction mixture was then cooled to room temperature, and the methanol was removed in vacuo. The residue was acidified with 10% citric acid and the resulting solid was filtered, washed with water and dried in vacuo to provide 4.8 g of 2-cyclopentyl-2-(4-(2-quinolylmethoxy)phenyl)acetic acid.

Step 3: 2-(R)- and (S)-cyclopentyl-2-(4-(2-quinolylmethoxy)phenyl)acetic acid (2-hydroxy- 2-(S)-phenyl)eth-1-yl amide.

To a solution of 2-cyclopentyl-2-(4-(2-quinolylmethoxy)phenyl)acetic acid (4.73 g, 13.1 mmol), prepared as in step 2, and (S)-phenylglycinol (2.17 g, 15.8 mmol) in DMF (65 ml) at −10 to −15° C. was added dropwise a solution of diphenylphosphoryl azide (3.51 ml, 15.8 mmol) in DMF (15 ml) followed by addition of triethylamine (4.4 ml, 31.6 mmol). The mixture was stirred at that temperature for 16 hours. The reaction mixture was then poured into ice-water, and the precipitated solid was filtered, washed with water and dried in vacuo. Crystallization three times from ethanol gave 1.9 g of 2-(R)-cyclopentyl-2-(4-(2-quinolnylmethoxy)phenyl)acetic acid (2-hydroxy-1-(S)-phenyl)eth-1-yl amide. The mother liquors were concentrated and recrystallized from methylene chloride (three times) to provide 1.3 g of 2-(S)-cyclopentyl-2-(4-(2-quinolylmethoxy)phenyl)acetic acid (2-hydroxy-2-(S)-phenyl)eth-1-yl amide.

Step 4: 2-(R)-cyclopentyl-2-(4-(2-quinolylmethoxy)phenyl)acetic acid.

A mixture of (R) cyclopentyl-2-(4-(2-quinolnylmethoxy)phenyl)acetic acid (2-hydroxy- 1-(S)-phenyl)eth-1-yl amide (1.87 g, 3.9 mmol), prepared as in step 3, and 20 ml of 5N sulfuric acid in dioxane (20 ml) was refluxed for 24 hours. The reaction mixture was then cooled to room temperature and pH was adjusted to 3 by addition of 2N sodium hydroxide. The solid was filtered, washed with water, dried in vacuo, and crystallized from ethanol to afford 800 mg of 2-(R)-cyclopentyl-2-(4-(2-quinolylmethoxy)phenyl)acetic acid. The SS-diastereoisomer (1.35 g, 2.8 mmol) and 5N sulfuric acid (15 ml) in dioxane (15 ml) was refluxed for 24 hours. Work-up as above afforded 600 mg of 2-(S)-cyclopentyl-2-(4-(2-quinolylmethoxy)phenyl)acetic acid.

Step 5: 2-(R)-cyclopentyl-2-(4-(2-quinolylmethoxy)phenyl)ethan-1-ol.

To a solution of 2-(R)-cyclopentyl-2-(4-(2-quinolylmethoxy)phenyl)acetic acid (290 mg, 0.8 mmol), prepared as in step 4, and triethylamine (0.14 ml, 1.0 ml) in THF (35 ml) at −25° C. was added dropwise ethyl chloroformate (0.1 ml, 1.0 mmol). Upon completion of addition, the mixture was stirred for 15 min. and warmed to 0° C. Sodium borohydride (150 mg, 4.0 mmol) was added followed by very slow addition of methanol (15 ml). The reaction was quenched with saturated aqueous $NH_4Cl$ and extracted with ethyl acetate. The organic layer was washed with water and brine, dried over $MgSO_4$, and concentrated in vacuo. The residue was chromatographed (silica gel, hexane-ethyl acetate 2:1) to afford 180 mg of 2-(R)-cyclopentyl- 2-(4-(2-quinolylmethoxy)phenyl)ethan-1-ol.

Step 6: N-phthaloyl-O-(2-(R)-cyclopentyl-2-(4-(2-quinolylmethoxy)phenyl)eth-1-yl) hydroxylamine.

To a solution of 2-(R)-cyclopentyl-2-(4-(2-quinolylmethoxy)phenyl)ethan-1-ol (180 mg, 0.51 mmol), prepared in step 5, triphenylphosphine (262 mg, 1.00 mmol) and N-hydroxyphthalimide (85 mg, 0.52 mmol) in THF (30 ml) was added dropwise a solution of DEAD (0.16 ml, 1.0 mmol) in THF (5 ml), and the reaction mixture was left at room temperature for 12 hours. The mixture was concentrated in vacuo and the residue was chromatographed (silica gel, hexane-ethyl acetate 2:1) to give 240 mg of N-phthaloyl-O-(2-(R)-cyclopentyl-2-(4-(2-quinolylmethoxy) phenyl)eth-1-yl) hydroxylamine.

Step 7: 0-(2-(R)-cyclopentyl-2-(4-(2-quinolylmethoxy)phenyl)eth-1-yl) hydroxylamine.

A mixture of N-phthaloyl-O-(2-(R)-cyclopentyl-2-(4-(2-quinolylmethoxy) phenyl)eth-1-yl) hydroxylamine (200 mg, 0.41 mmol), prepared in step 7, and hydrazine hydrate (0.06 ml, 1.0 mmol) in ethanol (15 ml) was refluxed for 30 min. 10% aqueous $Na_2CO_3$ was added and the mixture was extracted with ethyl acetate to afford 130 mg of O-(2-(R)-cyclopentyl-2-(4-(2-quinolylmethoxy)phenyl)eth-1-yl) hydroxylamine.

Step 8: 0-(2-(R)-cyclopentyl-2-(4-(2-quinolylmethoxy)phenyl)eth-1-yl)oxime of propionic acid methyl ester.

To a mixture of the O-(2-(R)-cyclopentyl-2-(4-(2-quinolylmethoxy) phenyl)eth-1-yl) hydroxylamine prepared in step 7 in dioxane-methanol (1:1, 30 ml) were added methyl pyruvate (0.1 ml, 1.0 mmol) and acetic acid (0.03 ml, 0.5 mmol), and the resulting mixture was stirred at room temperature for 12 hours. The organics were removed in vacuo, and the residue was dissolved in ethyl acetate. The organic phase was washed with water, 10% sodium bicarbonate, and brine, dried over $MgSO_4$, and concentrated in vacuo. The residue was chromatographed (silica gel, hexane-ethyl acetate 3:1) to afford 30 mg of O-(2-(R)-cyclopentyl-2-(4-(2-quinolylmethoxy)phenyl)eth- 1-yl)oxime of pyruvic acid methyl ester.

Step 9: (R)-[Cyclopentyl-(4-(2-quinolylmethoxy)phenyl)methyl]-E-2-iminoxypropionic acid.

To a solution of the O-(2-(R)-cyclopentyl-2-(4-(2-quinolylmethoxy)phenyl)eth- 1-yl)oxime of pyruvic acid methyl ester prepared in step 8 in dioxane-methanol (1:1, 10 ml) was added 1N sodium hydroxide (0.1 ml), and the mixture was stirred at 50° C. for 2 hours. The reaction mixture was then concentrated in vacuo, and the residue was diluted with water (5 ml) and acidified to pH 3. Extraction with ethyl acetate afforded 20 mg of (R)-[Cyclopentyl-(4-(2-quinolylmethoxy)phenyl)methyl] -E-2-iminoxypropionic acid. m.p 60°–62° C., αD= −25.5 (c=2.2, $CHCl_3$). $^1$H NMR (300 MHz, $CDCl_3$) δ 1.03 (m, 1H),1.26 (m, 1H), 1.57 (m, 5H), 1.90 (s+m, 4H), 2.10 (m, 1H), 2.70 (m, 1H), 4.38 (dd, 1H, J= 10 and 7 Hz), 4.50 (dd, 1H, J=10 and 4 Hz), 5.38 (s, 2H), 6.94 (d, 2H, J= 9 Hz), 7.08 (d, 2H, J=9 Hz), 7.55 (m, 1H), 7.70 (m, 2H), 7.83 (m, 1H), 8.09 (d, 1H, J= 9 Hz), 8.20 (d, 1H, J=9 Hz). MS (DCI/$NH_3$) m/e 433 (M+H)$^+$. Analysis calc'd for $C_{26}H_{28}N_2O_4$: C, 72.20; H, 6.53; N, 6.48. Found: C, 72.22; H, 6.76; N, 6.46.

EXAMPLE 63

Preparation of
(S)-[Cyclopentyl-(4-(2-quinolylmethoxy)phenyl)methyl]-E-2-iminoxypropionic acid.

The desired material was prepared acording to the procedure of Example 62, steps 4–9, except substituting 2-(S)-cyclopentyl-2-(4-(2-quinolylmethoxy)phenyl)acetic acid for 2-(R)-cyclopentyl-2-(4-(2-quinolylmethoxy)phenyl)acetic acid. m.p 63°–65° C. αD=+23.7 (c=1.9, $CHCl_3$). $^1$H NMR (300 MHz, $CDCl_3$) δ 1.00 (m, 1H), 1.25 (m, 1H), 1.57 (m, 5H), 1.89 (s+m, 4H), 2.05 (m, 1H), 2.68 (m, 1H), 4.35 (m, 1H), 4.49 (m, 1H), 5.36 (s, 2H), 6.93 (d, 2H, J=9 Hz), 7.06 (d, 2H, J=9 Hz), 7.55 (m, 1H), 7.70 (m, 2H), 7.82 (m, 1H), 8.09 (d, 1H, J=9 Hz), 8.20 (d, 1H, J=9 Hz). MS (DCI/$NH_3$) m/e 433 (M+H)$^+$. Analysis calc'd for $C_{26}H_{28}N_2O_4$: C, 72.20; H, 6.53; N, 6.48. Found: C, 72.22; H, 6.76; N, 6.46.

EXAMPLE 64

Preparation of
[Cyclohexyl-(4-(2-quinolylmethoxy)benzo[b]thien-2-yl)methyl]-2-iminoxypropionic acid.

Step 1: 2-nitro-5-(2-quinolylmethoxy)benzyl alcohol.

A mixture of 5-hydroxy-2-nitrobenzyl alcohol (5.1 g, 30 mmol), tetraethylammonium fluoride hydrate (8.94 g, 60 mmol) and 2-chloromethylquinoline (5.31 g, 30 mmol) in DMF (90 ml) was stirred at room temperature for 72 hours. The reaction mixture was then poured into water and extracted with ethyl acetate. The extract was dried over $MgSO_4$ and concentrated in vacuo. To the residue was added methylene chloride (25 ml) and the solid was filtered to provide 3.1 g of 2-nitro-5-(2-quinolylmethoxy)benzyl alcohol.

Step 2: 2-nitro-5-(2-quinolylmethoxy)benzaldehyde.

To a solution of 2-nitro-5-(2-quinolylmethoxy)benzyl alcohol (1.74 g, 5.6 mmol), prepared in step 1, and dicyclohexylcarbodiimide (3.71 g, 18 mmol) in DMSO (25 ml) was added 1M solution of phosphoric acid in DMSO (2.7 ml), and the resulting mixture was stirred at room temperature for 1 hour. Ethyl acetate (100 ml) was then added and the precipitated dicyclohexylurea was filtered off. The filtrate was washed with water, and brine, dried over $MgSO_4$, and concentrated in vacuo. The residue was chromatographed (silica gel, methylene chloride-ethyl acetate 15:1) to afford 1.25 g of 2-nitro-5-(2-quinolylmethoxy)benzaldehyde.

Step 3: ethyl 5-(2-quinolylmethoxy)benzo[b]thiophene-2-carboxylate.

To a solution of 2-nitro-5-(2-quinolylmethoxy)benzaldehyde (1.24 g, 4 mmol), prepared in step 2, and potassium carbonate (700 mg, 5.0 mmol) in DMF (15 ml) was added dropwise ethyl thioglycolate (0.46 ml, 4.0 mmol), and the resulting mixture was stirred at room temperature for 16 hours. The reaction mixture was then poured into ice-water and extracted with ethyl acetate. The organic extract was washed with water, and brine, dried over $MgSO_4$, and concentrated in vacuo. The residue was chromatographed (silica gel, methylene chloride-ethyl acetate 24:1) to provide 480 mg of ethyl 5-(2-quinolylmethoxy)benzo[b]thiophene-2-carboxylate.

Step 4: 5-(2-quinolylmethoxy)benzo[b]tiophene-2-carboxylic acid.

A mixture of ethyl 5-(2-quinolylmethoxy)benzo[b]thiophene-2-carboxylate (472 mg; 1.3 mmol), prepared as in step 3, and 1N sodium hydroxide (1.5 ml, 1.5 mmol) in dioxane (15 ml) and methanol (10 ml) was stirred at room temperature for 8 hours. The organics were then removed in vacuo and the residue was acidified to pH 3 to provide 440 mg of 5-(2-quinolylmethoxy)benzo[b]tiophene-2-carboxylic acid.

Step 5: 5-(2-quinolylmethoxy)benzo[b]thiophene-2-carboxylic acid N-methyl-O-methyl amide.

To a mixture of 5-(2-quinolylmethoxy)benzo[b]thiophene-2-carboxylic acid (440 mg, 1.3 mmol), prepared in step 4, N-methyl-O-methylhydroxylamine hydrochloride (146 mg, 1.5 mmol), pyridine (0.122 ml, 1.5 mmol) and carbon tetrabromide (497 mg, 1.5 mmol) in methylene chloride (25 ml) and THF (15 ml) was added triphenylphosphine (393 mg, 1.5 mmol) in portions. The mixture was stirred at room temperature for 60 min and concentrated in vacuo. The residue was chromatographed (methylene chloride-ethyl acetate 9:1) to afford 470 mg of 5-(2-quinolylmethoxy)benzo[ b]thiophene-2-carboxylic acid N-methyl-O-methyl amide.

Step 6: 5-(2-quinolylmethoxy)benzo[b]thiophene-2-carbaldehyde.

To a solution of 5-(2-quinolylmethoxy)benzo[b]thiophene-2-carboxylic acid N-methyl-O-methyl amide (470 mg; 1.26 mmol), prepared in step 5, in THF (20 ml) at −78° C. was added 1N DIBAL in THF (1.5 ml, 1.5 mmol). The reaction mixture was stirred at room temperature for 18 hours, and an additional 1.5 mL of DIBAL was added. The reaction mixture was stirred for 15 hours and 3 mL of DIBAL was added. After stirring for 12 hours, the reaction was quenched with saturated aqueous $NH_4Cl$. The mixture was extracted with ethyl acetate, and the organic phase was dried over $MgSO_4$ and concentrated in vacuo. The residue was chromatographed (silica gel, methylene chloride-ethyl acetate 9:1) to give 100 mg of 5-(2-quinolylmethoxy)benzo[b]thiophene-2-carbaldehyde.

Step 7: O-[cyclohexyl-(4-(2-quinolylmethoxy)benzo[b]thienyl)methyl]hydroxylamine.

The desired compound was prepared according to the method of Example 1, steps 2–4, except substituting 5-(2-quinolylmethoxy)benzo[b]thiophene-2-carbaldehyde, prepared as in step 6, for 4-(2-quinolylmethoxy)benzaldehyde.

Step 8: [Cyclohexyl-(4-(2-quinolylmethoxy)benzo[b]thien-2-yl)methyl]-2-iminoxypropionic acid.

The desired material was prepared according to the procedure of Example 2, except substituting O-[cyclohexyl-(4-(2-quinolylmethoxy)benzo[ b]thienyl)methyl]hydroxylamine for O-[cyclohexyl-(4-(2-quinolylmethoxy)phenyl)methyl] hydroxylamine. m.p. 91°–93° C. (methanol-water). $^1H$ NMR (300 MHz, DMSO-$d_6$) δ 1.18 (m, 6H), 1.44 (m, 1H), 1.63 (m, 3H), 1.92 (m, 1H), 2.00 (s, 3H), 5.30 (d, 1H, J=7 Hz), 5.43 (s, 2H), 7.11 (d-d, 1H, J=9 and 3 Hz), 7.25 (s, 1H), 7.48 (d, 1H, J=3 Hz), 7.62 (m, 1H), 7.70 (d, 1H, J=9 Hz), 7.80 (m, 2H), 8.01 (m, 2H), 8.42 (d, 1H, J=9 Hz), 13.05 (broad s, 1H). MS (DCI/$NH_3$) m/e 489 (M+H)$^+$.

EXAMPLE 65

Preparation of
[Cyclohexyl-(6-(2-quinolylmethoxy)pyrid-3-yl)-methyl]iminoxy acetic acid.

Step 1: 6-hydroxynicotinic acid methyl ester.

To a suspension of 6-hydroxynicotinic acid (20.0 g, 0.144 mol) in methanol as (350 ml) at room temperature was added concentatrated sulfuric acid (9.98 ml, 0.179 mol) and the mixture was refluxed with vigorous stirring for 16 hours. Much of the organic solvent was removed in vacuo. The remaining residue was neutralized with saturated aqueous $NaHCO_3$, and the product was extracted from the aqueous phase with ethyl acetate. The organic layer was dried over $MgSO_4$ and concentrated in vacuo to give 11.50 g of 6-hydroxynicotinic acid methyl ester as a creamish powder.

Step 2: 6-(quinol-2-ylmethoxy)nicotinic acid methyl ester.

To a solution of 6-hydroxynicotinic acid methyl ester (10.0g, 0.0652 mol), prepared as in step 1, in DMF (350 ml) at room temperature was added anhydrous $K_2CO_3$ (19.0 g, 0.137 mol) followed by 2-chloromethylquinoline hydrochloride (14.0 g, 0.0652 mol), and the mixture was allowed to stir at room temperature overnight. Once the starting material was consumed, water (700 ml) was added to the mixture, and the aqueous layer was extracted with ethyl acetate. The organic layer was washed with brine, dried over $MgSO_4$, and concentrated in vacuo. The resulting white precipitate was filtered and washed with hexanes to give 15.20 g of 6-(quinol- 2-ylmethoxy)nicotinic acid methyl ester.

Step 3: 6-(2-quinolylmethoxy)nicotinic acid.

To a solution of 6-(quinol-2-ylmethoxy)nicotinic acid methyl ester (5.06 g, 17.2 mmol), prepared as in step 2, in methanol (100 ml) at room temperature with stirring was added. 1N NaOH (18.9 ml, 18.9 mmol). The resulting mixture was allowed to stir at room temperature for 14 hours. The mixture was then refluxed for 3 hours, cooled to room temperature and concentrated in vacuo. The residue was diluted with water and the aqueous layer was extracted with ethyl acetate. The aqueous layer was acidified to pH 3 with 10% citric acid to give a white precipitate. The precipitate was filtered and washed with water and diethyl ether. The solid was dried overnight at 80° C. under reuced pressure to give 4.46 g of 6-(2-quinolylmethoxy)nicotinic acid.

Step 4: 6-(2-quinolylmethoxy)pyrid-3-ylmethanol.

To a solution of 6-(2-quinolylmethoxy)nicotinic acid (4.38 g, 1.56 mmol), prepared as in step 3, and triethylamine (0.228 ml, 1.64 mmol) in THF (80 ml) at −10 ° C. to −5° C. was added dropwise a solution of ethyl chloroformate (1.57 ml, 1.64 mmol) in THF (5 ml), and the reaction mixture was stirred at 0° C. for 1 hour. Precipitated triethylamine hydrochloride was filtered and washed with THF. The combined filtrate and washings were placed in an addition funnel and added dropwise to a mixture of sodium borohydride (1.50g, 3.91 mmol) in water (20 ml) at 0° C. When the bubbling ceased, the mixture was allowed to warm to room temperature and stir for 2 hours. 10% Citric acid added to bring the mixture to pH 3 and the aqueous layer was extracted with ethyl acetate. The organic extract was washed with 1N NaOH, water, and brine, and dried over $MgSO_4$. The solvent was removed in vacuo and the residue treated with ethyl acetate-hexane to precipitate the product, 3.44 g of 6-(2-quinolylmethoxy)pyrid-3-ylmethanol.

Step 5: 6-(2-quinolylmethoxy)pyrid-3-yl carboxaldehyde.

To a solution of oxalyl chloride (0.363 ml, 4.13 mmol) in methylene chloride (10 ml) at −65° C. was added dropwise DMSO (0.587 ml, 8.27 mmol), and mixture was stirred for 5 minutes. Then 6-(2-quinolylmethoxy)pyrid-3-ylmethanol (1.00 g; 2.76 mmol), prepared as in step 4, was added slowly. After 15 minutes, triethylamine (2.62 ml, 18.8 mmol) was added and stirring was continued for an additional 10 minutes. The reaction was warmed slowly to room temperature and quenched with brine. The aqueous layer was extracted with methylene chloride. The organic layer was dried over $MgSO_4$ and concentrated in vacuo. The residue was precipitated with ethyl acetate and filtered to give 6-(2-quinolylmethoxy)pyrid-3-yl carboxaldehyde (990 mg).

Step 6: cyclohexyl-(6-(quinolin-2-ylmethoxy)pyridin-3-yl)-methanol.

A solution of 6-(2-quinolylmethoxy)pyrid-3-yl carboxaldehyde (0.979 g; 3.71 mmol), prepared as in step 5, in anhydrous THF (15 ml) was cooled to −78° C. and cyclohexylmagnesium chloride (2M sol'n, 3.89 ml, 7.79 mmol) was added dropwise via syringe. After 3 hours, the reaction mixture was allowed to warm to room temperature and stir for an additional hour. Saturated aqueous $NH_4Cl$ was added to the mixture and the organics were removed in vacuo. The aqueous layer was extracted with ethyl acetate. The organic extract was washed with 10% citric acid, water, and brine, dried over $MgSO_4$ and concentrated in vacuo. The residue was purified by silica gel flash chromatography (chloroform followed by 5% methanol in chloroform) to afford 297 mg of cyclohexyl-(6-(quinolin-2-ylmethoxy)pyridin-3-yl)-methanol.

Step 7: N-phthaloyl-O-(cyclohexyl-(6-(2-quinolylmethoxy)pyrid-3-yl)methyl)hydroxylamine.

To a solution of cyclohexyl-(6-(quinolin-2-ylmethoxy)pyridin-3-yl)-methanol (0.243 g, 0.689 mmol), prepared as in step 6, triphenylphosphine (0.363 g, 1.38 mmol), and N-hydroxyphthalimide (0.123 g, 0.759 mmol) in anhydrous THF (10 ml) under nitrogen at 0° C. was added diethyl azodicarboxylate (0.217 ml, 1.38 mmol) in THF (10 ml) over a one hour. The mixture was then allowed to warm to room temperature and stir for 2 hours. The solvent was removed in vacuo and the residue was subjected to silica gel flash chromatography (1% acetic acid in ethyl acetate-hexane 4:1, followed by 5% acetic acid in ethyl acetate-hexane 4:1) to give a mixture of the desired N-phthaloyl-O-(cyclohexyl-(6-(2-quinolylmethoxy)pyrid-3-yl)methyl)hydroxylamine and triphenylphosphine oxide (230 mg total material).

Step 8: O-(cyclohexyl-(6-(2-quinolylmethoxy)pyrid-3-yl)methyl)hydroxylamine.

The above crude N-phthaloyl-O-(cyclohexyl-(6-(2-quinolylmethoxy)pyrid-3-yl)methyl)hydroxylamine (0.205 g, 0.416 mmol), prepared in step 7, was dissolved in a mixture of methylene chloride and ethanol (1:1, 4 ml) and was treated with hydrazine hydrate (0.05 ml, 1.04 mmol) for one hour at reflux. The mixture was cooled to room temperature and 10% aqueous $Na_2CO_3$ was added to dissolve precipitated solid. The aqueous layer was extracted with ethyl acetate. The organic extract was washed with water and brine, dried over $MgSO_4$, and concentrated in vacuo to provide O-(cyclohexyl-(6-(2-quinolylmethoxy)pyrid-3-yl)methyl) hydroxylamine which was used without further purification.

Step 9: [Cyclohexyl-(6-(2-quinolylmethoxy)pyrid-3-yl)methyl]iminoxy acetic acid.

A mixture of tO-(cyclohexyl-(6-(2-quinolylmethoxy)pyrid-3-yl)methyl) hydroxylamine (0.198 g, 0.545 mmol), prepared in step 8, sodium acetate trihydrate (0.074 g, 0.545 mmol) and glyoxylic acid (0.055 g, 0.60 mmol) in ethanol-dioxane-water (2:1:1, 4 ml) was allowed to stir at room temperature overnight. The solvent was then removed in vacuo, and the residue was treated with 15% NaOH and extracted with ethyl acetate. The aqueous layer was acidified with 10% citric acid to pH 3 and extracted with ethyl acetate. The organic layer was then dried over $MgSO_4$ and concentrated in vacuo. The residue was treated with diethyl ether and the resulting precipitate was filtered and washed with diethyl ether to afford 60 mg of [Cyclohexyl-(6-(2-quinolylmethoxy)pyrid-3-yl)methyl]iminoxy acetic acid as a white powder. m.p. 175°–178° C. $^1$H NMR (300 MHz, DMSO-$d_6$) δ 0.88–1.32 (m, 5H), 1.46–1.56 (m, 1H), 1.58–1.87 (m, 4H), 1.90–2.0 (m, 1H), 4.78 (d, 1H, J=9 Hz), 5.30–5.47 (m, 2H), 6.43 (d, 1H, J=9 Hz), 7.38 (d, 1H, J=9 Hz), 7.43 (dd, 1H, J= 9, 3 Hz), 7.53–7.62 (m, 2H), 7.69–7.77 (m, 1H), 7.78–7.86 (m, 2H), 7.95 (dd, 1H, J=9, 3 Hz), 8.33 (d, 1H, J=9 Hz), 13.23 (br s, 1H). MS (DCI/$NH_3$) m/e 420 (M+H)$^+$. Analysis calculated for:$C_{24}H_{25}N_3O_4 \cdot 0.30\, H_2O$: C, 67.85; H, 6.07; N, 9.89. Found: C, 67.83; H, 6.28; N, 9.49.

EXAMPLE 66

Preparation of [Cyclohexyl-(4-(2-benzothiazolylmethoxy)phenyl)-methyl]iminoxy acetic acid.

The desired material was prepared according to the procedure of Example 1, except substituting 2-chloromethylbenzothiazole for 2-chloromethylquinoline. m.p. 179° C. $^1$H NMR (300 MHz, DMSO-$d_6$) δ 1.05 (m, 6H), 1.75 (m, 5H), 4.91 (d, 1H, J=9 Hz), 5.60 (s, 2H), 7.08 (d, 2H, J=9 Hz), 7.21 (d, 2H, J=9 Hz), 7.50 (m, 3H), 8.02 (m, 1H), 8.13 (m, 1H). MS (DCI/$NH_3$) m/e 425 (M+H)$^+$. Analysis calcd. for $C_{23}H_{24}N_2O_4S$: C, 65.06; H, 5.70; N, 6.59. Found: C, 65.78; H, 5.78; N, 6.37.

EXAMPLE 67

Preparation of
[Cyclohexyl-(4-(6-(4-fluorophenoxy)pyrid-2-ylmethoxy)phenyl) methyl]iminoxyacetic acid.

The desired material was prepared according to the procedure of Example 2, except substituting 4-(6-(4-fluorophenoxy)pyrid-2-ylmethoxy)benzaldehyde for 4-( 2-quinolylmethoxy)benzaldehyde. m.p. 54°–57° C. $^1$H NMR (300 MHz, DMSO-$d_6$) δ 1.10 (m, 5H), 1.35 (m, 1H), 1.70 (m, 5H), 1.99 (s, 3H), 4.91 (d, 1H, J= 7 Hz), 4.98 (s, 2H), 6.94 (m, 3H), 7.20 (m, 7H), 7.88 (s, 1H). MS (DCI/NH$_3$) m/e 510 (M+NH$_4$)$^+$, 493 (M+H)$^+$.

EXAMPLE 68

Preparation of
[Cyclohexyl-(4-(1-methyl-2-benzimidazolylmethoxy)-phenyl) methyl]- 2-iminoxypropionic acid.

The desired material was prepared according to the procedure of Example 2, except substituting 2-chloromethyl-1-methylbenzimidazole for 2-chloromethylquinoline. mp. 190–192° C. $^1$H NMR (300 MHz, DMSO-$d_6$) δ 1.10 (m, 5H), 1.35 (m, 1H), 1.71 9m, 5h), 1.97 (s, 3H), 3.86 (s, 3H), 4.92 (d, 1H, J= 7 Hz), 5.38 (s, 2H), 7.10 (d, 2H, J=9 Hz), 7.24 (m, 4H), 7.58 (d, 1H, J=9 Hz), 7.65 (d, 1H, J=9 Hz), 12.88 (broad s, 1H). MS DCI/NH$_3$) m/e 436 (M+H)$^+$. Analysis calcd. for $C_{25}H_{29}N_3O_4$: C, 68.95; H, 6.71; N, 9.65. Found: C, 68.49; H, 6.71; N, 9.56.

EXAMPLE 69

Preparation of
[Cyclohexyl-(4-(2-benzoxazolylmethoxy)phenyl)-methyl]iminoxyacetic acid.

The desired material was prepared according to the procedure of Example 1 substituting 2-chloromethylbenzoxazole for 2-chloromethylquinoline, mp. 112° C.; $^1$H NMR (300 MHz, DMSO-$d_6$) d: 1.08 (m, 6H), 1.73 (m, 5H), 4.90 (d, 2H, J=9 Hz), 5.45 (s, 2H), 7.05 (d, 2H, J=9 Hz), 7.21 (d, 2H, J=9 Hz), 7.43 (m, 2H), 7.55 (s, 1H), 7.80 (m, 2H), 13.25 (broad s, 1H); MS (DCI/NH$_3$) m/e: 409 (M+1); Analysis calcd. for $C_{23}H_{24}N_2O_5$x0.5 H$_2$O: C, 66.17; H, 5.98; N, 6.71; Found: C, 66.50; H, 6.09; N, 6.90.

EXAMPLE 70

Preparation of
[Cyclohexyl-(4-(2-quinolylmethoxy)phenyl)-methyl]-2-iminoxy propionic acid 2-thiazolylamide.

To a solution of [cyclohexyl-(4-(2-quinolinylmethoxy)phenyl)methyl]-2-iminoxypropionic acid (207 mg, 0.48 mmol), prepared as in Example 2, in THF (15 ml) at 0° C. was added triethylamine (0.20 ml, 1.40 mmol) followed by dropwise addition of methanesulfonyl chloride (0.074 ml, 0.96 mmol). Upon completion of addition, the reaction was stirred for 10 min and then dimethylaminopyridine (117 mg, 0.96 mmol) was added to the reaction mixture. After an additional 10 min., 2-aminothiazole (58 mg, 0.575 mmol) was added, and the reaction was allowed to warm to room temperature. The reaction was left at ambient temperature for 12 hours, and then was concentrated in vacuo. To the residue was added water and the resulting solution was extracted with methylene chloride. The organic layer was then washed with brine, dried over MgSO$_4$, and concentrated in vacuo. The residue was purified by silica gel flash chromatography (hexane-ethyl acetate 2:1) to give 80 mg of [Cyclohexyl-(4-(2-quinolylmethoxy)phenyl)methyl]-2-iminoxy propionic acid 2-thiazolylamide as a white powder. m.p. 61°–65° C. $^1$H NMR (300 MHz, DMSO-$d_6$) δ 1.10 (m, 5H), 1.38 (m, 1H), 1.66 (m, 3H), 1.89 (m, 2H), 2.06 (s, 3H), 5.06 (d, 1H, J=9 Hz), 5.35 (s, 2H), 7.04 (d, 2H, J=9 Hz), 7.25 (m, 3H), 7.51 (d, 1H, J=3 Hz), 7.62 (m, 1H), 7.67 (d, 1H, J=9 Hz), 7.78 (m, 1H), 8.0 (t, 2H, J=9 Hz), 8.40 (d, 1H, J=9 Hz), 11.67 (s, 1H). MS (DCI/NH$_3$) m/e 515 (M+H)$^+$. Analysis cald. for $C_{29}H_{30}N_4O_3S$: C, 67.68; H, 5.88; N, 10.89. Found: C, 67.60; H, 5.91; N, 10.40.

EXAMPLE 71

Preparation of
[Cyclohexyl-(4-(2-quinolinylmethoxy)phenyl)-methyl]-2-iminoxy propionic acid 2-pyridylamide.

To a solution of [cyclohexyl-(4-(2-quinolinylmethoxy)phenyl)methyl]-2-iminoxypropionic acid(200 mg, 0.46 mmol), prepared as in Example 2, and triethylamine (0.13 ml, 0.93 mmol) in THF (5 ml) at 0° C. was added dropwise methanesulfonyl chloride (0.04 ml, 0.51 mmol). Upon completion of addition, the reaction mixture was stirred at 0° C. for 1.3 hours. A solution of 2-aminopyridine (50 mg, 0.56 mmol) and DMAP (110 mg, 0.93 mmol) in THF (5 ml) was added, the cooling bath was withdrawn and the reaction was allowed to warm to room temperature. The mixture was left at ambient temperature for 12 hours. The reaction was quenched with water and extracted with ethyl acetate (2×50 ml). The organic layer was washed with water and brine, dried over MgSO$_4$ and concentrated in vacuo. The residue was purified by silica gel flash chromatography (hexane-ethyl acetate 2:1) to afford 161 mg of [Cyclohexyl-(4-(2-quinolinylmethoxy)phenyl)methyl]-2-iminoxy propionic acid 2-pyridylamide as a white powder. m.p. 49°–54° C. $^1$H NMR (300 MHz, DMSO-$d_6$) δ 1.06 (m, 5H), 1.38 (m, 1H), 1.66 (m, 3H), 1.84 (m, 2H), 2.06 (s, 3H), 5.05 (d, 1H, J=9 Hz), 5.35 (s, 2H), 7.06 (d,2H, J=9 Hz), 7.15 (m, 1H), 7.25 (d, 2H, J=9 Hz), 7.61 (m, 1H), 7.67 (d, 1H, J=9 Hz), 7.80 (m, 2H), 8.01 (m, 3H), 8.31 (m, 1H), 8.39 (d, 1H, J=9 Hz), 9.30 (s, 1H). MS (DCI/NH$_3$) m/e 509(M+H)$^+$. Analysis cacld. for $C_{31}H_{32}N_4O_3$: C, 73.21; H, 6.34; N, 11.02. Found: C, 73.02; H, 6.32; N, 10.87.

EXAMPLE 72

Preparation of
[Cyclohexyl-(4-(2-quinolinylmethoxy)phenyl)-methyl]-2-iminoxypropionic acid 5-tetrazylamide.

The desired material was prepared according to the procedure of Example 71, except substituting 5-aminotetrazole for 2-aminopyridine and by adding a small amount of DMF (2 ml) to solublize the 5-aminotetrazole. m.p. 180°–184° C. $^1$H NMR (300 MHz, DMSO-$d_6$) δ 1.07 (m, 5H), 1.39 (m, 1H), 1.66 (m, 3H), 1.91 (m, 2H), 2.05 (s, 3H), 5.05 (d, 1H, J=9 Hz), 5.35 (s, 2H), 7.05 (d, 2H, J= 9 Hz), 7.25 (d, 2H, J=9Hz), 7.61 (m, 1H), 7.67 (d, 1H, J=9 Hz), 7.78 (m, 1H), 8.0 (t, 2H, J=9 Hz), 8.40 (d, 1H, J=9 Hz), 11.30 (br s, 1H). MS (DCI/NH$_3$) m/e 500 (M+H)$^+$. Analysis calcd. for $C_{27}H_{29}N_7O.1.20H_2O$: C, 62.22; H, 6.07; N, 18.81. Found: C, 61.99; H, 5.76; N, 18.75.

The examples shown in Table 4 are prepared in a manner analogous to that of Example 2 substituting the requisite aldehyde prepared by known literature methods and the requisite organometallic reagent for addition reaction to the aldehyde shown to provide the final product examples illustrated.

TABLE 4

| Example | Aldehyde | Final Product |
|---|---|---|
| 73 | 4-CHO-phenyl-O-CH2-(4-pyridyl); [Cyclohexyl-(4-(4-pyridylmethoxy)phenyl)methyl]-2-iminoxypropionic acid | Cyclohexyl-(4-(4-pyridylmethoxy)phenyl)methyl oxime with COOH |
| 74 | 4-CHO-phenyl-O-CH2-(3-pyridyl); [Cyclohexyl-(4-(3-pyridylmethoxy)phenyl)methyl]-2-iminoxypropionic acid | Cyclohexyl-(4-(3-pyridylmethoxy)phenyl)methyl oxime with COOH |
| 75 | 4-CHO-phenyl-O-CH2-(2-pyridyl); [Cyclohexyl-(4-(2-pyridylmethoxy)phenyl)methyl]-2-iminoxypropionic acid | Cyclohexyl-(4-(2-pyridylmethoxy)phenyl)methyl oxime with COOH |

TABLE 4-continued

| Example | Aldehyde | → | Final Product |
|---|---|---|---|
| 76 | 4-(2-thiazolylmethoxy)benzaldehyde | | [Cyclohexyl-(4-(2-thiazolylmethoxy)phenyl)methyl]-2-iminoxypropionic acid |
| 77 | 4-(4-thiazolylmethoxy)benzaldehyde | | [Cyclohexyl-(4-(4-thiazolylmethoxy)phenyl)methyl]-2-iminoxypropionic acid |
| 78 | 4-(5-thiazolylmethoxy)benzaldehyde | | [Cyclohexyl-(4-(5-thiazolylmethoxy)phenyl)methyl]-2-iminoxypropionic acid |

TABLE 4-continued

| Example | Aldehyde | Final Product |
|---|---|---|
| 79 | [Cyclohexyl-(4-(2-quinolylmethoxy)phenyl-4-phenyl)methyl]-2-iminoxypropionic acid | |
| 80 | [Cyclohexyl-(6-(2-quinolylmethoxy)naphth-2-yl)methyl]-2-iminoxypropionic acid | |
| 81 | [Cyclohexyl-(6-(2-quinolylmethoxy)-1,2,3,4-tetrahydronaphth-2-yl)methyl]-2-iminoxypropionic acid | |

TABLE 4-continued

| Example | Aldehyde | → | Final Product |
|---|---|---|---|
| 82 | [Cyclohexyl-(1-methyl-6-(2-quinolylmethoxy)indol-2-yl)methyl]-2-iminoxypropionic acid | | |
| 83 | [Cycloheptyl-(6-(2-quinolylmethoxy)benzo[b]thien-2-yl)methyl]-2-iminoxypropionic acid | | |
| 84 | [Cyclohexyl-(4-(2-quinolylethyl)phenyl)methyl]-2-iminoxypropionic acid | | |

TABLE 4-continued

| Example | Aldehyde | Final Product |
|---|---|---|
| 85 | 4-(2-quinolylethenyl)benzaldehyde | [Cyclohexyl-(4-(2-quinolylethenyl)phenyl)methyl]-2-iminoxypropionic acid |
| 86 | 4-(2-quinolyloxymethyl)benzaldehyde | [Cyclohexyl-(4-(2-quinolyloxymethyl)phenyl)methyl]-2-iminoxypropionic acid |
| 87 | 4-(2-quinolylthiomethyl)benzaldehyde | [Cyclohexyl-(4-(2-quinolylthiomethyl)phenyl)methyl]-2-iminoxypropionic acid |

TABLE 4-continued
| Example | Aldehyde | Final Product |
|---|---|---|
| 88 | 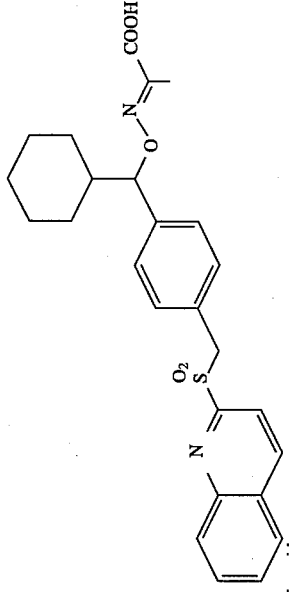<br>[Cyclohexyl-(4-(2-quinolylsulfonylmethyl)phenyl)methyl]-2-iminoxypropionic acid | 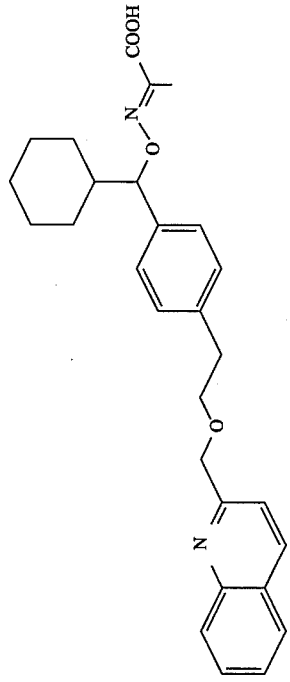 |
| 89 | 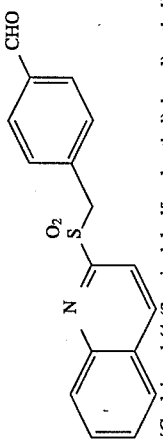<br>[Cyclohexyl-(4-(2-quinolylethynyl)phenyl)methyl]-2-iminoxypropionic acid | 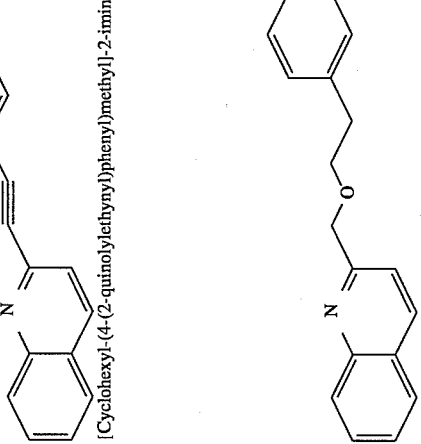 |
| 90 | 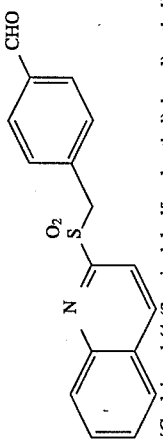<br>[Cyclohexyl-(4-(2-quinolylmethoxyethyl)phenyl)methyl]-2-iminoxypropionic acid | 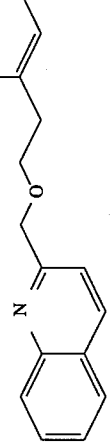 |

TABLE 4-continued
| Example | Aldehyde | | Final Product |
|---|---|---|---|
| 91 | 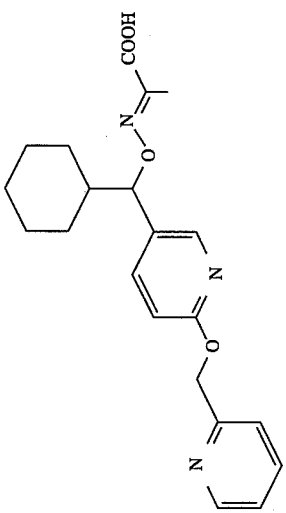<br>[Cyclohexyl-(2-(2-pyridylmethoxy)pyrid-5-yl)methyl]-2-iminoxypropionic acid | → |  |
| 92 | 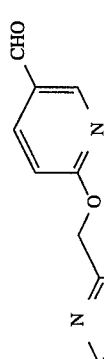<br>[Cyclohexyl-(5-(2-quinolylmethoxy)thien-2-yl)methyl]-2-iminoxypropionic acid | → | 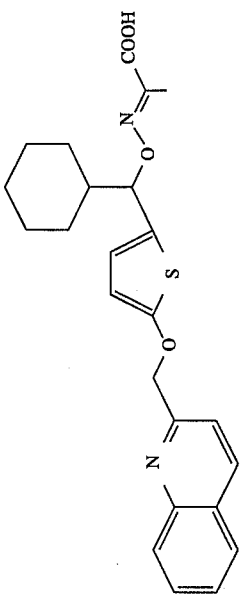 |
| 93 | 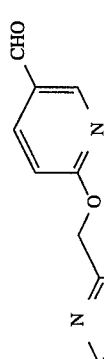<br>[Cyclohexyl-(2-(2-quinolylmethoxy)thien-5-yl)methyl]-2-iminoxypropionic acid | → | 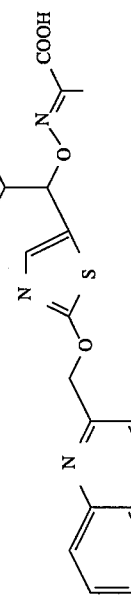 |

TABLE 4-continued

| Example | Aldehyde | → | Final Product |
|---|---|---|---|
| 94 | [Cyclohexyl-(6-(2-quinolylmethoxy)benzo[b]fur-2-yl)methyl]-2-iminoxypropionic acid | | [Cyclohexyl-(6-(2-quinolylmethoxy)benzo[b]fur-2-yl)methyl]-2-iminoxypropionic acid |
| 95 | [Cyclopentyl-(4-(2-quinoxyalylmethoxy)phenyl)methyl]-2-iminoxypropionic acid | | [Cyclopentyl-(4-(2-quinoxyalylmethoxy)phenyl)methyl]-2-iminoxypropionic acid |
| 96 | [Cyclohexyl-(4-(thiazolo[4,5-b]pyrid-6-ylmethoxy)phenyl)methyl]-2-iminoxypropionic acid | | [Cyclohexyl-(4-(thiazolo[4,5-b]pyrid-6-ylmethoxy)phenyl)methyl]-2-iminoxypropionic acid |

TABLE 4-continued

| Example | Aldehyde | → | Final Product |
|---|---|---|---|
| 97 | 4-(thiazolo[5,4-b]pyrid-6-ylmethoxy)benzaldehyde | | [Cyclohexyl-(4-(thiazolo[5,4-b]pyrid-6-ylmethoxy)phenyl)methyl]-2-iminoxypropionic acid |
| 98 | 4-(2-pyrimidylmethoxy)benzaldehyde | | [Cyclopentyl-(4-(2-pyrimidylmethoxy)phenyl)methyl]-2-iminoxypropionic acid |

TABLE 4-continued

| Example | Aldehyde | Final Product |
|---|---|---|
| 99 | [4-(4-phenylthiazol-2-ylmethoxy)benzaldehyde] | [Cyclohexyl-(4-((4-phenylthiazol-2-ylmethoxy)phenyl)methyl]-2-iminoxypropionic acid |
| 100 | [4-((4-pyrid-2-yl)thiazol-2-ylmethoxy)benzaldehyde] | [Cyclohexyl-(4-((4-pyrid-2-yl)thiazol-2-ylmethoxy)phenyl)methyl]-2-iminoxypropionic acid |

The following examples of this invention shown in Table 5 are prepared according to the method of Example 2 substituting the requisite organometallic addition reagent shown in Table 5 for cyclohexylmagnesium bromide.

TABLE 5

| Example | Organometallic Reagent | → | Product |
|---|---|---|---|

101

Ph-MgBr

[Phenyl-(4-(2-quinolylmethoxy)phenyl)methyl]-2-iminoxypropionic acid

102

5-methylthien-2-yl-Li

[5-Methylthien-2yl-(4-(2-quinolylmethoxy)phenyl)methyl]-2-iminoxypropionic acid

103 pyridyl-Li

[Pyrid-2-yl-(4-(2-quinolylmethoxy)phenyl)methyl]-2-iminoxypropionic acid

104 cyclopropylpropyl-MgBr

[3-Cyclopropylpropyl-(4-(2-quinolylmethoxy)phenyl)methyl]-2-iminoxypropionic acid

105

BuO-CH2-Li

[Butyloxymethyl-(4-(2-quinolylmethoxy)phenyl)methyl]-2-iminoxypropionic acid

TABLE 5-continued

| Example | Organometallic Reagent | → | Product |
|---|---|---|---|

106

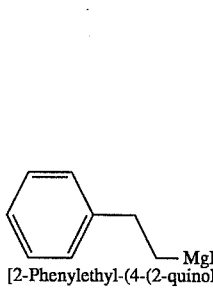
[2-Phenylethyl-(4-(2-quinolylmethoxy)phenyl)methyl]-2-iminoxypropionic acid

107

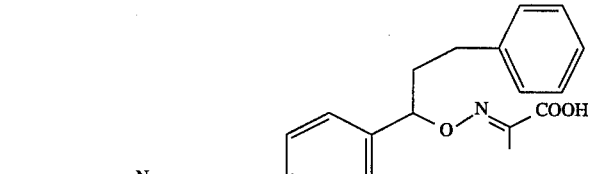
[2-Pyrid-4-ylethyl-(4-(2-quinolylmethoxy)phenyl)methyl]-2-iminoxypropionic acid

108

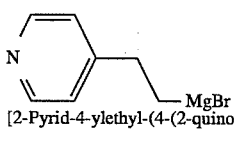
[2-Furyl-(4-(2-quinolylmethoxy)phenyl)methyl]-2-iminoxypropionic acid

109

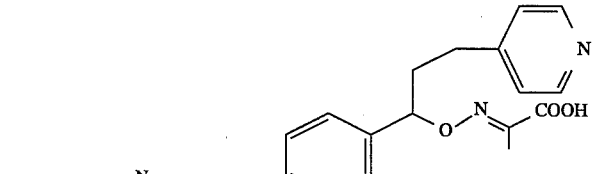
[2-Thiazolyl-(4-(2-quinolylmethoxy)phenyl)methyl]-2-iminoxypropionic acid

110

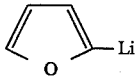
[4-Perhydropyranyl-(4-(2-quinolylmethoxy)phenyl)methyl]-2-iminoxypropionic acid The compounds shown in Table 6 are prepared by convening the carboxylate examples described above into the corresponding hydroxyamides named as follows using known procedures in the literature to effect this functional transformation: for example by reacting the carboxlate example with oxalyl chloride to provide the corresponding acyl chloride intermediate which is directly treated with the requisite hydroxyl amine to provide the named examples that follow in Table 6.

TABLE 6

| Example | Hydroxyamide |
|---|---|
| 111 | [Cyclohexyl-(4-(2-quinolylmethoxy)phenyl)methyl]iminoxyaceto-N-hydroxyamide |
| 112 | [Cyclohexyl-(4-(2-quinolylmethoxy)phenyl)methyl]-2-iminoxypropionyl-N-methyl-N-hydroxyamide |
| 113 | [Cyclohexyl-(4-(2-quinolylmethoxy)phenyl)methyl]-4-iminoxypentanoyl-N-methyl-N-hydroxyamide |
| 114 | [Cyclohexyl-(4-(2-quinolylmethoxy)phenyl)methyl]-2-iminoxy-3-(4-hydroxyphenyl)propionyl-N-methyl-N-hydroxyamide |
| 115 | [Cyclohexyl-(4-(2-quinolylmethoxy)phenyl)methyl]-2-iminoxy-3-phenylpropionyl-N-methyl-N-hydroxyamide |
| 116 | [Cyclohexyl-(4-(2-quinolylmethoxy)phenyl)methyl]-3-iminoxy-(2,2-dimethyl)propionyl-N-methyl-N-hydroxyamide |
| 117 | [Cyclopentyl-(4-(2-quinolylmethoxy)phenyl)methyl]iminoxyaceto-N-hydroxyamide |
| 118 | [Cyclopentyl-(4-(2-quinolylmethoxy)phenyl)methyl]-2-iminoxypropionyl-N-methyl-N-hydroxyamide |
| 119 | [1,2,3,4-Tetrahydro-6-(2-quinolylmethoxy)naphth-1-yl]iminoxyaceto-N-hydroxyamide |
| 120 | [1,2,3,4-Tetrahydro-6-(2-quinolylmethoxy)naphth-1-yl]-2-iminoxypropionyl-N-methyl-N-hydroxyamide |
| 121 | [4-(4-Chlorophenyl)-1-(4-(2-quinolylmethoxy)phenyl)butyl]iminoxyaceto-N-hydroxyamide |
| 122 | [2-Cyclohexyl-1-(4-(2-quinolylmethoxy)phenyl)eth-1-yl]iminoxyaceto-N-hydroxyamide |
| 123 | [2-Cyclohexyl-1-(4-(2-quinolylmethoxy)phenyl)eth-1-yl]-2-iminoxypropionyl-N-methyl-N-hydroxyamide |
| 124 | [2-Cyclohexyl-1-(4-(2-quinolylmethoxy)phenyl)eth-1-yl]-4-iminoxypentanoyl-N-methyl-N-hydroxyamide |
| 125 | [Cycloheptyl-(4-(2-quinolylmethoxy)phenyl)methyl]iminoxyaceto-N-hydroxyamide |
| 126 | [3-Cyclohexyl-2-[4-(2-quinolylmethoxy)phenyl)prop-1-yl]iminoxyaceto-N-hydroxyamide |
| 127 | [3-Cyclohexyl-2-(4-(2-quinolylmethoxy)phenyl)prop-1-yl]-2-iminoxypropionyl-N-methyl-N-hydroxyamide |
| 128 | [3-Cyclohexyl-2-(4-(2-quinolylmethoxy)phenyl)prop-1-yl}-3-iminoxy-(2,2-dimethyl)propionyl-N-methyl-N-hydroxyamide |
| 129 | [4-(4-Fluorophenyl)-1-(4-(2-quinolylmethoxy)phenyl)but-1-yl]iminoxyaceto-N-hydroxyamide |
| 130 | [4-(4-Fluorophenyl)-1-(4-(2-quinolylmethoxy)phenyl)but-1-yl]-2-iminoxypropionyl-N-methyl-N-hydroxyamide |
| 131 | [2-Cyclohexyl-2-(4-(2-quinolylmethoxy)phenyl)eth-1-yl}-iminoxyaceto-N-hydroxyamide |
| 132 | [2-Cycloheptyl-2-(4-(2-quinolylmethoxy)phenyl)eth-1-yl]iminoxyaceto-N-hydroxyamide |
| 133 | [2-Cycloheptyl-2-(4-(2-quinolylmethoxy)phenyl)eth-1-yl]-3-iminoxy-2,2-dimethylpropionyl-N-methyl-N-hydroxyamide |
| 134 | [2-Cyclopentyl-2-(4-(2-quinolylmethoxy)phenyl)eth-1-yl]iminoxyaceto-N-hydroxyamide |
| 135 | [Cyclohexyl-(4-(2-quinolylmethoxy)phenyl)methyl]-Z-2-iminoxypropionyl-N-methyl-N-hydroxyamide |
| 136 | [Cyclohexyl-(4-(2-quinolylmethoxy)phenyl)methyl]-E-2-iminoxypropionyl-N-methyl-N-hydroxyamide |
| 137 | (R)-[Cyclohexyl-(4-(2-quinolylmethoxy)phenyl)methyl]-E-2-iminoxypropionyl-N-methyl-N-hydroxyamide |
| 138 | (S)-[Cyclohexyl-(4-(2-quinolylmethoxy)phenyl)methyl]-E-2-iminoxypropionyl-N-methyl-N-hydroxyamide |
| 139 | [Cyclohexyl-(4-(2-quinolylmethoxy)phenyl)methyl]-E-iminoxyaceto-N-hydroxyamide |
| 140 | [2-phenyl-1-(4-(2-quinolylmethoxy)phenyl)eth-1-yl]-Z-2-iminoxypropionyl-N-methyl-N-hydroxyamide |
| 141 | [2-phenyl-1-(4-(2-quinolylmethoxy)phenyl)eth-1-yl]-E-2-iminoxypropionyl-N-methyl-N-hydroxyamide |
| 142 | [2-thienyl-(4-(2-quinolylmethoxy)phenyl)methyl]-E-2-iminoxypropionyl-N-methyl-N-hydroxyamide |
| 143 | [Cyclohexyl-(2-chloro-4-(2-quinolylmethoxy)phenyl)methyl]-E-2-iminoxypropionyl-N-methyl-N-hydroxyamide |
| 144 | [Cyclohexyl-(3-chloro-4-(2-quinolylmethoxy)phenyl)methyl]-E-2-iminoxypropionyl-N-methyl-N-hydroxyamide |
| 145 | [Cyclohexyl-(2-chloro-4-(2-quinolylmethoxy)phenyl)methyl]-Z-2-iminoxypropionyl-N-methyl-N-hydroxyamide |
| 146 | [3-Methyl-3-phenyl-1-[4-(2-quinolylmethoxy)phenyl)but-1-yl]-Z-2-iminoxypropionyl-N-methyl-N-hydroxyamide |
| 147 | [3-Methyl-3-phenyl-1-(4-(2-quinolylmethoxy)phenyl)but-1-yl]-E-2-iminoxypropionyl-N-methyl-N-hydroxyamide |
| 148 | [3-Methyl-3-phenyl-1-(4-(2-quinolylmethoxy)phenyl)but-1-yl]-E-2-iminoxyacetic |
| 149 | [4-(2-Quinolylmethoxy)phenylpent-1-yl]-E-2-iminoxypropionyl-N-methyl-N-hydroxyamide |
| 150 | [4-(2-Quinolylmethoxy)phenyl)pent-1-yl]-E-iminoxyaceto-N-hydroxyamide |
| 151 | [4-(2-Quinolylmethoxy)phenyl)-but-3-en-1-yl]-E-iminoxy-2-propionyl-N-methyl-N-hydroxyamide |
| 152 | [Cyclohexyl-1-(4-(2-quinolylmethoxy)phenyl)eth-2-yl]-2-iminoxypropionyl-N-methyl-N-hydroxyamide |
| 153 | [Cycloheptyl-(4-(2-quinolylmethoxy)phenyl)eth-2-yl]-2-iminoxypropionyl-N-methyl-N-hydroxyamide |
| 154 | [2-chloro-(4-(2-quinolylmethoxy)phenyl)methyl]-2-iminoxypropionyl-N-methyl-N-hydroxyamide |
| 155 | [Cycloheptyl-(4-(2-quinolylmethoxy)phenyl)methyl]-2-iminoxypropionyl-N-methyl-N-hydroxyamide |
| 156 | (R)-[Cyclopentyl-(4-(2-quinolylmethoxy)phenyl)methyl]-E-2-iminoxypropionyl-N-methyl-N-hydroxyamide |
| 157 | (S)-[Cyclopentyl-(4-(2-quinolylmethoxy)phenyl)methyl]-E-2-iminoxypropionyl-N-methyl-N-hydroxyamide |
| 158 | [Cyclohexyl-(4-(2-quinolylmethoxy)benzo[b]thien-2-yl)methyl]-2-iminoxypropionyl-N-methyl-N-hydroxyamide |
| 159 | [Cyclohexyl-(6-(2-quinolylmethoxy)pyrid-3-yl)methyl]iminoxyaceto-N-hydroxyamide |
| 160 | [Cyclohexyl-(4-(6-(4-fluorophenoxy)pyrid-2-ylmethoxy)phenyl)methyl]iminoxyaceto-N-hydroxyamide |
| 161 | [2-Cyclohexyl-1-(4-(4-thiazolylmethoxy)phenyl)eth-1-yl]iminoxyaceto-N-hydroxyamide |
| 162 | [2-Cyclohexyl-1-(4-(4-thiazolylmethoxy)phenyl)eth-1-yl]-2-iminoxypropionyl-N-methyl-N-hydroxyamide |
| 163 | [Cyclohexyl-(4-(4-thiazolylmethoxy)phenyl)methyl]-2-iminoxypropionyl-N-methyl-N-hydroxyamide |
| 164 | [Cyclohexyl-(4-(4-thiazolylmethoxy)phenyl)methyl]iminoxyaceto-N-hydroxyamide |
| 165 | [Cyclohexyl-(4-(2-benzothiazolylmethoxy)phenyl)methyl]iminoxyaceto-N-hydroxyamide |
| 167 | [Cyclohexyl-(4-(1-methyl-2-benzimidazolylmethoxy)phenyl)methyl]-2-iminoxypropionyl-N-methyl-N-hydroxyamide |
| 168 | [Cyclohexyl-(4-(2-benzoxazolylmethoxy)phenyl)methyl]iminoxyaceto-N-hydroxyamide |

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:

1. A compound of formula

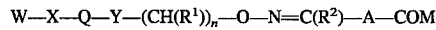

or a pharmaceutically acceptable salt thereof wherein
n is zero or 1 with the proviso that n is zero when Y is tetrahydronaphthyl;

W is selected from the group consisting of
  (a) quinolyl, and
  (b) quinolyl substituted with
    halogen,
    alkyl of one to six carbon atoms, or
    alkoxy of one to six carbon atoms;
X is selected from the group consisting of
  alkylene of one to six carbon atoms,
  alkenylene of two to six carbon atoms,
  alkynylene of two to six carbon atoms,
  alkoxy of one to six carbon atoms,
  thioalkyloxy of one to six carbon atoms, and
  alkylsulfonyl of one to six carbon atoms,
Q is a valence bond or is selected from the group consisting of
  —O—,
  —S—,
  >$NR^4$ where $R^4$ is hydrogen, or alkyl of one to six carbon atoms, and
  >$NCOR^5$ where $R^5$ is alkyl of one to six carbon atoms, amino, or alkylamino of one to six carbon atoms;
Y is selected from the group consisting of
  (a) phenyl,
  (b) phenyl substituted with
    halogen,
    alkyl of one to six carbon atoms, or
    alkoxy of one to six carbon atoms,
  (c) biphenyl,
  (d) biphenyl substituted with
    halogen,
    alkyl of one to six carbon atoms, or
    alkoxy of one to six carbon atoms,
  (e) naphthyl,
  (f) naphthyl substituted with
    halogen,
    alkyl of one to six carbon atoms, or
    alkoxy of one to six carbon atoms,
  (g) tetrahydronaphthyl,
  (h) tetrahydronaphthyl substituted with
    halogen,
    alkyl of one to six carbon atoms, or
    alkoxy of one to six carbon atoms;
$R^1$ is selected from the group consisting of
  (a) alkyl of one to twelve carbon atoms,
  (b) cycloalkyl of three to ten carbon atoms,
  (c) cycloalkyl of three to ten carbon atoms containing one atom selected from
    —O—,
    —S—,
    >$NR^4$ where $R^4$ is hydrogen, or alkyl of one to six carbon atoms, and
    >$NCOR^5$ where $R^5$ is alkyl of one to six carbon atoms, amino, or aminoalkyl of one to six carbon atoms,
  (d) alkoxyalkyl in which the alkoxy and alkyl portions independently are of one to twelve carbon atoms,
  (e) phenyl,
  (f) phenyl substituted with
    halogen,
    alkyl of one to six carbon atoms,
    haloalkyl of one to six carbon atoms, or
    alkoxy of one to six carbon atoms,
  (g) phenylalkyl in which the alkyl portion is of one to six carbon atoms,
  (h) phenylalkyl in which the alkyl portion is of one to six carbon atoms, and the phenyl ting is substituted with
    halogen,
    alkyl of one to six carbon atoms,
    haloalkyl of one to six carbon atoms, or
    alkoxy of one to six carbon atoms;
$R^2$ is selected from the group consisting of
  hydrogen,
  alkyl of one to six carbon atoms, and
  hydroxyalkyl of one to six carbon atoms;
A is a valence bond or is selected from the group consisting of:
  (a) alkylene of one to six carbon atoms,
  (b) cycloalkylene of three to eight carbon atoms,
  (c) phenyl,
  (d) phenyl substituted with
    halogen,
    alkyl of one to six carbon atoms,
    haloalkyl of one to six carbon atoms, or
    alkoxy of one to six carbon atoms,
  (e) phenylalkyl in which the alkyl portion is of one to six carbon atoms,
  (f) phenylalkyl in which the alkyl portion is of one to six carbon atoms, and the phenyl ring is substituted with
    halogen,
    alkyl of one to six carbon atoms,
    haloalkyl of one to six carbon atoms, or
    alkoxy of one to six carbon atoms;
M is selected from the group consisting of
  a pharmaceutically acceptable, metabolically cleavable group,
  —$OR^6$ where $R^6$ is selected from hydrogen or alkyl of one to six carbon atoms,
  —$NR^6R^7$ wherein $R^7$ is selected from
    hydrogen,
    alkyl of one to six carbon atoms,
    hydroxy,
    alkoxy or one to six carbon atoms.

2. A compound as defined in claim 1, or a pharmaceutically acceptable salt thereof selected from the group consisting of
[cyclohexyl-(4-(2-quinolylmethoxy)phenyl)methyl]iminoxyacetic acid,
[cyclohexyl-(4-(2-quinolyl methoxy)phenyl)methyl]-2-iminoxy propionic acid,
[cyclohexyl-(4-(2-quinolylmethoxy)phenyl)methyl]-4-iminoxy pentanoic acid,
[cyclohexyl-(4-(2-quinolylmethoxy)phenyl)methyl]-2-iminoxy-3-(4-hydroxyphenyl)propionic acid,
[cyclohexyl-(4-(2-quinolylmethoxy)phenyl)methyl]-2-iminoxy-3-phenylpropionic acid,
O-[cyclohexyl-(4-(2-quinolylmethoxy)phenyl)methyl]-4-carboxybenzaldoxime,
[cyclohexyl-(4-(2-quinolylmethoxy)phenyl)methyl]-3-iminoxy-(2,2-dimethyl)propionic acid,
[cyclopentyl-(4-(2-quinolylmethoxy)phenyl)methyl]iminoxy acetic acid,
[cyclopentyl-(4-(2-quinolylmethoxy)phenyl)methyl]-2-iminoxy propionic acid,
[1,2,3,4-tetrahydro-6-(2-quinolylmethoxy)naphth-1-yl]iminoxy acetic acid,
[1,2,3,4-tetrahydro-6-(2-quinolylmethoxy)naphth-1-yl]-2-iminoxypropionic acid,
[4-(4-chlorophenyl)-1-(4-(2-quinolylmethoxy)phenyl)butyl]iminoxyacetic acid,

[2-cyclohexyl-1-(4-(2-quinolylmethoxy)phenyl)eth-1-yl]
iminoxyacetic acid,
O-[2-cyclohexyl-1-(4-(2-quinolylmethoxy)phenyl)eth-1-yl]
-4-carboxybenzaldoxime,
[2-cyclohexyl-1-(4-(2-quinolylmethoxy)phenyl)eth-1-yl]-2-
iminoxypropionic acid,
[2-cyclohexyl-1-(4-(2-quinolylmethoxy)phenyl)eth-1-yl]-4-
iminoxypentanoic acid,
[cycloheptyl-(4-(2-quinolylmethoxy)phenyl)methyl]iminoxy acetic acid,
[3-cyclohexyl-2-[4-(2-quinolylmethoxy)phenyl)prop-1-yl]
iminoxy acetic acid,
[3-cyclohexyl-2-(4-(2-quinolylmethoxy)phenyl)prop-1-yl]-
2-iminoxypropionic acid,
[3-cyclohexyl-2-(4-(2-quinolylmethoxy)phenyl)prop-1-yl}-
3-iminoxy-(2,2-dimethyl)propionic acid,
[4-(4-fluorophenyl)-1-(4-(2-quinolylmethoxy)phenyl)but-1-
yl]iminoxyacetic acid,
[4-(4-fluorophenyl)-1-(4-(2-quinolylmethoxy)phenyl)but-1-
yl]-2-iminoxypropionic acid,
[2-cyclohexyl-2-(4-(2-quinolylmethoxy)phenyl)eth-1-yl}-
iminoxyacetic acid,
[2-cycloheptyl-2-(4-(2-quinolylmethoxy)phenyl)eth-1-yl]
iminoxyacetic acid,
[2-cycloheptyl-2-(4-(2-quinolylmethoxy)phenyl)eth-1-yl]-
3-iminoxy-2,2-dimethylpropionic acid,
[2-cyclopentyl-2-(4-(2-quinolylmethoxy)phenyl)eth-1-yl]
iminoxyacetic acid,
[cyclohexyl-(4-(2-quinolylmethoxy)phenyl)methyl]-Z-2-
iminoxypropionic acid methyl ester,
[cyclohexyl-(4-(2-quinolylmethoxy)phenyl)methyl]-E-2-
iminoxypropionic acid methyl ester,
[cyclohexyl-(4-(2-quinolylmethoxy)phenyl)methyl]-Z-2-
iminoxy propionic acid,
[cyclohexyl-(4-(2-quinolylmethoxy)phenyl)methyl]-E-2-
iminoxy propionic acid,
(R)-[cyclohexyl-(4-(2-quinolylmethoxy)phenyl]methyl]-E-
2-iminoxypropionic acid methyl ester,
(R)-[cyclohexyl-(4- (2-quinolylmethoxy)phenyl) methyl]-
E-2-iminoxypropionic acid,
(S)-[cyclohexyl-(4-(2-quinolylmethoxy)phenyl) methyl]-E-
2-iminoxypropionic acid methyl ester,
(S)-[cyclohexyl-(4-(2-quinolylmethoxy)phenyl)methyl]-E-
2-iminoxypropionic acid,
[cyclohexyl-(4-(2-quinolylmethoxy)phenyl)methyl]-Z-iminoxy acetic acid methyl ester,
[cyclohexyl-(4-(2-quinolylmethoxy)phenyl)methyl]-E-iminoxy acetic acid methyl ester,
[cyclohexyl-(4-(2-quinolylmethoxy)phenyl)methyl]-E-iminoxy acetic acid,
[2-phenyl-1-(4-(2-quinolylmethoxy)phenyl)eth-1-yl]-Z-2-
iminoxy propionic acid,
[2-phenyl-1-(4-(2-quinolylmethoxy)phenyl)eth-1-yl]-E-2-
iminoxy propionic acid,
[2-thienyl-(4-(2-quinolylmethoxy)phenyl)methyl]-E-2-iminoxy propionic acid,
[cyclohexyl-(2-chloro-4-(2-quinolylmethoxy)phenyl)methyl]-E-2-iminoxypropionic acid,
[cyclohexyl-(3-chloro-4-(2-quinolylmethoxy)phenyl)methyl]-E-2-iminoxypropionic acid,
[cyclohexyl-(2-chloro-4-(2-quinolylmethoxy)phenyl)methyl]-Z-2-iminoxypropionic acid,
[3- methyl-3-phenyl-1- [4-(2-quinolylmethoxy)phenyl)but-
1- yl]-Z-2-iminoxypropionic acid,
[3-methyl-3-phenyl-1-(4-(2-quinolylmethoxy)phenyl)but-1-
yl]-E-2-iminoxypropionic acid,
[3-methyl-3-phenyl-1-(4-(2-quinolylmethoxy)phenyl)but-1-
yl]-E-2-iminoxyacetic,
[4-(2-quinolylmethoxy)phenylpent-1-yl]-E-2-iminoxypropionic acid,
[4-(2-quinolylmethoxy)phenyl)pent-1-yl]-E-iminoxyacetic acid,
[4-(2-quinolylmethoxy)phenyl)-but-3-en-1-yl]-E-iminoxy-
2-propionic acid,
[cyclohexyl-(4-(2-quinolylmethoxy)phenyl)methyl]-E-2-
iminoxy butanoic acid,
[cyclohexyl-(4-(2-quinolylmethoxy)phenyl)methyl]-E-3-
iminoxybutanoic acid,
[cyclohexyl-1-(4-(2-quinolylmethoxy)phenyl)eth-2-yl]-2-
iminoxy propionic acid,
[cycloheptyl-(4-(2-quinolylmethoxy)phenyl)eth-2-yl]-2-
iminoxy propionic acid,
[2-chloro-(4-(2-quinolylmethoxy)phenyl)methyl]-2-iminoxy propionic acid,
[cycloheptyl-(4-(2-quinolylmethoxy)phenyl)methyl]-2-iminoxy propionic acid,
sodium [cyclohexyl-(4-(2-quinolylmethoxy)phenyl)methyl]
-2-iminoxypropionate,
(R)-[cyclopentyl-(4-(2-quinolylmethoxy)phenyl)methyl]-E-
2-iminoxypropionic acid,
(S)-[cyclopentyl-(4-(2-quinolylmethoxy)phenyl)methyl]-E-
2-iminoxypropionic acid.

3. A compound as defined in claim 1, or a pharmaceutically acceptable salt thereof selected from the group consisting of

[Cyclohexyl-(4-(2-quinolylmethoxy)phenyl)methyl]iminoxyacetic acid,
[Cyclohexyl-(4-(2-quinolylmethoxy)phenyl)methyl]-2-iminoxypropionic acid,
(R)-[Cyclohexyl-(4-(2-quinolylmethoxy)phenyl)methyl]-2-
iminoxypropionic acid,
(S)-[Cyclohexyl-(4-(2-quinolylmethoxy)phenyl)methyl]-2-
iminoxypropionic acid,
[Cyclopentyl-(4-(2-quinolylmethoxy)phenyl)methyl]iminoxyacetic acid,
[Cyclopentyl-(4-(2-quinolylmethoxy)phenyl)methyl]-2-
iminoxypropionic acid,
(R)-[Cyclopentyl-(4-(2-quinolylmethoxy)phenyl)methyl]-
2-iminoxypropionic acid,
(S)-[Cyclopentyl-(4-(2-quinolylmethoxy)phenyl)methyl]-2-
iminoxypropionic acid, and
[2-Cyclohexyl-1-(4-(2-quinolylmethoxy)phenyl)ethyl]iminoxyacetic acid.

4. A method for inhibiting lipoxygenase activity or leukotriene biosynthesis in a mammal in need of such treatment, comprising administering to the mammal a therapeutically effective amount of a compound of claim 1.

5. A composition for inhibiting lipoxygenase activity or the biosynthesis of leukotrienes comprising a pharmaceutical carrier and a therapeutically effective amount of a compound of claim 1.

* * * * *

UNITED STATES PATENT AND TRADEMARK OFFICE
CERTIFICATE OF CORRECTION

PATENT NO. : 5,512,581
DATED : April 30, 1996
INVENTOR(S) : Brooks et. Al.

It is certified that error appears in the above-indentified patent and that said Letters Patent is hereby corrected as shown below:

Column 4, line 50, change "comprising-administering" to --comprising administering--.

Column 78, line 2, change "ting" to --ring--.

Column 78, line 46, change "quinolyl methoxy" to --quinolylmethoxy--.

Signed and Sealed this

Tenth Day of June, 1997

Attest:

BRUCE LEHMAN

Attesting Officer    Commissioner of Patents and Trademarks